US008974461B2

(12) United States Patent
Abdou

(10) Patent No.: US 8,974,461 B2
(45) Date of Patent: Mar. 10, 2015

(54) DEVICES AND METHODS FOR INTER-VERTEBRAL ORTHOPEDIC DEVICE PLACEMENT

(76) Inventor: M. Samy Abdou, San Diego, CA (US)

(*) Notice: Subject to any disclaimer, the term of this patent is extended or adjusted under 35 U.S.C. 154(b) by 0 days.

(21) Appl. No.: 13/466,000

(22) Filed: May 7, 2012

(65) Prior Publication Data

US 2012/0221063 A1    Aug. 30, 2012

Related U.S. Application Data

(63) Continuation of application No. 11/286,152, filed on Nov. 23, 2005, now Pat. No. 8,172,855.

(60) Provisional application No. 60/631,213, filed on Nov. 24, 2004, provisional application No. 60/713,235, filed on Aug. 31, 2005.

(51) Int. Cl.
*A61B 17/70* (2006.01)
*A61B 17/58* (2006.01)
*A61F 2/46* (2006.01)
*A61B 17/02* (2006.01)
*A61B 19/00* (2006.01)

(52) U.S. Cl.
CPC ........... *A61F 2/4611* (2013.01); *A61B 17/7065* (2013.01); *A61B 17/7077* (2013.01); *A61B 17/7062* (2013.01); *A61B 2017/0256* (2013.01); *A61B 2019/461* (2013.01); *A61B 2019/462* (2013.01); *A61B 2019/464* (2013.01); *A61F 2002/4658* (2013.01); *A61F 2002/4662* (2013.01); *A61F 2002/4666* (2013.01); *A61F 2002/4687* (2013.01)
USPC ............................ 606/86 A; 606/90; 606/249

(58) Field of Classification Search
USPC ........................... 606/86 A, 90, 97, 246–278; 623/17.11–17.16
See application file for complete search history.

(56) References Cited

U.S. PATENT DOCUMENTS

| 2,248,054 A | 7/1941 | Becker |
| 3,090,386 A | 5/1963 | Babcock |
| 3,659,595 A | 5/1972 | Haboush |
| 4,037,592 A | 7/1977 | Kronner |
| 4,289,123 A | 9/1981 | Dunn |
| 4,569,662 A | 2/1986 | Dragan |
| 4,580,563 A | 4/1986 | Gross |

(Continued)

FOREIGN PATENT DOCUMENTS

| DE | 10035182 | 2/2002 |
| EP | 077159 | 4/1983 |

(Continued)

OTHER PUBLICATIONS

Derwent WPI Acc No. 2002-155861/200221 for German Patent No. DE 10035182 (item AG).

(Continued)

*Primary Examiner* — Matthew Lawson
(74) *Attorney, Agent, or Firm* — Gazdzinski & Associates, PC

(57) ABSTRACT

Devices and methods for implantation of an orthopedic device between skeletal segments using limited surgical dissection. The implanted devices are used to adjust and maintain the spatial relationship(s) of adjacent bones. Depending on the implant design, the motion between the skeletal segments may be increased, limited, modified, or completely immobilized.

34 Claims, 54 Drawing Sheets

(56) References Cited

U.S. PATENT DOCUMENTS

| | | |
|---|---|---|
| 4,722,331 A | 2/1988 | Fox |
| 4,790,303 A | 12/1988 | Steffee |
| 4,899,761 A | 2/1990 | Brown et al. |
| 4,903,692 A | 2/1990 | Reese |
| 4,932,975 A | 6/1990 | Main et al. |
| 5,002,576 A | 3/1991 | Fuhrmann et al. |
| 5,133,717 A | 7/1992 | Chopin |
| 5,254,118 A | 10/1993 | Mirkovic |
| 5,275,601 A | 1/1994 | Goglewski et al. |
| 5,330,468 A | 7/1994 | Burkhart |
| 5,334,205 A | 8/1994 | Cain |
| 5,354,292 A | 10/1994 | Braeuer et al. |
| 5,360,429 A | 11/1994 | Jeanson et al. |
| 5,456,714 A | 10/1995 | Owen |
| 5,484,440 A | 1/1996 | Allard |
| 5,531,747 A | 7/1996 | Ray |
| 5,545,164 A | 8/1996 | Howland |
| 5,558,674 A | 9/1996 | Heggeness et al. |
| 5,569,248 A | 10/1996 | Mathews |
| 5,609,634 A | 3/1997 | Voydeville |
| 5,616,142 A | 4/1997 | Yuan et al. |
| 5,645,599 A | 7/1997 | Samani |
| 5,672,176 A | 9/1997 | Biedermann et al. |
| 5,681,312 A | 10/1997 | Yuan et al. |
| 5,928,139 A | 7/1999 | Koros et al. |
| 5,928,233 A | 7/1999 | Apfelbaum et al. |
| 5,971,987 A | 10/1999 | Huxel et al. |
| 5,976,146 A | 11/1999 | Ogawa et al. |
| 5,993,449 A | 11/1999 | Schlapfer et al. |
| 6,039,761 A | 3/2000 | Li et al. |
| 6,059,786 A | 5/2000 | Jackson |
| 6,086,589 A | 7/2000 | Kuslich |
| 6,090,113 A | 7/2000 | Le Couedic et al. |
| 6,117,135 A | 9/2000 | Schlapfer et al. |
| 6,123,707 A | 9/2000 | Wagner |
| 6,139,549 A | 10/2000 | Keller |
| 6,159,244 A | 12/2000 | Suddaby et al. |
| 6,193,757 B1 | 2/2001 | Foley et al. |
| 6,306,136 B1 | 10/2001 | Baccelli |
| 6,309,391 B1 | 10/2001 | Crandall et al. |
| 6,312,431 B1 | 11/2001 | Asfora |
| 6,319,002 B1 | 11/2001 | Pond |
| 6,319,257 B1 | 11/2001 | Carignan et al. |
| 6,331,179 B1 | 12/2001 | Freid et al. |
| 6,332,882 B1 | 12/2001 | Zucherman et al. |
| 6,355,038 B1 | 3/2002 | Pisharodi |
| 6,402,752 B2 | 6/2002 | Schaffler-Wachter et al. |
| 6,419,676 B1 | 7/2002 | Zucherman et al. |
| 6,419,677 B2 | 7/2002 | Zucherman et al. |
| 6,428,576 B1 | 8/2002 | Haldimann |
| 6,432,140 B1 | 8/2002 | Lin |
| 6,440,133 B1 | 8/2002 | Beale et al. |
| 6,451,019 B1 | 9/2002 | Zucherman et al. |
| 6,451,020 B1 | 9/2002 | Zucherman et al. |
| 6,478,800 B1 | 11/2002 | Fraser et al. |
| 6,508,839 B1 | 1/2003 | Lambrecht et al. |
| 6,514,256 B2 | 2/2003 | Zucherman et al. |
| 6,524,315 B1 | 2/2003 | Selvitelli et al. |
| 6,530,929 B1 * | 3/2003 | Justis et al. .................. 606/103 |
| 6,547,790 B2 | 4/2003 | Harckey, III et al. |
| 6,558,386 B1 | 5/2003 | Cragg |
| 6,558,390 B2 | 5/2003 | Cragg |
| 6,599,294 B2 | 7/2003 | Fuss et al. |
| 6,599,295 B1 | 7/2003 | Tornier et al. |
| 6,645,207 B2 | 11/2003 | Dixon et al. |
| 6,663,631 B2 | 12/2003 | Kuntz et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,716,212 B1 | 4/2004 | Pickens |
| 6,730,126 B2 | 5/2004 | Boehm, Jr. et al. |
| 6,733,534 B2 | 5/2004 | Sherman |
| 6,739,068 B1 | 5/2004 | Rinner |
| 6,740,087 B2 | 5/2004 | Knox |
| 6,740,090 B1 | 5/2004 | Cragg et al. |
| 6,746,449 B2 | 6/2004 | Jones et al. |
| 6,749,614 B2 | 6/2004 | Teitelbaum et al. |
| 6,755,841 B2 | 6/2004 | Fraser et al. |
| 6,761,720 B1 | 7/2004 | Senegas |
| 6,783,547 B2 | 8/2004 | Castro |
| 6,790,210 B1 | 9/2004 | Cragg et al. |
| 6,805,697 B1 | 10/2004 | Helm et al. |
| 6,821,277 B2 | 11/2004 | Teitelbaum |
| 6,830,571 B2 | 12/2004 | Lenke et al. |
| 6,875,211 B2 | 4/2005 | Nichols et al. |
| 6,884,243 B2 | 4/2005 | Sellers |
| 6,899,716 B2 | 5/2005 | Cragg |
| 6,921,403 B2 | 7/2005 | Cragg et al. |
| 6,945,975 B2 | 9/2005 | Dalton et al. |
| 7,008,422 B2 | 3/2006 | Foley et al. |
| 7,011,658 B2 | 3/2006 | Young |
| 7,011,660 B2 | 3/2006 | Sherman et al. |
| 7,014,633 B2 | 3/2006 | Cragg |
| 7,060,066 B2 | 6/2006 | Zhao et al. |
| 7,087,058 B2 | 8/2006 | Cragg |
| 7,118,579 B2 | 10/2006 | Michelson |
| 7,118,580 B1 | 10/2006 | Beyersdorff et al. |
| 7,153,281 B2 | 12/2006 | Holmes |
| 7,160,300 B2 | 1/2007 | Jackson |
| 7,232,463 B2 | 6/2007 | Falahee |
| 7,338,527 B2 | 3/2008 | Blatt et al. |
| 7,455,685 B2 | 11/2008 | Justis |
| 7,465,306 B2 * | 12/2008 | Pond et al. .................. 606/86 A |
| 7,572,276 B2 | 8/2009 | Lim et al. |
| 7,585,316 B2 | 9/2009 | Trieu |
| 7,914,558 B2 * | 3/2011 | Landry et al. ................. 606/246 |
| 8,197,522 B2 * | 6/2012 | Park et al. ..................... 606/305 |
| 8,425,602 B2 * | 4/2013 | Guyer et al. ............... 623/17.11 |
| 8,512,343 B2 * | 8/2013 | Dziedzic et al. ............. 606/86 A |
| 2001/0012938 A1 | 8/2001 | Zucherman et al. |
| 2001/0021850 A1 | 9/2001 | Zucherman et al. |
| 2001/0031965 A1 | 10/2001 | Zucherman et al. |
| 2002/0016595 A1 | 2/2002 | Michelson |
| 2002/0045904 A1 * | 4/2002 | Fuss et al. ....................... 606/99 |
| 2002/0049444 A1 | 4/2002 | Knox |
| 2002/0055741 A1 | 5/2002 | Schlapfer et al. |
| 2002/0099386 A1 | 7/2002 | Beger et al. |
| 2002/0143328 A1 | 10/2002 | Shluzas et al. |
| 2002/0161368 A1 | 10/2002 | Foley et al. |
| 2002/0165612 A1 * | 11/2002 | Gerber et al. .............. 623/17.11 |
| 2002/0183755 A1 | 12/2002 | Michelson et al. |
| 2002/0188296 A1 | 12/2002 | Michelson |
| 2003/0018389 A1 | 1/2003 | Castro et al. |
| 2003/0040746 A1 | 2/2003 | Mitchell et al. |
| 2003/0060826 A1 | 3/2003 | Foley et al. |
| 2003/0074005 A1 | 4/2003 | Roth et al. |
| 2003/0078583 A1 | 4/2003 | Biedermann et al. |
| 2003/0153913 A1 | 8/2003 | Altarac |
| 2003/0187436 A1 | 10/2003 | Bolger et al. |
| 2003/0229347 A1 | 12/2003 | Sherman et al. |
| 2003/0236472 A1 | 12/2003 | Van Hoeck et al. |
| 2004/0012938 A1 | 1/2004 | Sylvester et al. |
| 2004/0018228 A1 | 1/2004 | Fischell et al. |
| 2004/0030346 A1 | 2/2004 | Frey et al. |
| 2004/0044412 A1 | 3/2004 | Lambrecht et al. |
| 2004/0073216 A1 | 4/2004 | Lieberman |
| 2004/0133207 A1 | 7/2004 | Abdou |
| 2004/0138671 A1 | 7/2004 | Zander et al. |
| 2004/0153070 A1 | 8/2004 | Barker et al. |
| 2004/0167625 A1 | 8/2004 | Beyar et al. |
| 2004/0204712 A1 | 10/2004 | Kolb et al. |
| 2004/0204713 A1 | 10/2004 | Abdou |
| 2005/0004573 A1 | 1/2005 | Abdou |
| 2005/0010227 A1 | 1/2005 | Paul |
| 2005/0021029 A1 | 1/2005 | Trieu et al. |
| 2005/0021031 A1 | 1/2005 | Foley et al. |
| 2005/0021040 A1 | 1/2005 | Bertagnoli |
| 2005/0055031 A1 | 3/2005 | Lim et al. |
| 2005/0085813 A1 | 4/2005 | Spitler et al. |
| 2005/0119747 A1 | 6/2005 | Fabris et al. |
| 2005/0126576 A1 | 6/2005 | Ferree |
| 2005/0131406 A1 | 6/2005 | Reiley et al. |
| 2005/0131421 A1 | 6/2005 | Anderson et al. |
| 2005/0154389 A1 | 7/2005 | Selover et al. |

(56) References Cited

U.S. PATENT DOCUMENTS

| | | |
|---|---|---|
| 2005/0165398 A1 | 7/2005 | Reiley |
| 2005/0171540 A1 | 8/2005 | Lim et al. |
| 2005/0177163 A1 | 8/2005 | Abdou |
| 2005/0192589 A1* | 9/2005 | Raymond et al. ............... 606/99 |
| 2005/0197660 A1 | 9/2005 | Haid et al. |
| 2005/0203512 A1 | 9/2005 | Hawkins et al. |
| 2005/0203533 A1 | 9/2005 | Ferguson et al. |
| 2005/0203624 A1 | 9/2005 | Serhan |
| 2005/0209694 A1 | 9/2005 | Loeb |
| 2005/0215999 A1 | 9/2005 | Birkmeyer et al. |
| 2005/0234449 A1 | 10/2005 | Aferzon |
| 2005/0234451 A1 | 10/2005 | Markworth |
| 2005/0245928 A1 | 11/2005 | Colleran |
| 2005/0261768 A1 | 11/2005 | Trieu |
| 2005/0273120 A1 | 12/2005 | Abdou |
| 2005/0283153 A1 | 12/2005 | Polyner |
| 2005/0288669 A1 | 12/2005 | Abdou |
| 2006/0030839 A1* | 2/2006 | Park et al. ........................ 606/1 |
| 2006/0036255 A1* | 2/2006 | Pond et al. ...................... 606/86 |
| 2006/0052870 A1 | 3/2006 | Ferree |
| 2006/0074488 A1 | 4/2006 | Abdou |
| 2006/0084986 A1 | 4/2006 | Grinberg et al. |
| 2006/0084988 A1 | 4/2006 | Kim |
| 2006/0111728 A1 | 5/2006 | Abdou |
| 2006/0142761 A1 | 6/2006 | Landry et al. |
| 2006/0149238 A1 | 7/2006 | Sherman et al. |
| 2006/0149278 A1 | 7/2006 | Abdou |
| 2006/0167454 A1 | 7/2006 | Ludwig et al. |
| 2006/0184247 A1 | 8/2006 | Edidin et al. |
| 2006/0195102 A1 | 8/2006 | Malandain |
| 2006/0200135 A1 | 9/2006 | Sherman et al. |
| 2006/0217710 A1 | 9/2006 | Abdou |
| 2006/0229614 A1 | 10/2006 | Foley et al. |
| 2006/0229615 A1 | 10/2006 | Abdou |
| 2006/0235532 A1 | 10/2006 | Meunier et al. |
| 2006/0247630 A1 | 11/2006 | Lott et al. |
| 2006/0247634 A1 | 11/2006 | Warner et al. |
| 2006/0264942 A1 | 11/2006 | Lim et al. |
| 2006/0276803 A1 | 12/2006 | Salerni |
| 2007/0032790 A1 | 2/2007 | Aschmann et al. |
| 2007/0093828 A1 | 4/2007 | Abdou |
| 2007/0093829 A1 | 4/2007 | Abdou |
| 2007/0106383 A1 | 5/2007 | Abdou |
| 2007/0123884 A1 | 5/2007 | Abdou |
| 2007/0151116 A1 | 7/2007 | Malandain |
| 2007/0173831 A1 | 7/2007 | Abdou |
| 2007/0173842 A1 | 7/2007 | Abdou |
| 2007/0185367 A1 | 8/2007 | Abdou |
| 2007/0185489 A1 | 8/2007 | Abdou |
| 2007/0191958 A1 | 8/2007 | Abdou |
| 2007/0198090 A1 | 8/2007 | Abdou |
| 2007/0233083 A1 | 10/2007 | Abdou |
| 2007/0233251 A1 | 10/2007 | Abdou |
| 2007/0282448 A1 | 12/2007 | Abdou |
| 2008/0027438 A1 | 1/2008 | Abdou |
| 2008/0039843 A1 | 2/2008 | Abdou |
| 2008/0045963 A1 | 2/2008 | Abdou |
| 2008/0058810 A1 | 3/2008 | Abdou |
| 2008/0243186 A1 | 10/2008 | Abdou |
| 2008/0281358 A1 | 11/2008 | Abdon |
| 2008/0281359 A1 | 11/2008 | Abdou |
| 2010/0016906 A1 | 1/2010 | Abdou |
| 2010/0069929 A1 | 3/2010 | Abdou |
| 2010/0069965 A1 | 3/2010 | Abdou |
| 2010/0076448 A1 | 3/2010 | Abdou |
| 2010/0087858 A1 | 4/2010 | Abdou |
| 2010/0087869 A1 | 4/2010 | Abdou |
| 2010/0087878 A1 | 4/2010 | Abdou |
| 2010/0087923 A1 | 4/2010 | Abdou |
| 2010/0106250 A1 | 4/2010 | Abdou |
| 2010/0121384 A1 | 5/2010 | Abdou |

FOREIGN PATENT DOCUMENTS

| | | |
|---|---|---|
| EP | 0611116 | 8/1994 |
| EP | 1180348 | 2/2002 |
| EP | 1442715 | 8/2004 |
| FR | 2781359 | 1/2000 |
| FR | 2856271 | 12/2004 |
| WO | 2004/032726 | 4/2004 |
| WO | WO 2004/032726 | 4/2004 |
| WO | 2004/062482 | 7/2004 |
| WO | WO 2004/062482 | 7/2004 |
| WO | 2004/093702 | 11/2004 |
| WO | WO 2004/093702 | 11/2004 |
| WO | WO 2005/077288 | 8/2005 |
| WO | WO 2005/122922 | 12/2005 |
| WO | WO 2006/041963 | 4/2006 |
| WO | WO 2006/058221 | 6/2006 |
| WO | WO 2006/089292 | 8/2006 |
| WO | WO 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |
| WO | WO 2008/106140 | 2/2008 |

OTHER PUBLICATIONS

U.S. Appl. No. 11/739,053, filed Apr. 23, 2007.
U.S. Appl. No. 11/888,754, filed Aug. 1, 2007.
U.S. Appl. No. 12/690,824, filed Jan. 20, 2010.
U.S. Appl. No. 12/727,641, filed Mar. 19, 2010.
U.S. Appl. No. 12/758,531, filed Apr. 12, 2010.
U.S. Appl. No. 12/767,573, filed Apr. 26, 2010.
U.S. Appl. No. 12/779,839, filed May 13, 2010.
U.S. Appl. No. 12/789,435, filed May 27, 2010.
U.S. Appl. No. 12/790,754, filed May 28, 2010.
U.S. Appl. No. 12/790,713, filed May 28, 2010.
Derwent English Abstract for French Patent Publication FR 2781359, published Jan. 28, 2000, entitled: "Osteosynthesis frame for spinal surgery has rod with clamps to hold cross bars with anchor screws". Accession No. 9867555.
Derwent English Abstract for French Patent Publication FR 2856271, published Dec. 24, 2004, Osteo-synthesis vertebral column plate, has connection head integrated with plate and movable in three directions of space so as to adapt itself to connection rod, and including opening to facilitate introduction of rod. Accession No. 14694557.

* cited by examiner

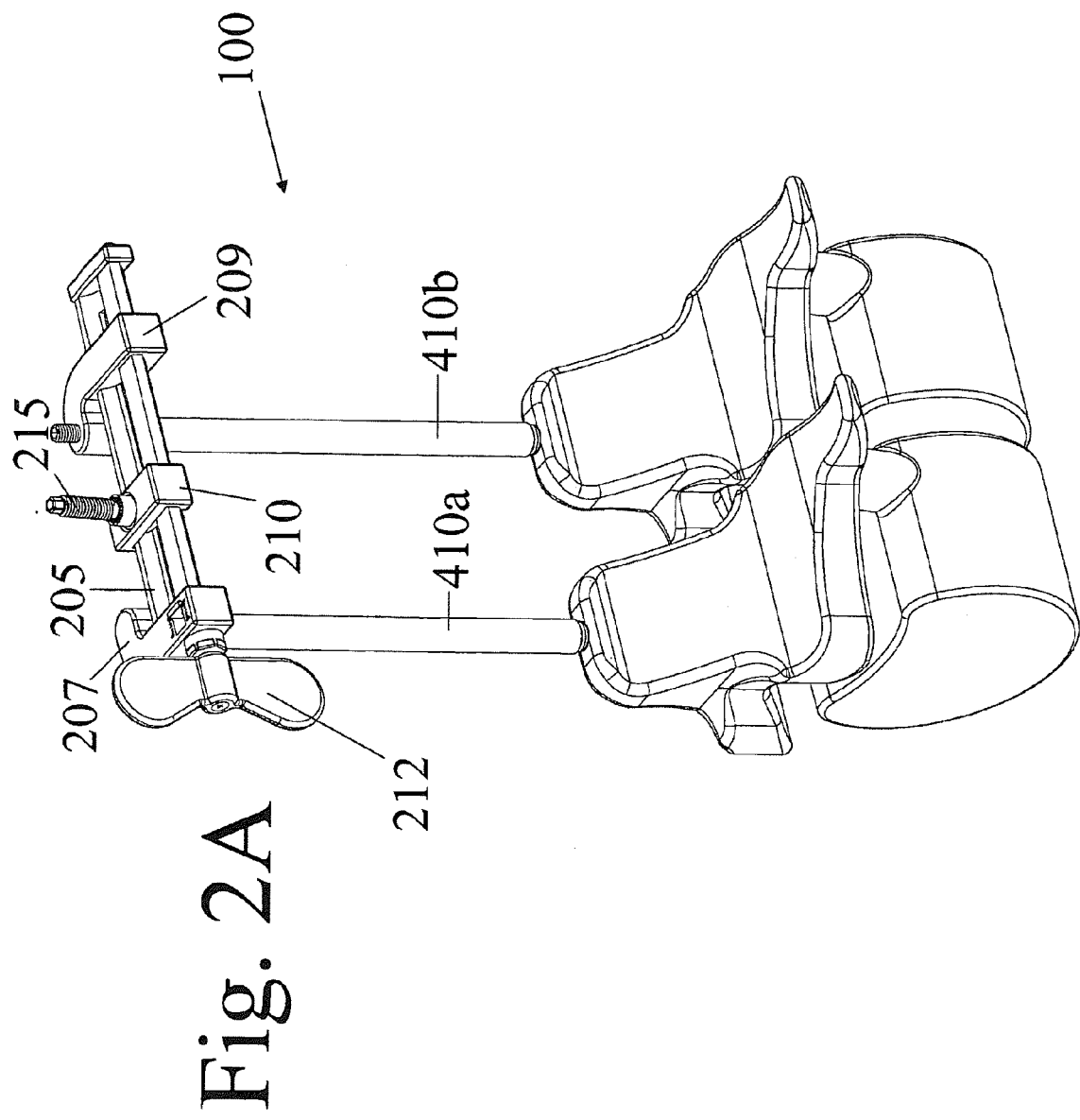

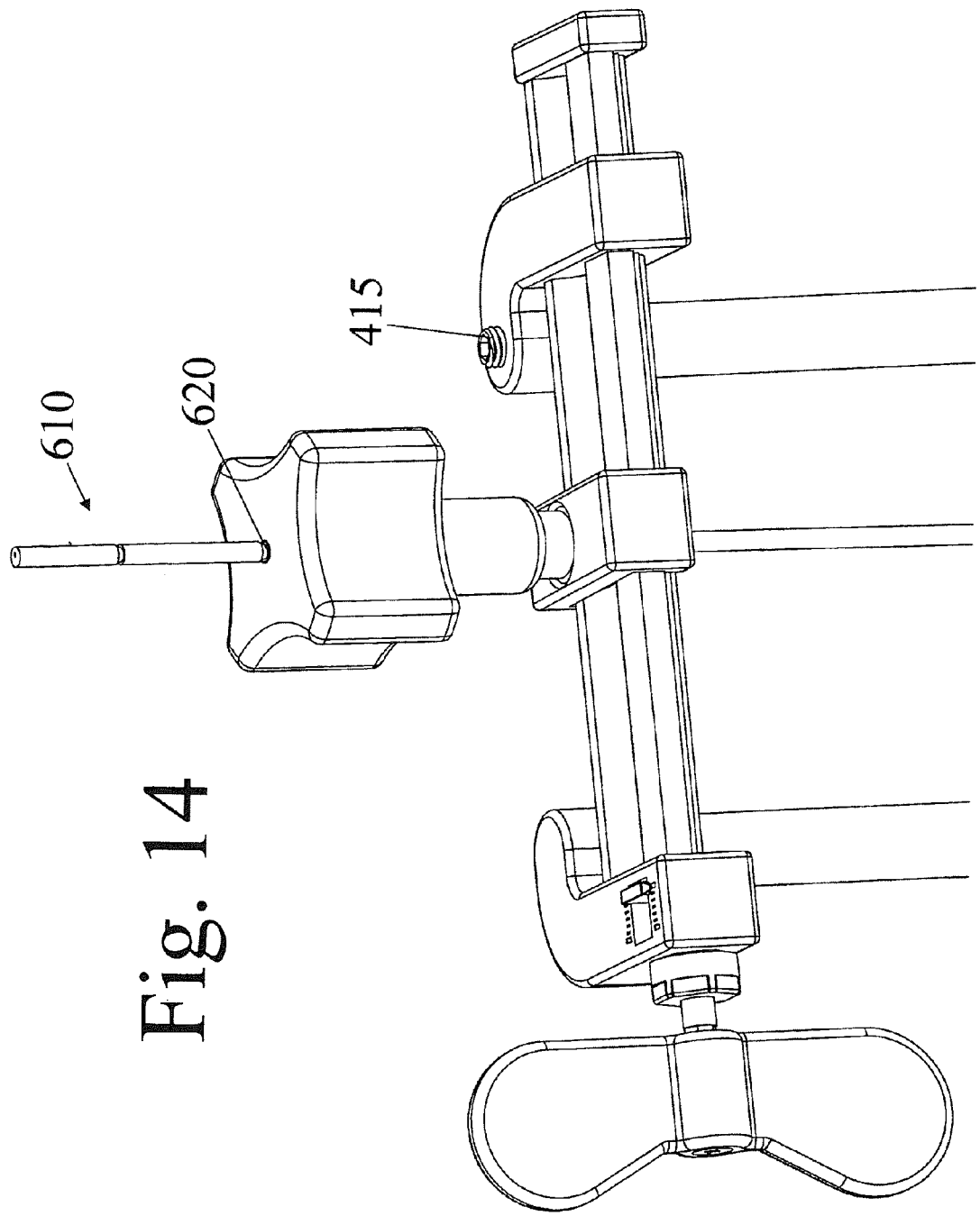

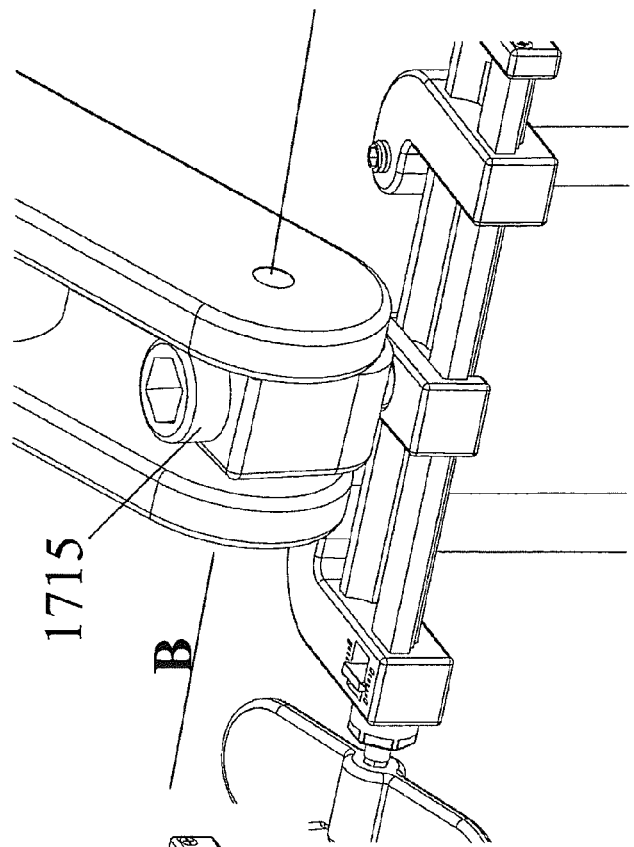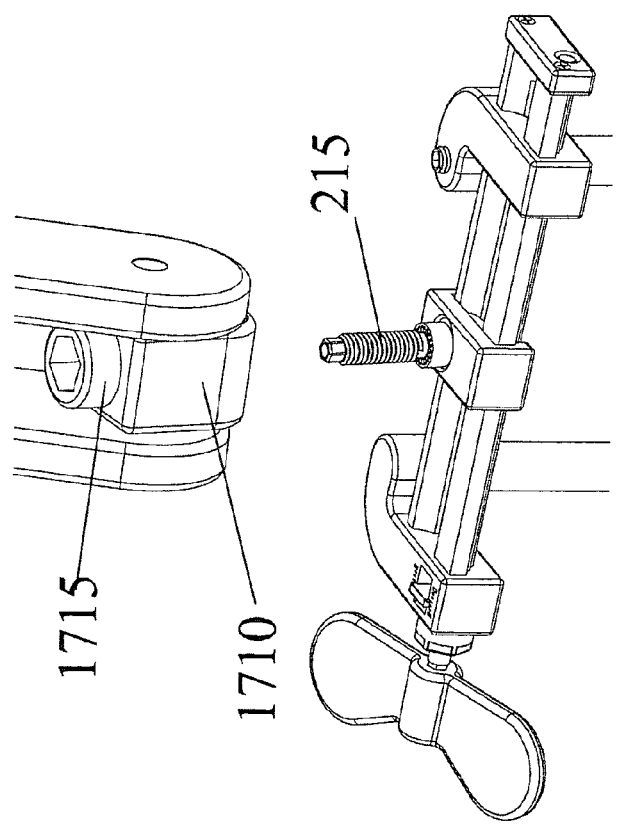

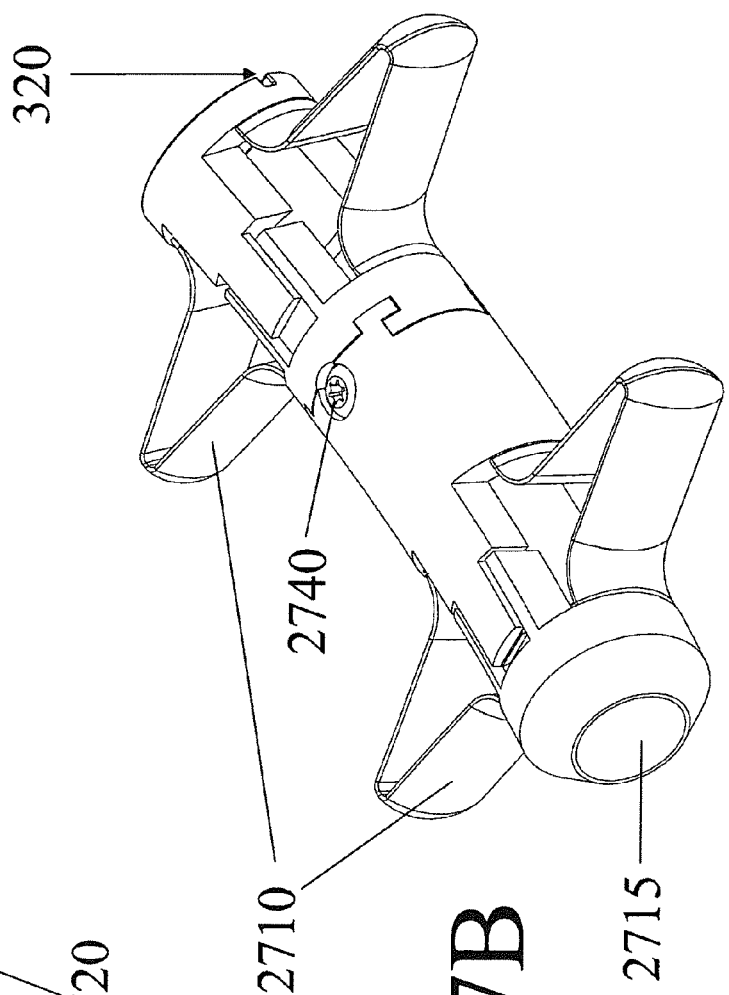
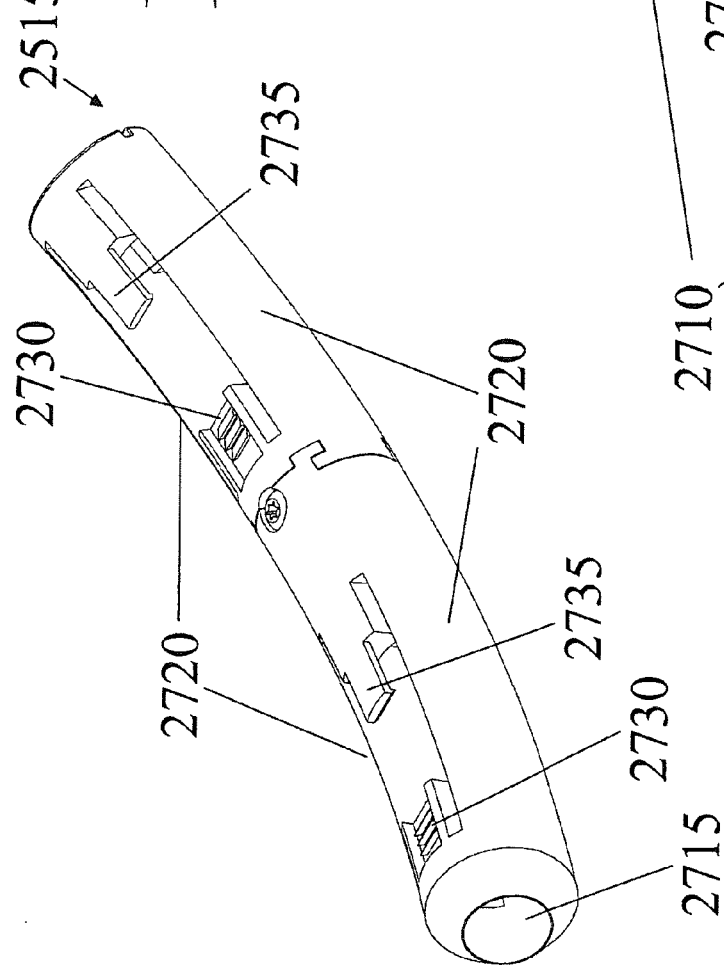

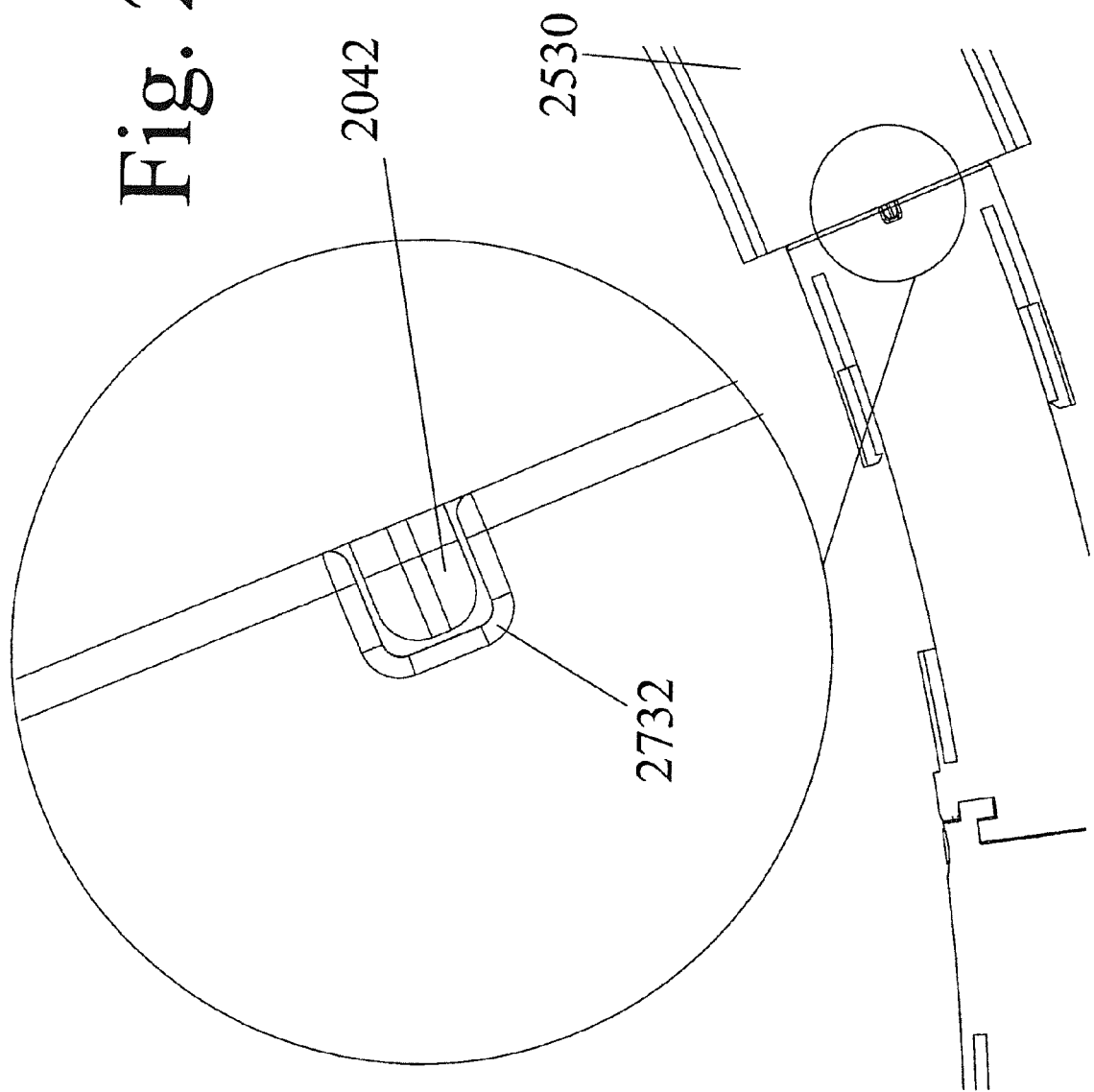

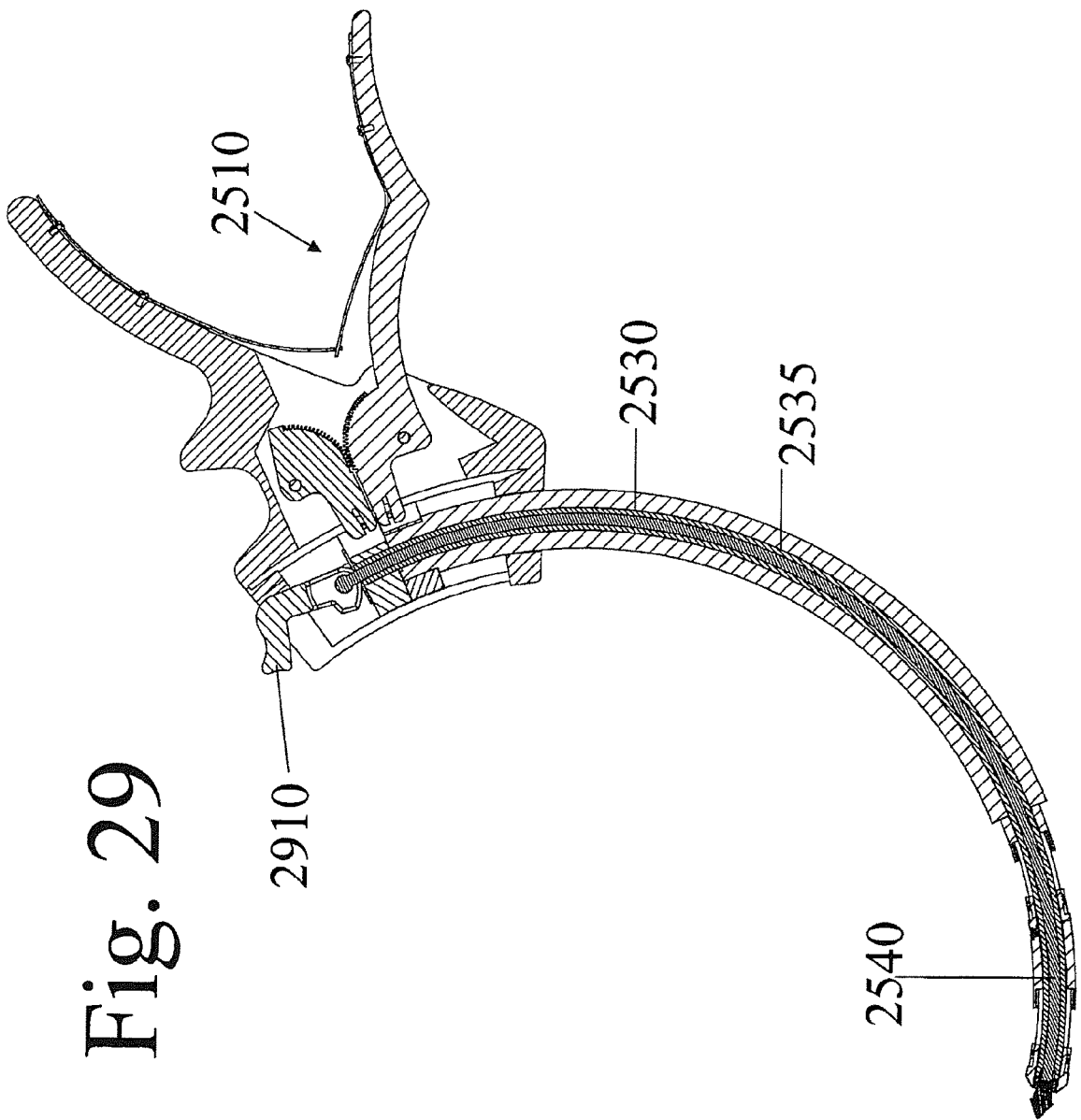

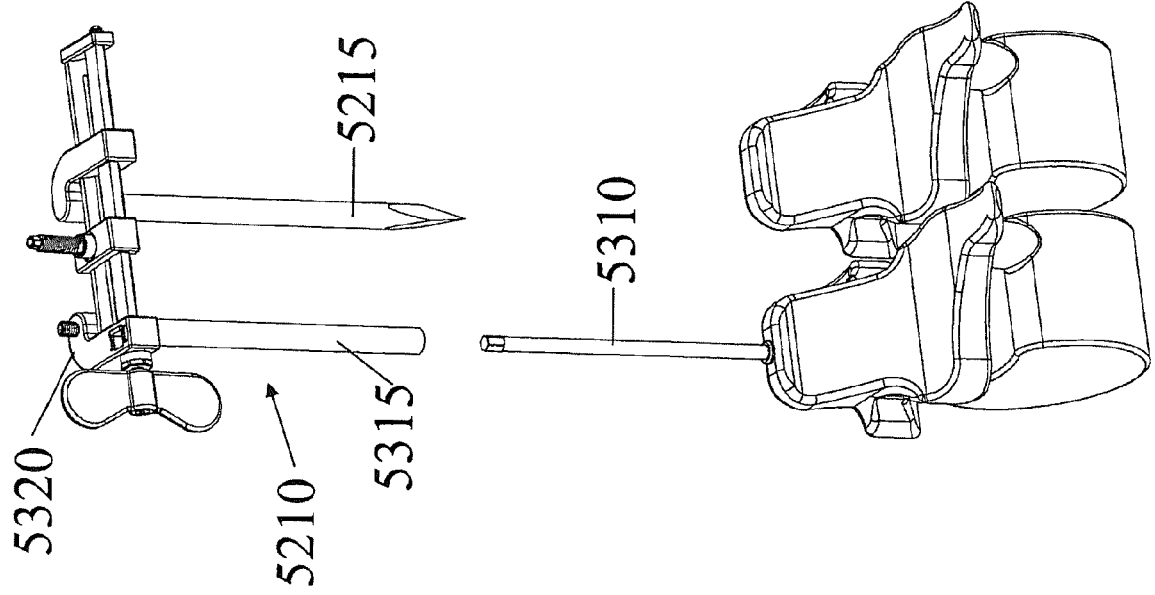

DEVICES AND METHODS FOR INTER-VERTEBRAL ORTHOPEDIC DEVICE PLACEMENT

REFERENCE TO PRIORITY DOCUMENT

This application is a continuation of and claims priority of U.S. patent application Ser. No. 11/286,152, issued as U.S. Pat. No. 8,172,855 on May 8, 2012 which claims priority to U.S. Provisional Patent Application Ser. No. 60/631,213, filed Nov. 24, 2004 and U.S. Provisional Patent Application Ser. No. 60/713,235, filed Aug. 31, 2005. Priority of the aforementioned filing dates is hereby claimed, and the disclosures of the Provisional Patent Applications are hereby incorporated by reference in their entirety.

BACKGROUND

The disclosure relates to devices and methods for implantation of an orthopedic device between skeletal segments using limited surgical dissection. The implanted devices are used to adjust and maintain the spatial relationship(s) of adjacent bones. Depending on the implant design, the motion between the skeletal segments may be increased, limited, modified, or completely immobilized.

Progressive constriction of the central canal within the spinal column is a predictable consequence of aging. As the spinal canal narrows, the nerve elements that reside within it become progressively more crowded. Eventually, the canal dimensions become sufficiently small so as to significantly compress the nerve elements and produce pain, weakness, sensory changes, clumsiness and other manifestation of nervous system dysfunction.

Constriction of the canal within the lumbar spine is termed lumbar stenosis. This condition is very common in the elderly and causes a significant proportion of the low back pain, lower extremity pain, lower extremity weakness, limitation of mobility and the high disability rates that afflict this age group. The traditional treatment for this condition has been the surgical removal of the bone and ligamentous structures that constrict the spinal canal. Despite advances in surgical technique, spinal decompression surgery can be an extensive operation with risks of complication from the actual surgical procedure and the general anesthetic that is required to perform it. Since many of these elderly patients are in frail health, the risk of developing significant peri-operative medical problems remains high. In addition, the traditional treatment of surgical resection of spinal structures may relieve the neural compression but lead to spinal instability in a substantial minority of patients. That is, removal of the spinal elements that compress the nerves may cause the spinal elements themselves to move in an abnormal fashion relative to one another and produce pain. Should it develop, instability would require additional and even more extensive surgery in order to re-establish spinal stability. Because of these and other issues, elderly patients with lumbar stenosis must often choose between living the remaining years in significant pain or enduring the potential life-threatening complications of open spinal decompression surgery.

Recently, lumbar stenosis has been treated by the distraction—instead of resection—of those tissues that compress the spinal canal. In this approach, an implantable device is placed between the spinous processes of the vertebral bodies at the stenotic level in order to limit the extent of bone contact during spinal extension. Since encroachment upon the nerve elements occurs most commonly and severely in extension, this treatment strategy produces an effective increase in the size of the spinal canal by limiting the amount of spinal extension. In effect, distraction of the spinous processes changes the local bony anatomy and decompresses the nerves by placing the distracted spinal segment into slight flexion.

A number of devices that utilize this strategy have been disclosed. U.S. Pat. Nos. 6,451,020; 6,695,842; 5,609,634; 5,645,599; 6,451,019; 6,761,720; 6,332,882; 6,419,676; 6,514,256; 6,699,246 and other illustrate various spinous process distractors. Unfortunately, the placement of each device requires exposure of the spinous processes and the posterior aspect of the spinal column. Thus, these operations still present a significant risk of pen-operative complications in this frail patient population.

It would be desirable to design an improved method for the placement of an orthopedic device between the spinous processes of adjacent spinal segments. A workable method of percutaneous delivery would reduce the surgical risks of these procedures and significantly increase the usefulness of these spinous process distractors. This application discloses a device for the percutaneous placement of inter-spinous process implants. The method of use provides a reliable approach that maximizes the likelihood of optimal device placement and obviates the need for open surgery.

SUMMARY

Disclosed are devices and methods that can accurately place an orthopedic device between adjacent spinous processes. The devices and methods employs a percutaneous approach and constitutes the least invasive method of delivery system yet devised. Also disclosed are various instruments for implant placement and the implant itself.

Pursuant to a procedure, a patient is placed on his side or in the prone position. The hips and knees are flexed and the procedure is performed under x-ray guidance. The level of interest is identified radiographically and bone screws are percutaneously inserted into the spinous processes of the upper and lower vertebras of the stenotic level. A distractor is placed onto the two screws and a needle is placed through the distractor platform and guided into the space between the spinous processes under X-ray guidance. The tip of the needle is guided into the exact position where the implant needs to be placed. The needle is marked so that the distance from the needle tip to the center of rotation of the insertion device (discussed below) can be measured. The platform is then immobilized relative to the rest of the distractor and the spinous processes of the stenotic level are gently distracted. In order to gauge the extent of distraction and better standardize the procedure, a measure of the force of distraction is displayed by the distraction device. The localizing needle is rerrioved.

A curvilinear device is attached to the platform. The device has a guide arm that rotates about a central point so as to form an arc. Since the distance from the guide arm's center of rotation to the tip of the localizing needle is known, a guide arm of radius equal to that distance will necessarily form an arc that contains the needle point on its circumference. A trocar with a knife-like tip is placed through the central channel in order to divide tissue before the advancing guide arm. The guide arm is them rotated through the skin and underlying tissue until the distal end of the guide arm abuts the side of the ligament between the spinous processes at the stenotic level. Using this method, a curvilinear path is created to the point marked by the needle tip in a completely percutaneous manner and without any open surgical tissue dissection.

The trocar is removed from the guide arm's central canal. The central canal is then used to deliver the implant to the desired point between. the spinous processes. Alternatively, a solid guide arm may be used with the implant attached to the tip.

The placement system described herein provides an easy and reliable way of placing an orthopedic device within the inter-spinous ligament. Using this method, the implant can be placed rapidly, precisely, with a few small skin incisions and the absolute minimum amount of tissue dissection. It permits minimally invasive device placement using only local anesthesia into those afflicted patients who are least able to withstand the stress of open surgical intervention.

In one aspect, there is disclosed a distractor instrument, comprising: a first distractor member that engages at a distal end to a first skeletal segment; a second distractor member that engages at a distal to a second skeletal segment; a distractor device mounted to proximal ends of the first and second distractor members; and a distraction actuator attached to the distractor device, wherein the distraction actuator is actuated to apply a distraction force to the first and second distractor members to distract the first and second skeletal segments relative to one another.

In another aspect, there is disclosed a distractor instrument, comprising first and second distraction members that each engage a respective skeletal segment, wherein the distraction members can be distracted to cause distraction of the skeletal segments.

In another aspect, there is disclosed a method of distracting a pair of spinous processes, comprising using one or more distractor elements to engage the spinous processes to apply a distraction force to the spinous processes.

In another aspect, there is disclosed a minimally-invasive surgical procedure, comprising localizing a surgical point of interest using a localizing needle that points to the point of interest; and placing an implant at the point of interest using the localizing needle as a guide.

In another aspect, there is disclosed a minimally-invasive surgical procedure, comprising localizing a surgical point of interest using an x-ray to identify the point of interest; relating the point of interest to a delivery apparatus; and delivering an implant to the point of interest using an inserter device that pivots about a central axis such that the inserter device travels along a curvilinear path that contains the localized point of interest.

In another aspect, there is disclosed a skeletal implant holder, comprising a hand-operated handle assembly; and a holder assembly attached to the handle assembly. The holder assembly is configured to be removably attached to an implant, wherein the handle assembly can be actuated to secure the implant to the holder assembly and to detach the implant from the holder assembly, and wherein the holder assembly is configured to apply a first force to the implant in a first direction and a second force to the implant in a second direction opposite the first direction when the handle assembly is actuated.

In another aspect, there is disclosed an implant for implanting between a pair of skeletal segments, comprising a first segment; at least one wing attached to the first segment, the wing movable between a collapsed configuration and an expanded configuration wherein the wing can engage a skeletal segment as an anchor when in the expanded configuration; and a second segment removably attached to the first segment, wherein the second segment can be detached from the first segment to disengage the wing from the skeletal segment.

These and other features will become more apparent from the following description and the accompanying drawings.

BRIEF DESCRIPTION OF THE DRAWINGS

FIG. 2A shows a perspective view of the device with an insertion device detached.

FIG. 14 shows the platform with the locking mechanism and localizing needle coupled thereto.

FIGS. 17A and 17B show enlarged views of the attachment member of the insertion device being lowered onto the attachment screw of the platform.

FIGS. 27A and 27B show the implant with extendable wings in an undeployed (FIG. 27A) and a deployed state (FIG. 27B).

FIG. 28 shows an enlarged view of a portion of the implant coupled to the holder device.

FIG. 29 shows a cross-sectional view of the implant attached to the holder.

FIG. 53 shows another perspective view of the distractor device of FIG. 52.

DETAILED DESCRIPTION

Disclosed are methods and devices for implanting a device (such as an orthopedic device) between skeletal segments (such as vertebrae), using limited surgical dissection. The implanted devices are used to adjust and maintain the spatial relationship(s) of adjacent bones.

Figure 1:
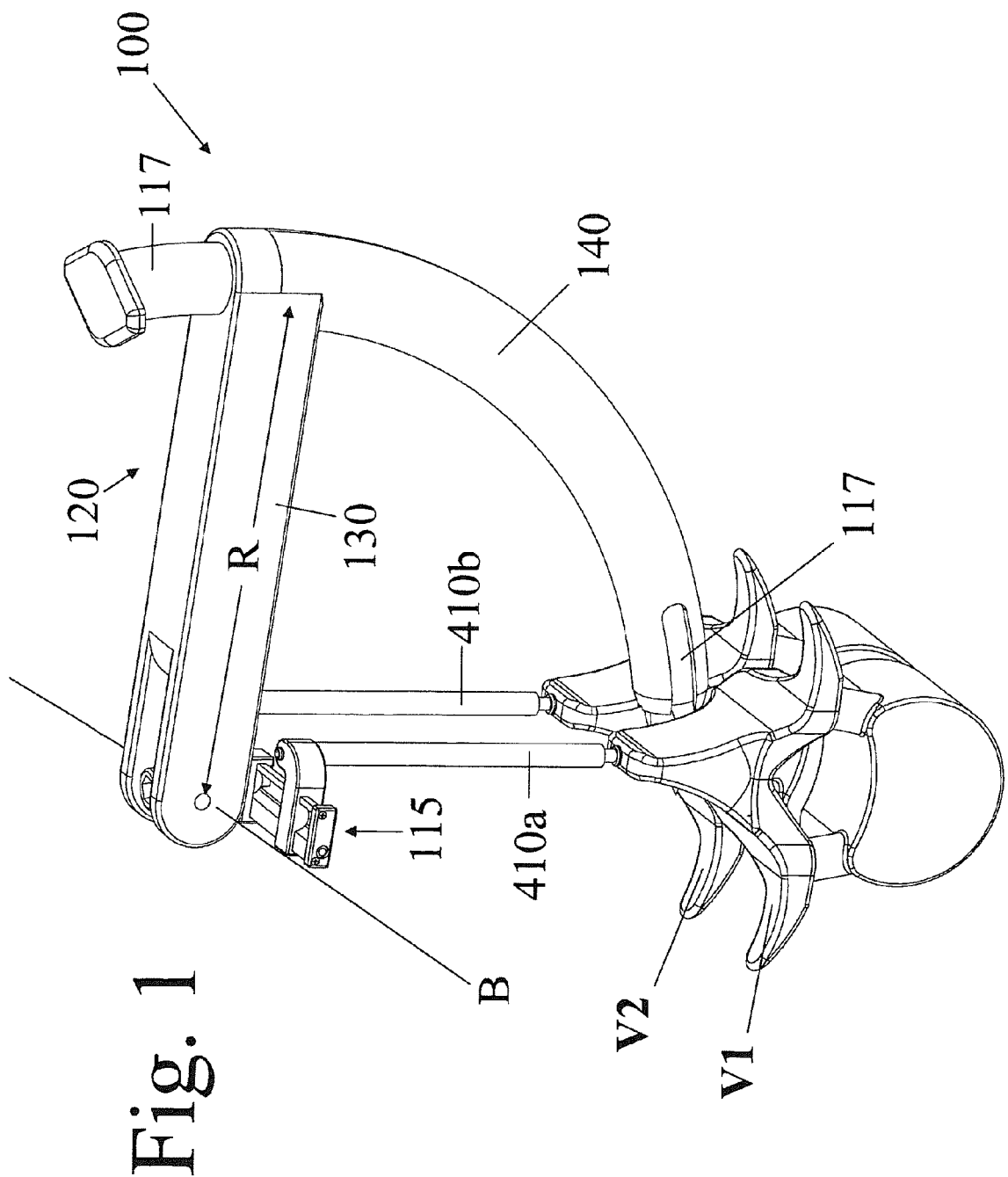
FIG. 1 shows a perspective, assembled view of a distractor device 100 for implanting an orthopedic device between skeletal segments, such as between a first vertebral body V1 and a second vertebral body V2.

FIG. 1 shows a perspective, assembled view of a distractor device 100 for implanting an orthopedic device between skeletal segments, such as between a first vertebral body V1 and a second vertebral body V2. For clarity of illustration, the vertebral bodies are represented schematically and those skilled in the art will appreciate that actual vertebral bodies include anatomical details not shown in FIG. 1. Moreover, although described in the context of being used with vertebrae, it should be appreciated the device 100 and associated methods can also be used with other skeletal segments.

The device 100 generally includes a pair of anchors that include elongate distraction screws 110a and 110b (collectively screws 110), a platform 115, and an insertion device 120 that is pivotably attached to the platform 115 via an attachment member. A curvilinear trocar 117 is removably mounted in a hollow shaft of the insertion device 120. Each of the distraction screws 110 is attached at a distal end to a respective vertebral body. In this regard, the distal end of each screw can include a structure for attaching to the vertebral body, such as a threaded shank. The proximal ends of the distraction screws 110 are attached to the platform 115. The screws 110 are axially positioned within sheaths that surround the screws and extend downwardly from the platform 115, as described below with reference to FIGS. 3-4.

The insertion device 120 is pivotably attached to the platform 115 such that the insertion device 120 can pivot about an axis B. The insertion device 120 includes a connecting arm 130 that extends outwardly from the platform 115, and a curved portion 140 that curves toward the vertebral bodies from an outward tip of arm 130. Arm 130 has a length R that corresponds to a radius of curvature of the curved portion 140. Thus, when the insertion device 120 pivots about the axis B, the curved member 140 moves along a curved or arced pathway of radius R. The curved portion 140 can include an internal guide shaft that extends through the curved portion 140 along the entire length of the curved portion 140. The guide shaft is sized and shaped to slidably receive the trocar 117. The radius of curvature of the curved portion 140 can vary. As described in detail below, the curved portion 140 acts as a guide for guiding an implant device to a position between the vertebral bodies FIG. 2A shows a perspective view of the device 100 with the insertion device 120 detached. The platform 115 includes a rail 205 that extends between the screws 110 along a direction generally parallel to the axis of the spine. As mentioned, each screw 110 extends upwardly from a respective vertebral body and attaches at a proximal end to the platform 115. The screw 110a attaches to a member 207 that is fixedly attached to the rail 205. The screw 100b attaches to a member 209 that is slidably attached to the rail 205. A distraction actuator, such as a thumb screw 212, can be actuated (such as rotated) to distract the screws 110 (and the attached vertebral bodies) relative to one another, as described below.

Figure 2B:
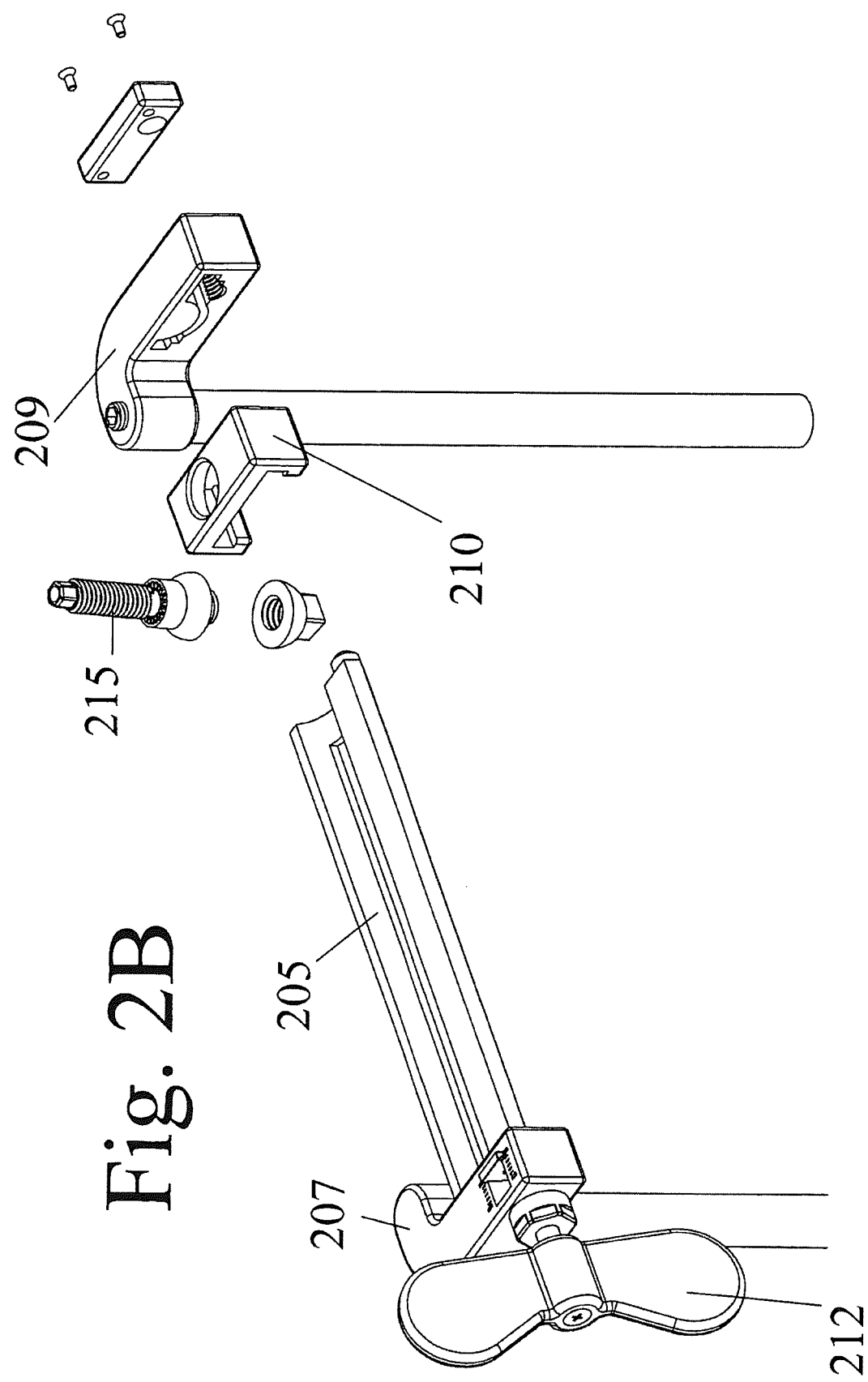
FIG. 2B shows an exploded view of a platform of the device.

With reference still to FIG. 2A, a mount 210 is slidably attached to the platform 115 such that the mount 210 can slide along the length of the rail 205, although the position of the mount 210 can be locked relative to the platform 115, as described below. The mount 210 includes a hollow-shafted attachment screw 215 that can be used to removably attach the insertion device 120 to the platform 115. The attachment screw 215 can also be used to attach a localizing needle (described below) to the device 100. FIG. 2B shows an exploded view of the platform 115.

Figure 3:
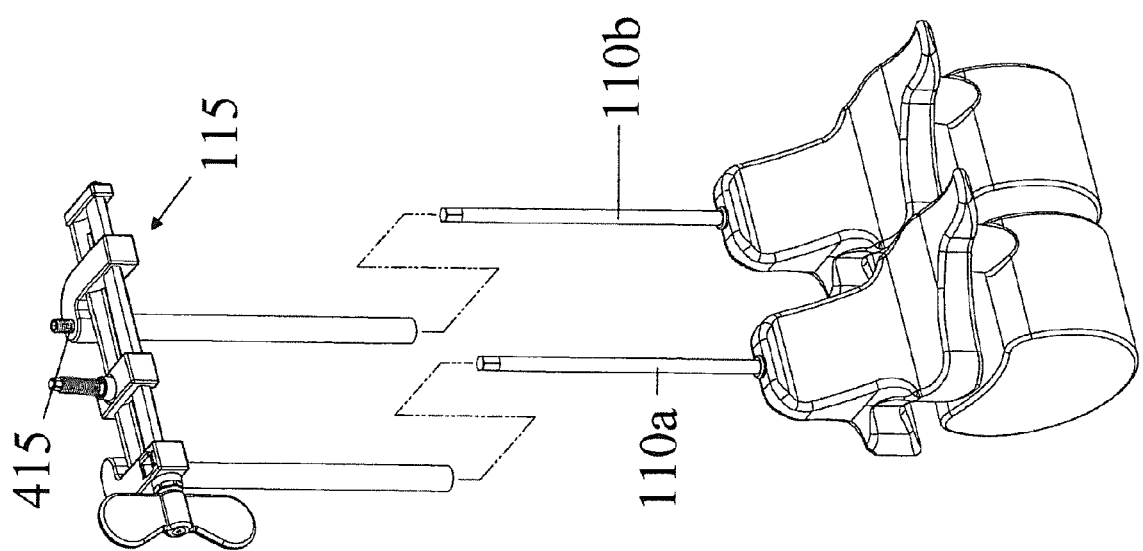
FIG. 3 shows a perspective view of the device with the platform removed.
Figure 4:
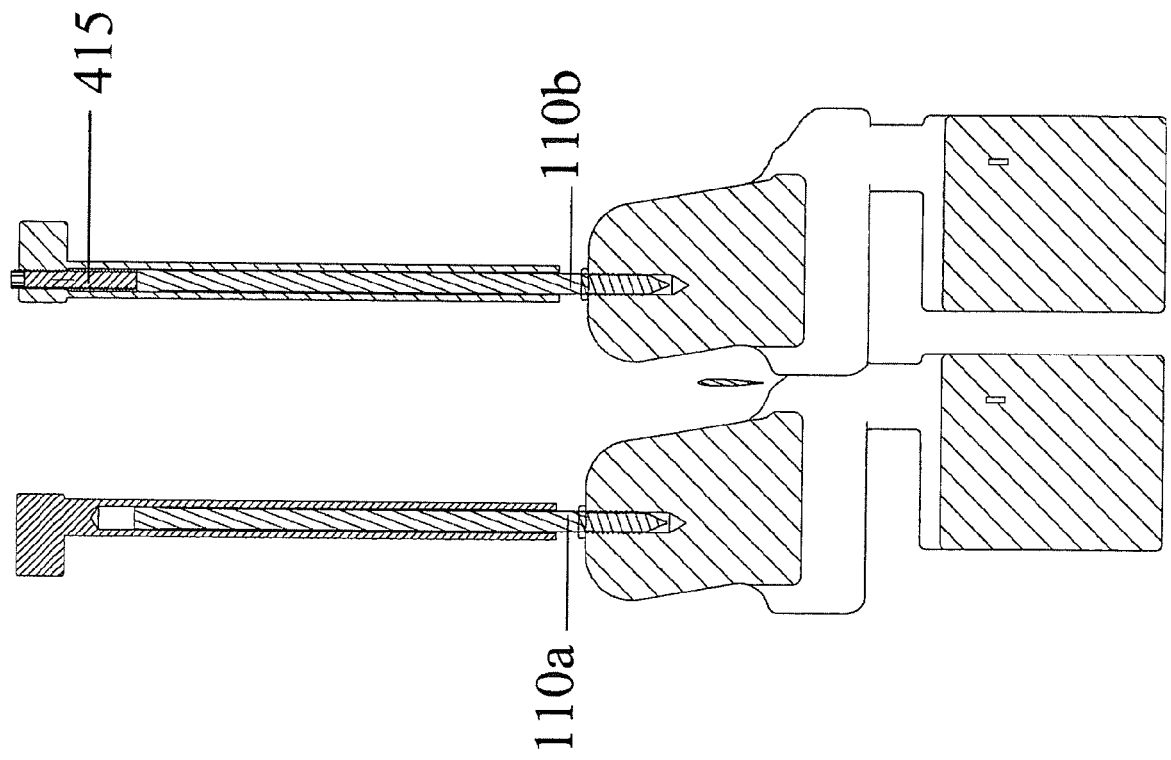
FIG. 4 shows a cross-sectional view of sheaths with screws positioned therein.

FIG. 3 shows a perspective view of the device 100 with the platform 115 removed from the screws 110. As mentioned above, the screws 110a and 110b are axially positioned within corresponding sheaths 410a and 410b, respectively. FIG. 4 shows a cross-sectional view of the sheaths 410 with the screws 110 positioned therein. For clarity of illustration, the platform 115 is not shown in. FIG. 4. Each sheath 410 has a hollow, internal shaft that is sized to slidably receive a respective screw 110. The internal shaft of the sheath 410a terminates at an upward end while the internal shaft of the sheath 410b extends entirely through the sheath 410 to form a hole in the upper end of the sheath 410b.

With reference to FIGS. 3 and 4, a vertical adjustment actuator, such as a turn screw 415, is positioned in the shaft of the sheath 410b above the screw 110b. The vertical adjustment actuator is actuated to adjust the vertical position of the platform 115 relative to the vertebral bodies. It should be appreciated that use of terms such as vertical, upward, downward, etc, are with reference to the figures and are not intended to limit actual use.

Figure 5:
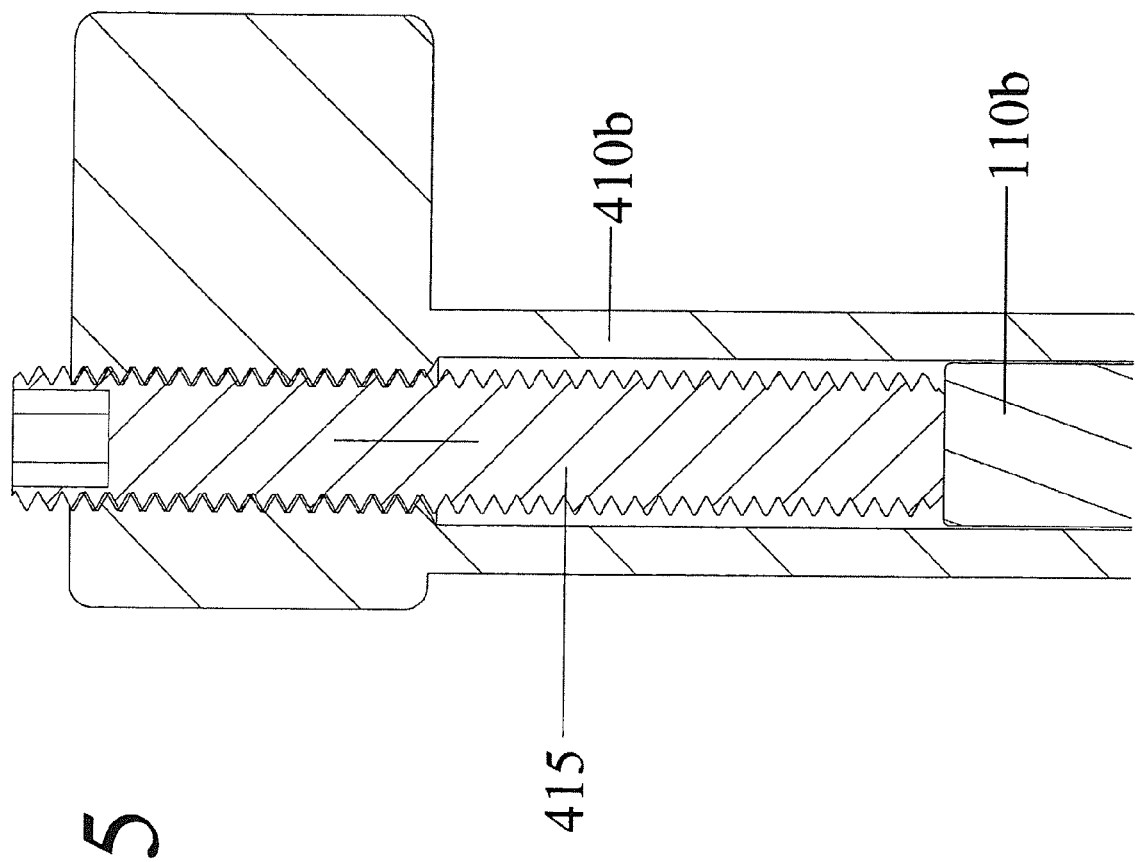
FIG. 5 shows an enlarged, cross-sectional view of the upper region of a sheath with a turn screw and a distraction screw a mounted therein.

An exemplary configuration for such vertical adjustment is now described. An upper region of the turn screw 415 protrudes upwardly out of the platform 1115, as best seen in FIG. 3. FIG. 5 shows an enlarged, cross-sectional view of the upper region of the sheath 410b with the turn screw 415 and distraction screw 110b mounted therein. The turn screw 415 has outer threads that mate with threads on the inner shaft of the sheath 410b. A lower edge of the turn screw 415 abuts an upper edge of the distraction screw 110b. When the turn screw 415 is rotated, the lower edge of the screw 415 moves downwardly or upwardly depending on the direction of rotation. The abutment of the turn screw 415 with the distraction screw 110b causes the sheath 410b (and the attached platform 115) to rise or drop relative to distraction screw 110b and the vertical bodies when the turn screw 415 is rotated. in this manner, the vertical position of the platform 415 can be adjusted by rotating the turn screw 415.

Figure 6:
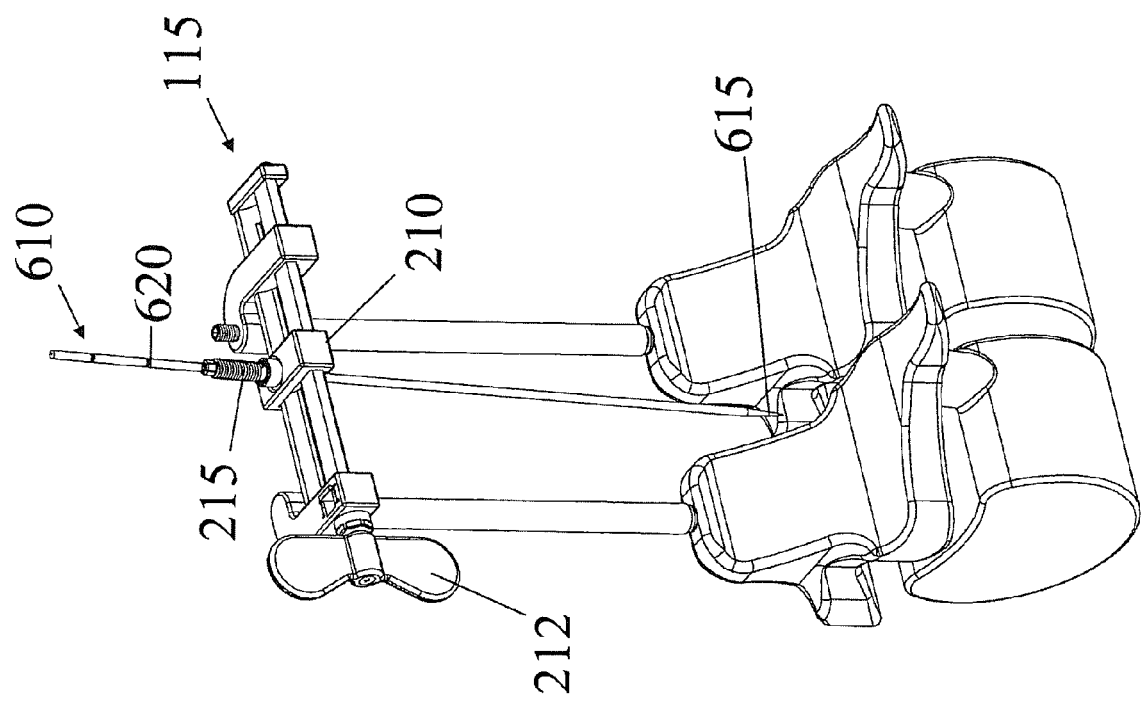
FIG. 6 shows a perspective view of the device with a localizing needle coupled thereto.

FIG. 6 shows a perspective view of the device 100 with a localizing needle 610 coupled thereto. As mentioned, the localizing needle 610 can be inserted through the attachment screw 215. The localizing needle 610 has a length such that a distal tip 615 of the needle 610 can be positioned at or substantially near a target location where an implant is to be placed. The localizing needle 610 includes one or more hatch markings 620. Each hatch marking 620 indicates the distance from the distal tip 615 of the localizing needle 610 to the hatch marking for purposes of selecting an appropriately-sized insertion device 120 for delivering an implant to the location identified by the distal tip 615, as described more fully below.

The localizing needle 610 can be locked or unlocked relative to the platform 115. When unlocked, the position and orientation of the localizing needle 610 can be adjusted relative to the platform 115. For example, the localizing needle 610 can rotate or pivot to adjust the orientation of the axis of the localizing needle 610. The localizing needle 610 can also slide relative to the rail 205 of the platform 115 by sliding the mount 210 and attachment screw 215 along the rail 205. When locked, the position and orientation of the localizing needle 610 relative to the platform 115 is fixed.

Figure 7:
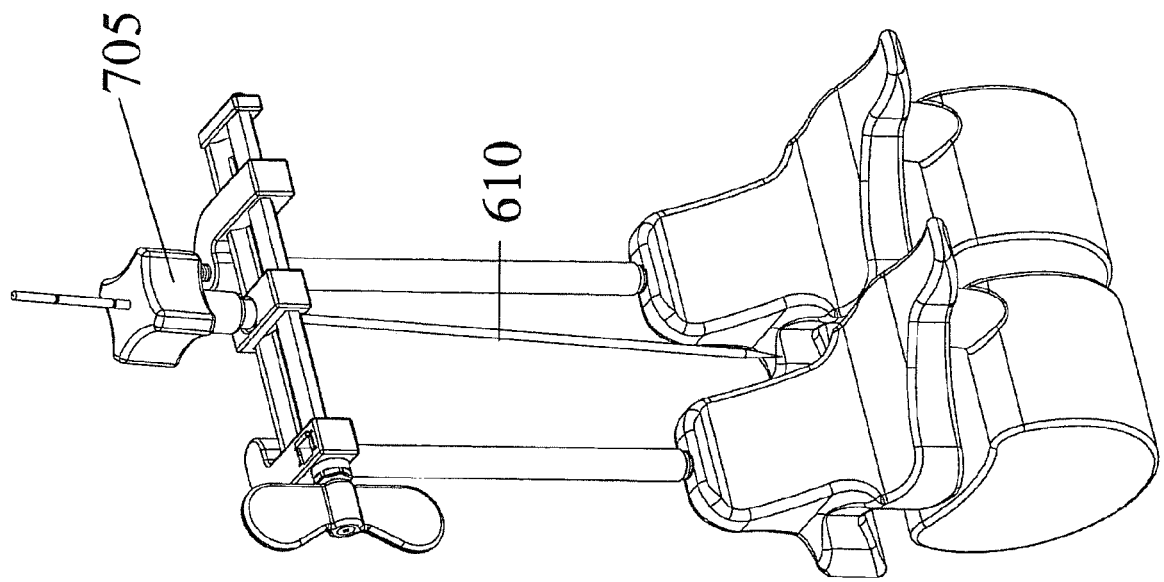
FIG. 7 shows a perspective view of the device with a locking instrument coupled to the platform for locking and unlocking the localizing needle.

FIG. 7 shows a perspective view of the device 100 with a locking instrument 705 coupled to the platform 115 for locking and unlocking the localizing needle. The locking instrument 705 is configured to tighten onto the attachment screw 215 (FIG. 6) for locking of the localizing needle 610. When the locking instrument tightens onto the attachment screw 215, the localizing needle locks.

Figure 8:
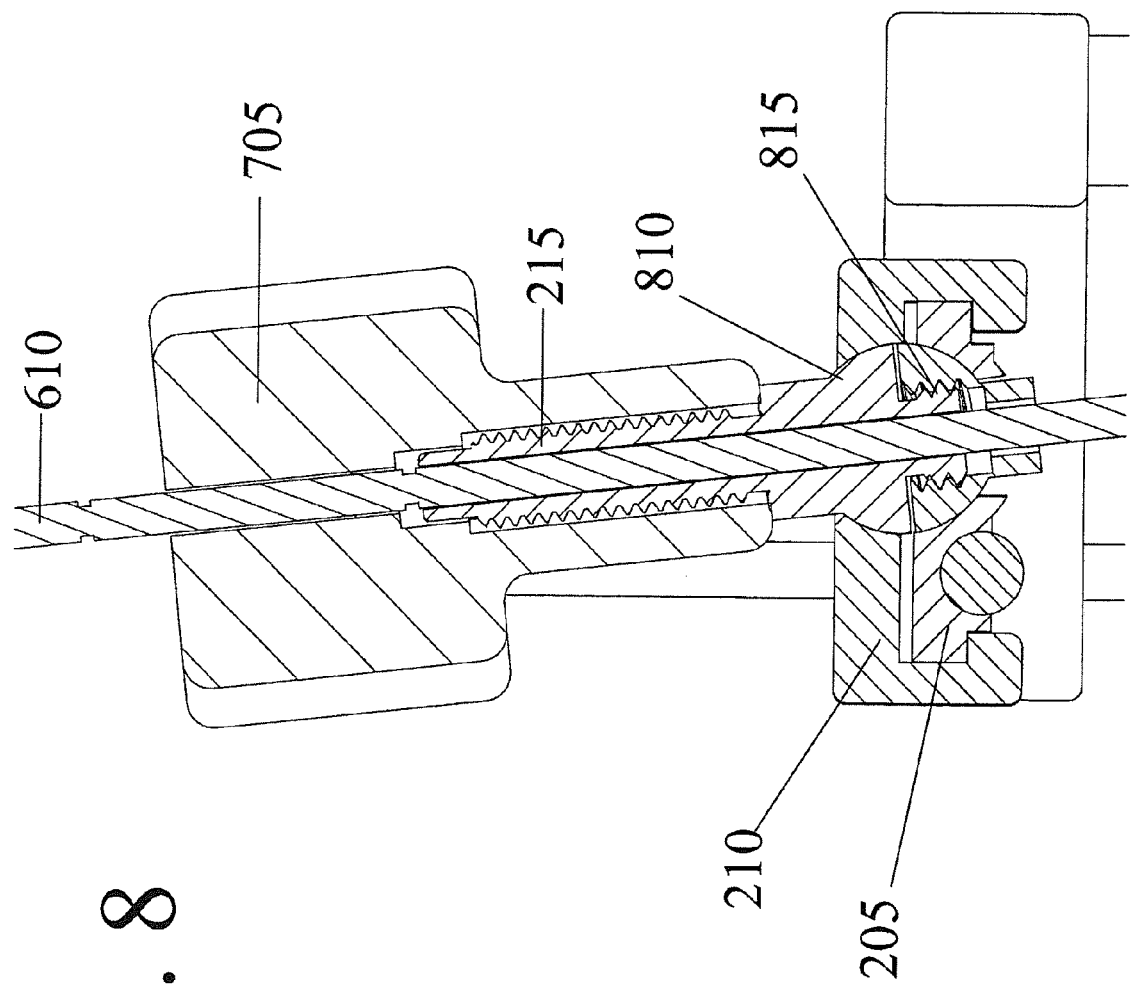
FIG. 8 shows a cross-sectional view of the locking instrument attached to the platform.

This is described in more detail with reference to FIG. 8, which shows a cross-sectional view of the locking instrument 705 attached to the platform 115 via threads that mate with threads on the locking screw 215. The locking screw 215 has an expandable, spherically-shaped head 810 that is positioned within a socket collectively formed by the mount 210 and the rail 205. When the locking instrument 705 is not tightened onto the attachment screw 215, the spherical head 810 is of a size that permits the head 810 to rotate within the socket. In addition, the mount 210 and attachment screw 215 can slide along the rail 205 when the locking instrument 705 is untightened.

However, when the locking instrument 705 is tightened, a threaded protrusion 815 causes the head 810 to expand within the socket. Specifically, the head 810 includes an upper half-sphere that contains a threaded protrusion 815, which engages a complimentary threaded bore within a lower half-sphere. The threads are arranged so that clockwise rotation of the upper half-sphere causes the two half-spheres to separate from one another. Since the two half-spheres are housed in an enclosed space, clock-wise rotation of the locking instrument causes the half-spheres to separate and become frictionally locked relative to the rail 205 and the mount 210. In this way, the mount 210 and attached needle 610 are locked in position relative to the platform 115.

Figure 9:
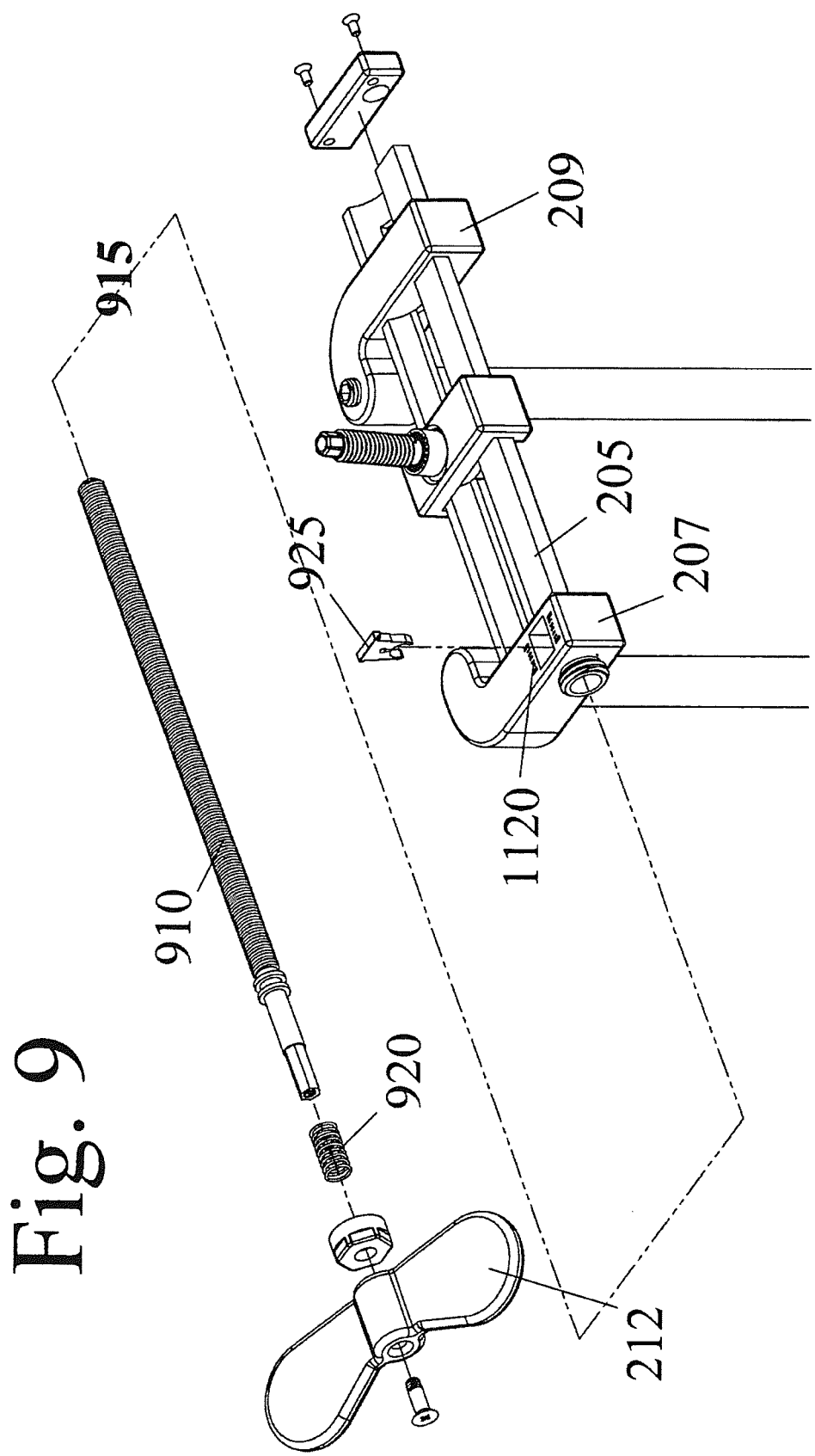
FIG. 9 shows a partial exploded view of the platform and shows an exemplary mechanism for effectuating distraction.

As mentioned above with reference to FIG. 2A, the device 100 includes a distraction actuator, such as a thumb screw 212, that is actuated (such as by being rotated) to distract the screws 110 (and the attached vertebral bodies) relative to one another. FIG. 9 shows a partial exploded view of the platform 115 and shows an exemplary mechanism for effectuating distraction. The thumb screw 212 attaches to an elongate, threaded lead screw 910 that can be axially inserted into one of the rails 205, as represented by the dashed line 915. A biasing member, such as a spring 920, mounts onto the lead screw 910. A pointer 925 also mounts onto the lead screw 910 for providing a measure of distraction force provided to vertebral bodies, as described more fully below. As mentioned, the member 207 is fixedly mounted to the rails 205, while the member 209 is slidably mounted on the rails 205.

Figure 10:
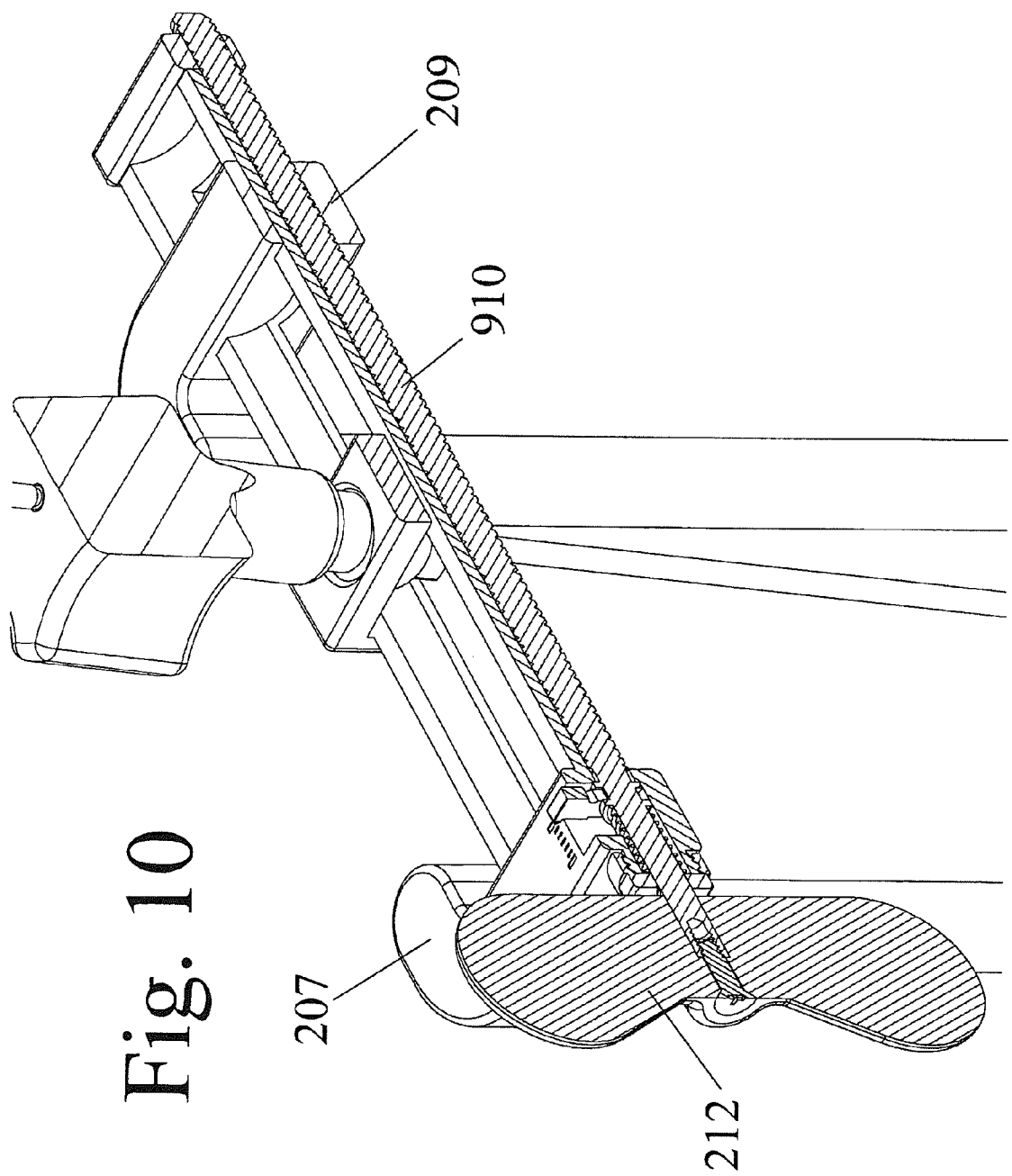
FIG. 10 shows a partial cross-sectional view of the platform in an assembled state.

FIG. 10 shows a partial cross-sectional view of the platform 115 in an assembled state. The lead screw 910 engages threads within the rail 205 and also engages threads within the slidable member 209. When the thumbscrew 212 is rotated, the attached lead screw 910 also rotates and moves inward or outward relative to the member 207, which causes the slidable member 209 to move toward or away from the member 207 depending on the direction of rotation. In this manner, the vertebral bodies, which are attached to the members 207, 209 via the distraction screws 110 (FIG. 2A) and the sheaths 410, can be distracted.

Figure 11:
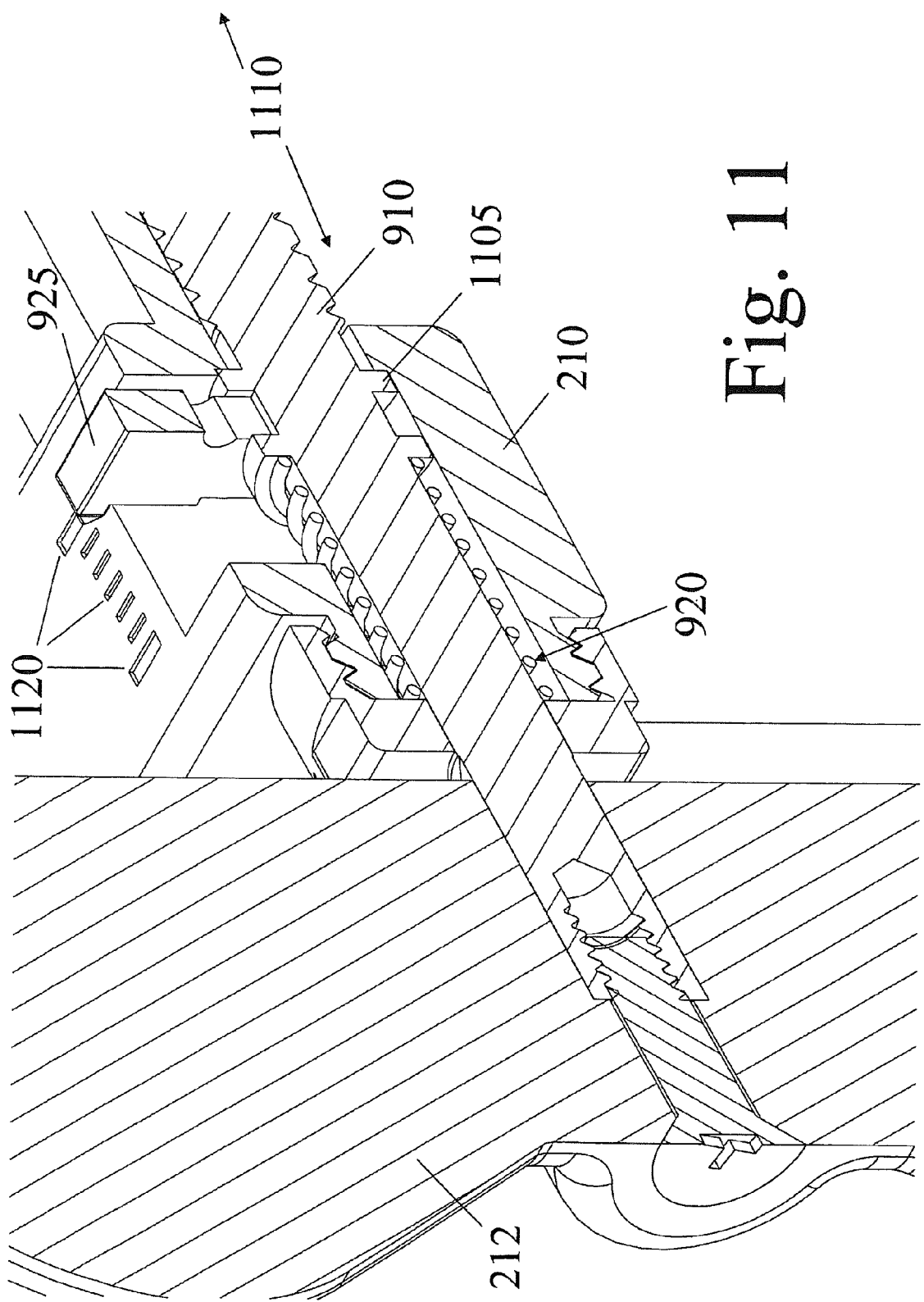
FIG. 11 shows an enlarged cross-sectional view of the platform in the region of a force pointer that provides a measure of distraction force provided to vertebral bodies.
Figure 12:
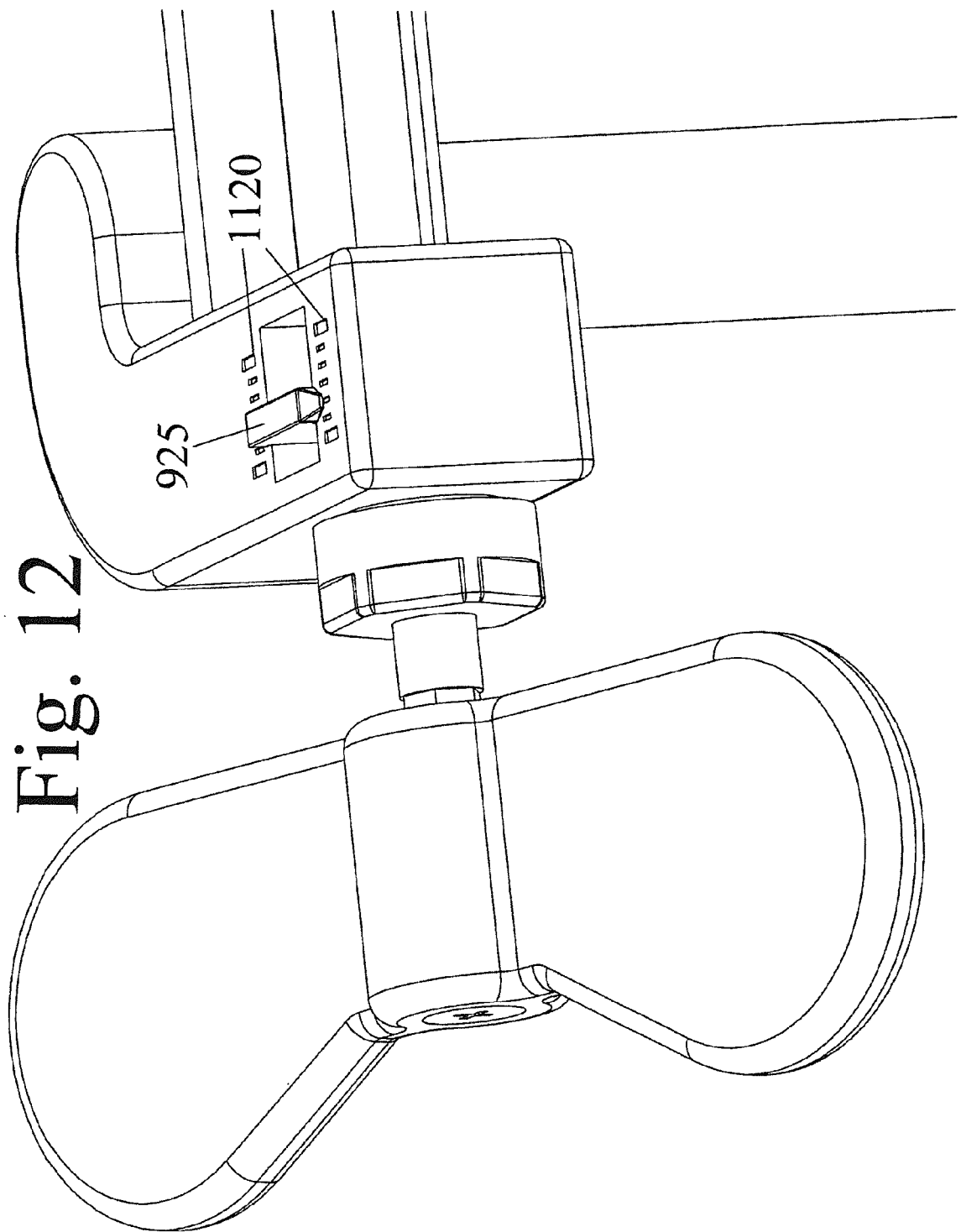
FIG. 12 shows an enlarged view of the pointer and corresponding markings on the platform.

FIG. 11 shows an enlarged cross-sectional view of the platform 115 in the region of the force pointer 910 that provides a measure of distraction force provided to vertebral bodies. The spring 920 is mounted on the lead screw 910 in between an internal wall of the member and a flange 1105 on the lead screw 910. As the lead screw 910 moves along the direction 1110 in response to rotation of the thumbscrew 212, the spring 920 compresses or expands depending on the direction of movement of the lead screw 910. As lead screw 910 turns and members 207 209 are moved apart, pointer 925 will move relative to marking 1120 in manner directly related to the force of distraction. That is, the pointer 925 moves with the lead screw 910 and moves relative to markings 1120 wherein the position of the pointer is proportional to the spring force of the spring 920 as the spring expands and contracts. In other words, as the distraction screws 110 and attached vertebral bodies are distracted, the pointer 925 moves relative to the markings 1120 to provide an indication as to force of distraction. The configuration of the hatch markings 1120 can vary. The hatch markings 126 may provide an actual measure of the distraction force in a recognized physical unit or simply give an arbitrary number, letter, or designation to which the operator would distract the vertebral bodies. FIG. 12 shows an enlarged view of the pointer 925 and the markings 1120 on the platform.

There is now described a method of use for the device 100. The patient is first placed in a position suitable for the procedure. For example, the patient is placed on his side or in the prone position. The hips and knees are flexed and the procedure is performed under x-ray guidance. The vertebral bodies at the diseased level(s) are identified radiographically and the bone screws 110 are percutaneously inserted into the spinous processes of the upper and lower vertebras. The device 100 is then coupled to the distraction screws 110 by sliding the sheaths 410 over the distraction screws, as shown in FIG. 3. For clarity of illustration, certain anatomical details, such as the patient's skin, are not shown in FIG. 3 and in some other figures.

As shown in FIG. 6, the localizing needle 610 is placed through the platform 115 and percutaneously guided into the inter-spinous space at the stenotic level. Under X-ray guidance, the needle's distal tip 615 is advanced until it lies where the operating surgeon wishes to place the implant. At this stage, the localizing needle 610 is in the unlocked state so that the surgeon can adjust the position and orientation of the needle. Once the surgeon has located the distal tip 615 so that it lies at a target location where the operating surgeon wishes to place the implant, the locking instrument 705 is locked onto the device, as shown in FIG. 7.

Figure 13:
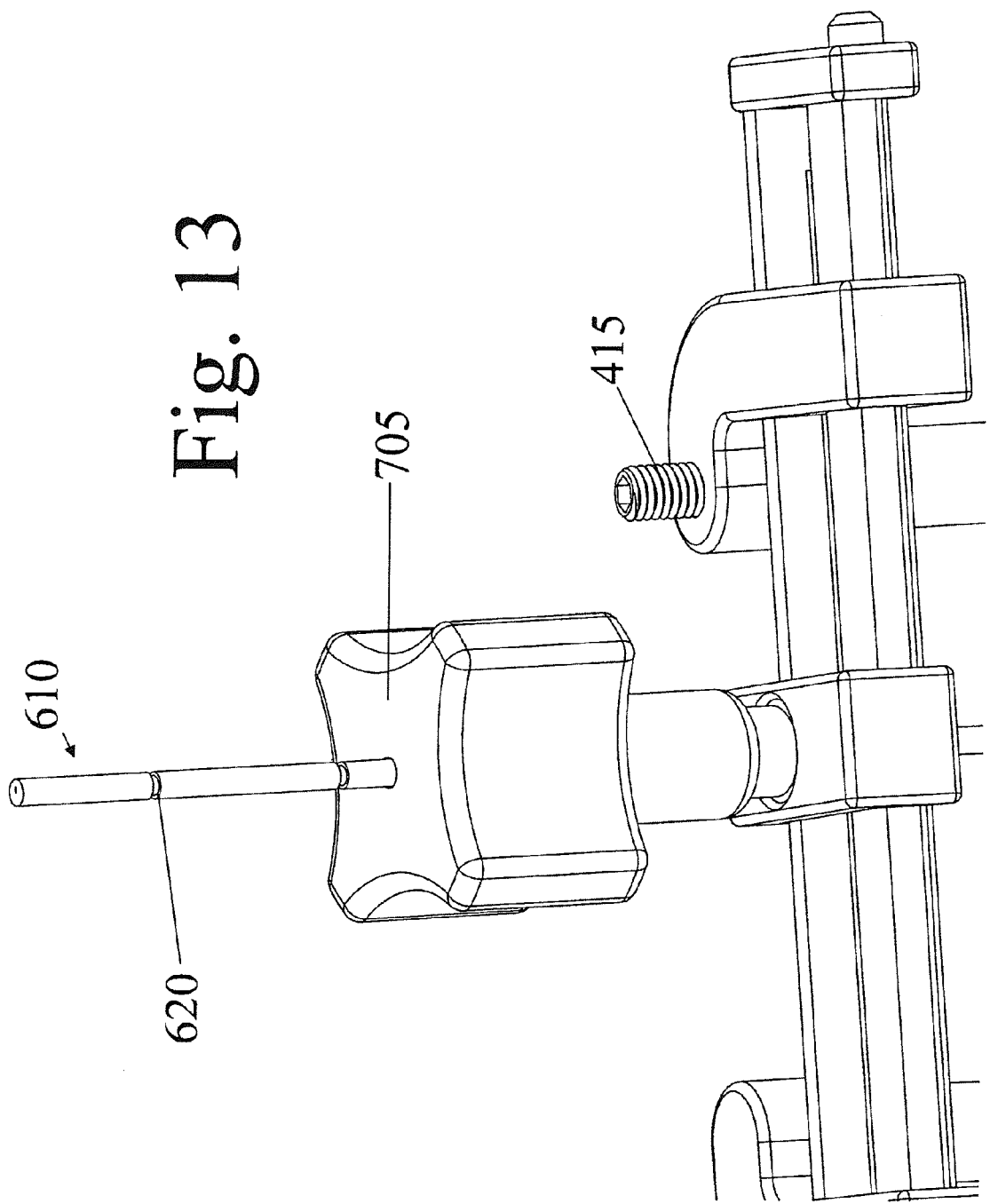
FIG. 13 shows an enlarged view of the locking mechanism and localizing needle.
Figure 15A:
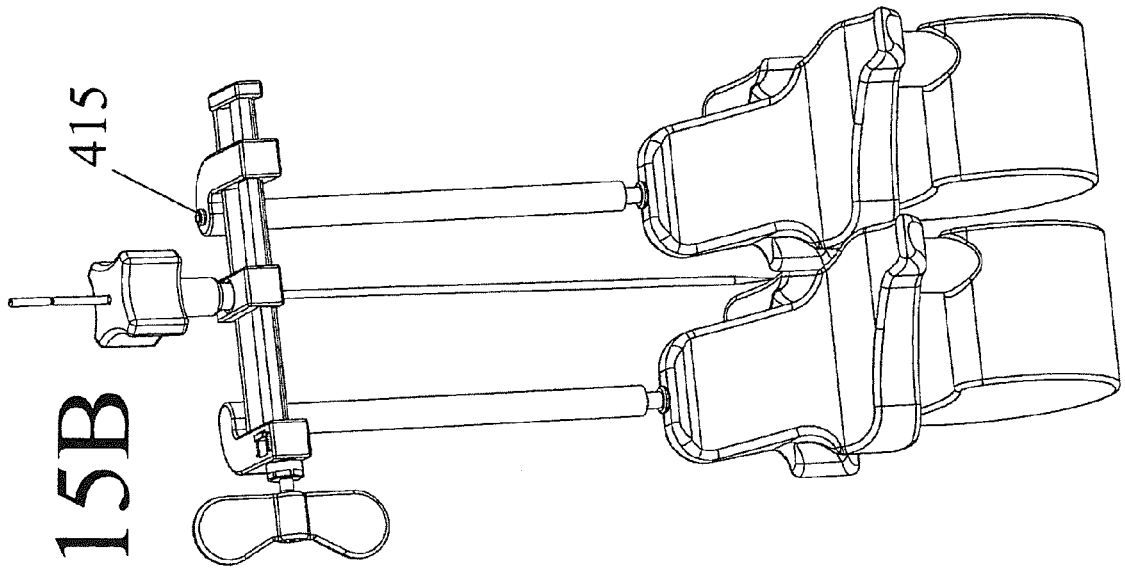
FIG. 15A shows the device with the platform positioned before it had been moved by a turn screw.
Figure 15B:
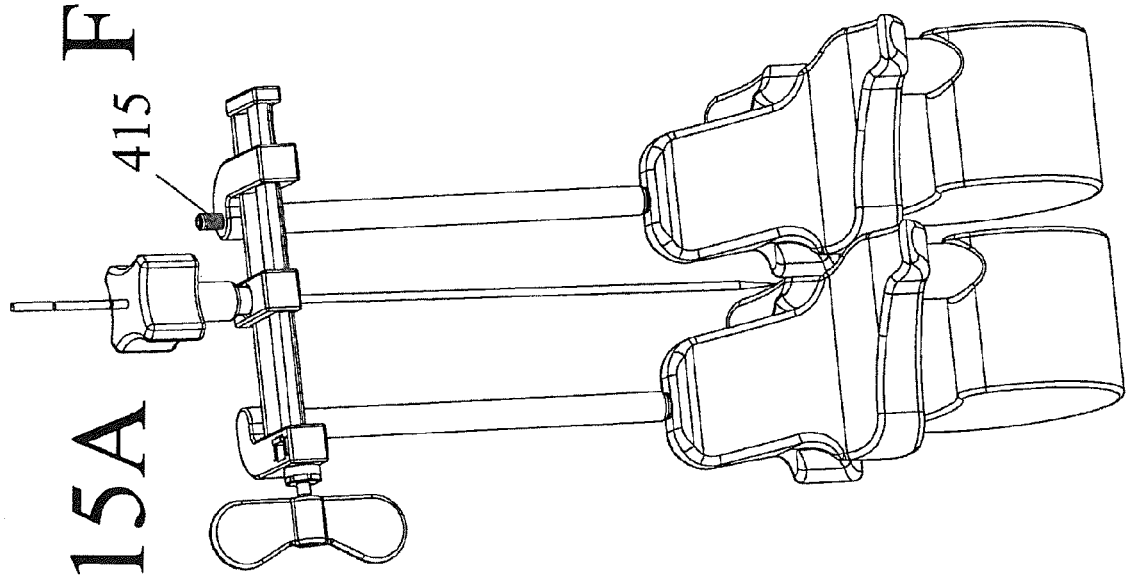
FIG. 15B shows the platform after movement.

As discussed and as shown in FIG. 13, the localizing needle 610 has one or more hatch markings 620 that indicate the distance from the distal tip 615 to the radial center of rotation of the guide arm. That distance can be illustrated at each hatch mark on the needle 610, although the distance is not shown in FIG. 13 for simplicity of illustration. After the needle's distal tip 615 is placed in the desired position, the position of the needle's hatch marks relative to the top of the locking instrument 705 is noted. The distractor device 100 is then moved upwards (or downward) by manipulating the turn screw 415 until the hatch mark immediately above the locking instrument 705 rests immediately adjacent the top of the instrument 705, as shown in FIG. 14. FIG. 15A shows the device with the platform 115 positioned before it had been moved by the turn screw 112 while FIG. 15B shows the platform 115 after movement. Note that the bottom portion of the distractor platform has displaced upward relative to the distraction bone screws.

At this stage of the procedure, the localizing needle 610 is locked in place with the marking 620 on the needle providing an indication as to the radius of rotation of the insertion member 120 to be mounted to the platform 115. With the needle and platform locked, the vertebral bodies are then distracted. This is accomplished by turning the thumb screw 212 which, in turn, moves the lead screw 910 and distracts the member 207 relative to the member 209 in the manner described above. As mentioned, the pointer 925 in combination with the markings 925 provide an actual measure of the distraction force in a recognized physical unit or provide an arbitrary number, letter, or designation to which the operator would distract the vertebral bodies.

At this stage of the procedure, the localizing needle 610 is fixed in place, the platform 115 is locked in position, and the vertebral bodies are distracted with the distraction force indicated by the pointer 925. A swing arm is selected with a radius R equivalent to the number, letter or designation of the hatch mark on the localizing needle 610 (the hatch mark 620 at the level of the top of locking instrument). Thus, when the insertion device 120 is pivoted about the axis B (FIG. 1), the curved portion 140 moves along a pathway that intersects the target location defined by the distal tip of the localizing needle 610.

Figure 16:
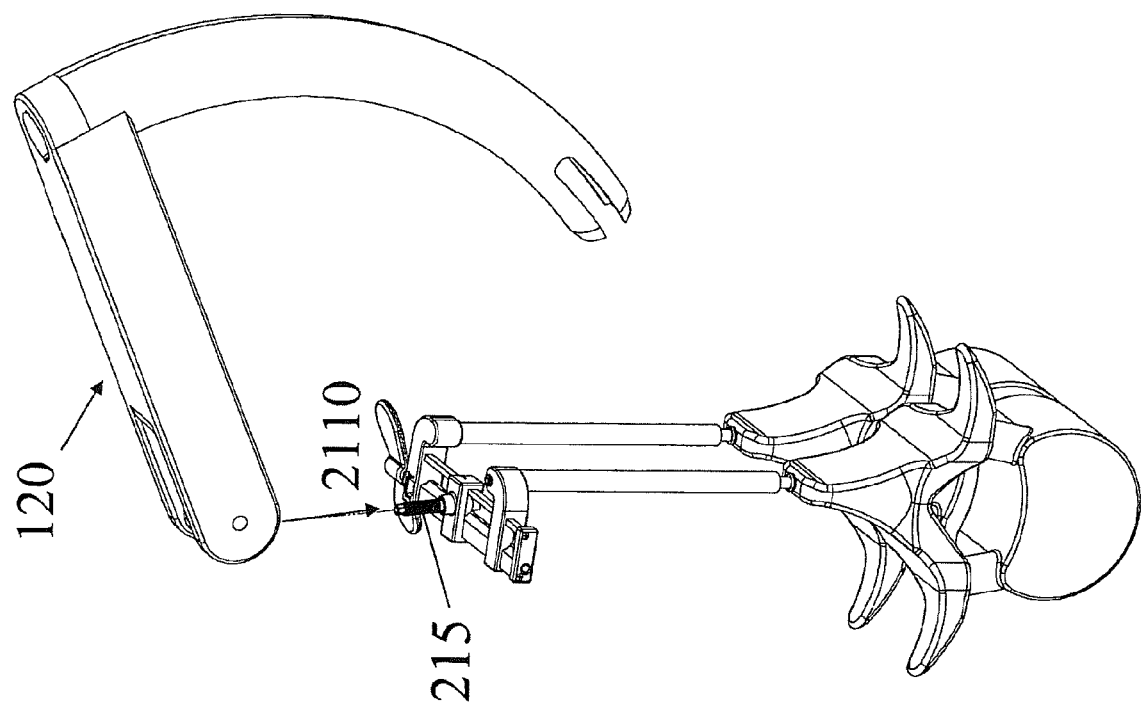
FIG. 16 is a perspective view of the device showing how the insertion device is pivotably attached to the platform.

FIG. 16 is a perspective view of the device showing how the insertion device 120 is pivotably attached to the platform 115. The insertion device 120 includes an attachment member 1710 (FIGS. 17A and 17B) that removably mates with the attachment screw 215 by lowering the attachment member 2210 onto the attachment screw 215, as represented by the arrow 2110 in FIG. 16.

Figure 18:
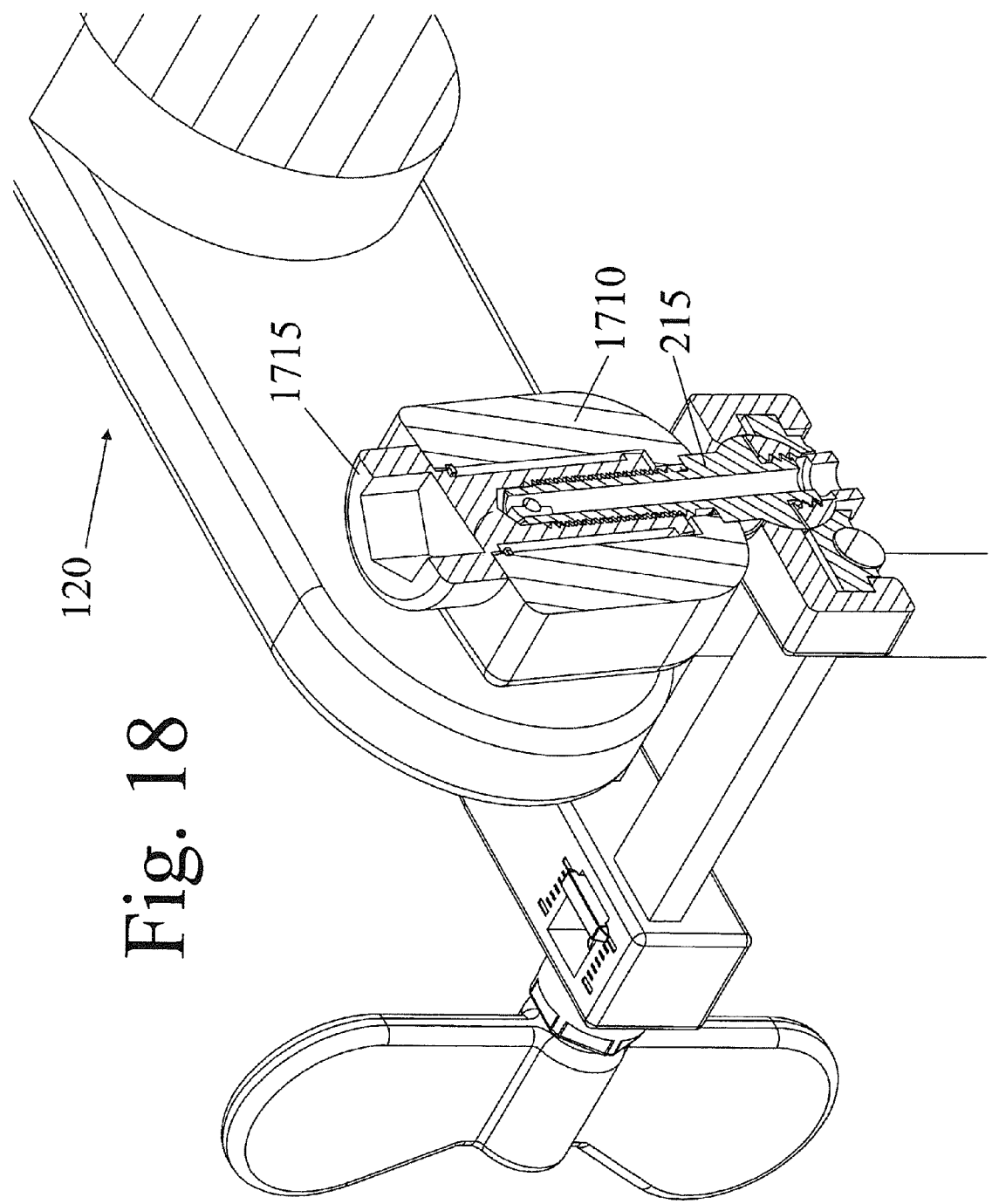
FIG. 18 shows a cross-sectional view of the attachment member attached to the attachment screw.

FIGS. 17A and 17B show enlarged views of the attachment member 1710 of the insertion device 120 being lowered onto the attachment screw 215 of the platform 115. FIG. 18 shows a cross-sectional view of the attachment member 1710 attached to the attachment screw 215. The attachment member 1710 includes an attachment screw 1715 that has a threaded bore that mates with a shank of the attachment screw 215. Once attached, the insertion device 120 can pivot about the axis B.

Figure 19:
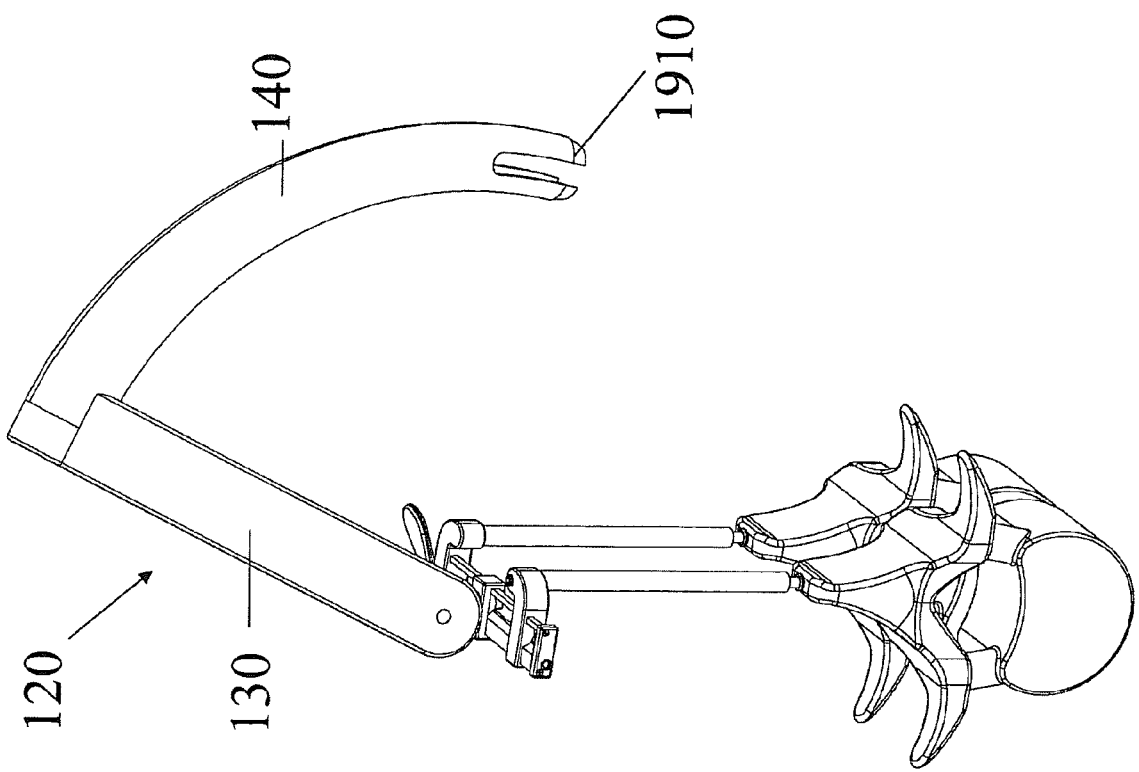
FIG. 19 shows the device including the pivotably mounted insertion device attached to a pair of vertebral bodies.

At this stage of the procedure, the device 110 including the pivotably mounted insertion device 120 is attached to the pair of vertebral bodies, as shown in FIG. 19. The insertion device 120 is positioned such that a distal tip 1910 of the curved portion 140 is positioned above the level of the patient's skin. For clarity of illustration, the skin is not illustrated in FIG. 19.

Figure 20:
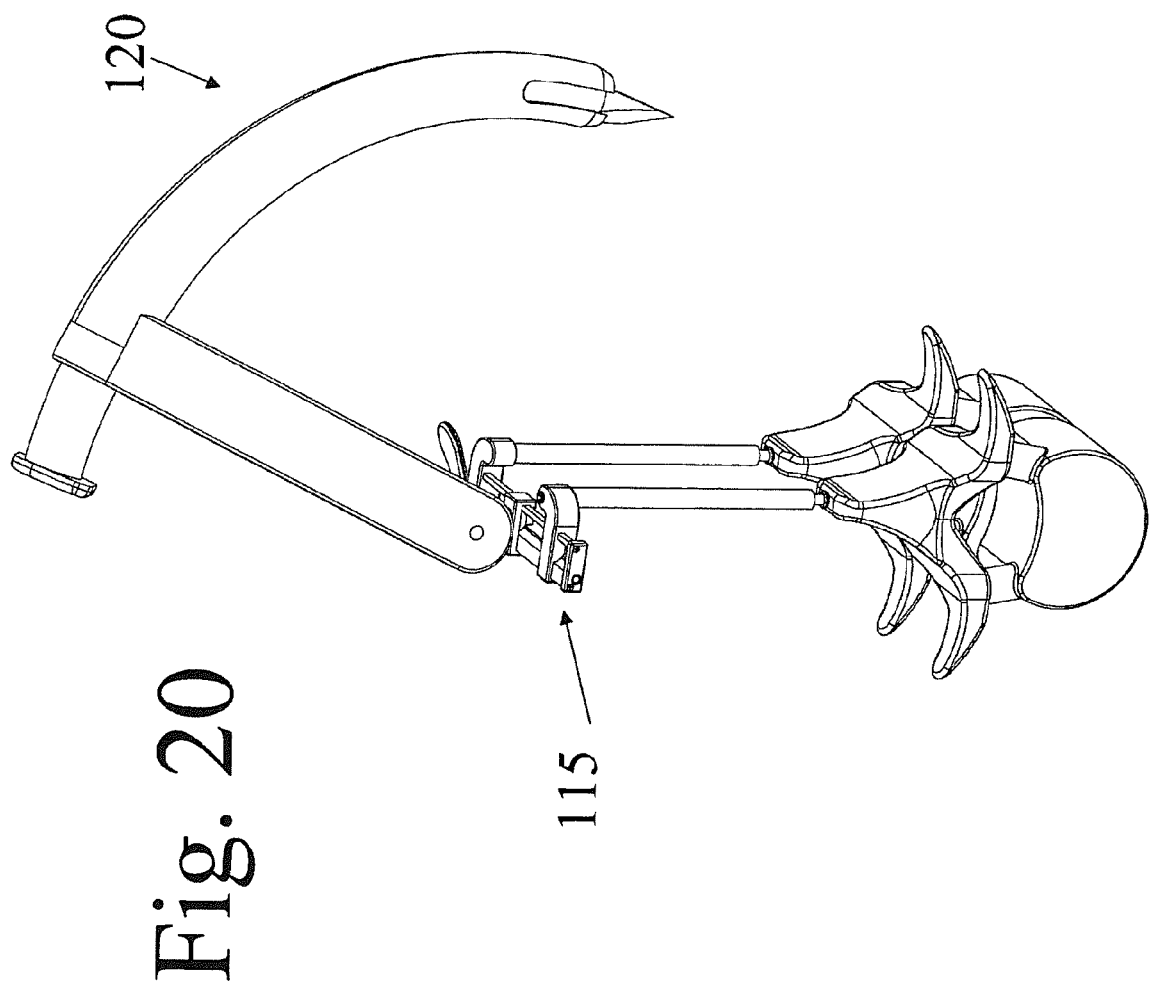
FIGS. 20-22 sequentially illustrate how the insertion device swings toward the target location where the implant is to be positioned.

FIG. 19 shows the insertion device 120 prior to insertion of the trocar 117 into the internal shaft of the curved portion 140. FIG. 20 shows the device 100 with the trocar 117 positioned within the curved portion 140 of the insertion device 120. The trocar has a handle on one end and a sharp, knife-like tip 2010 at an opposite end.

Figure 21:
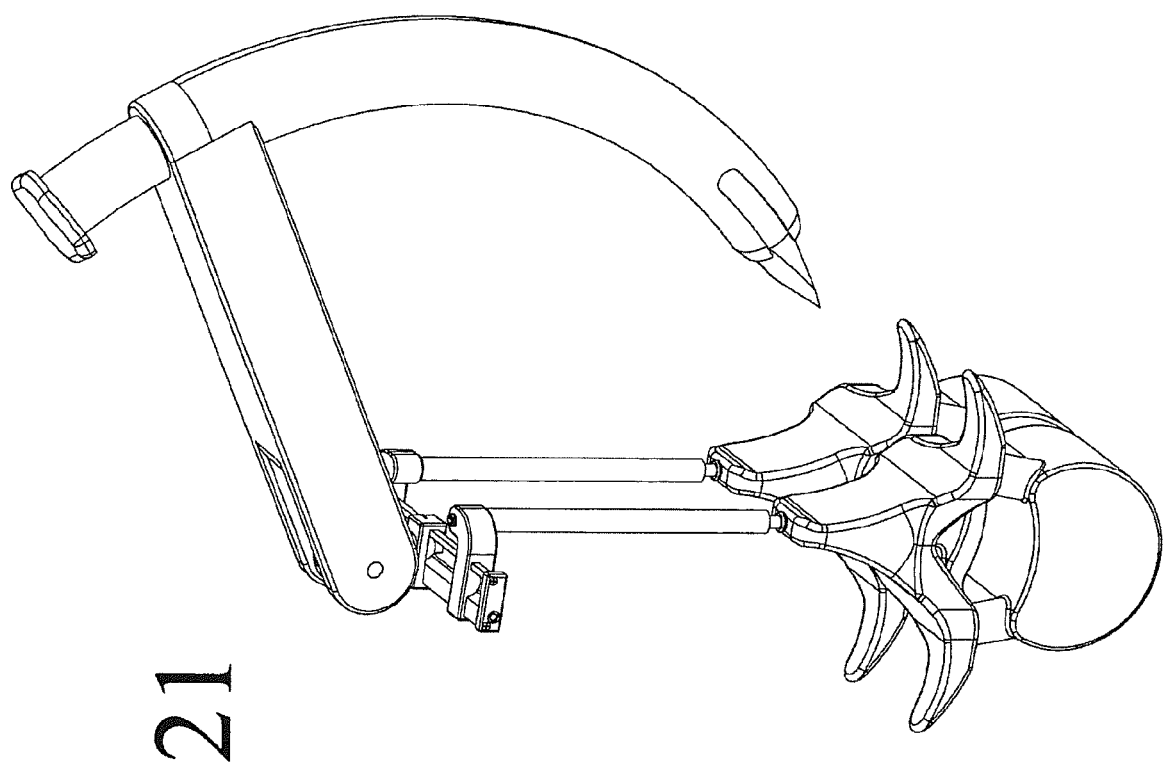
Figure 22:
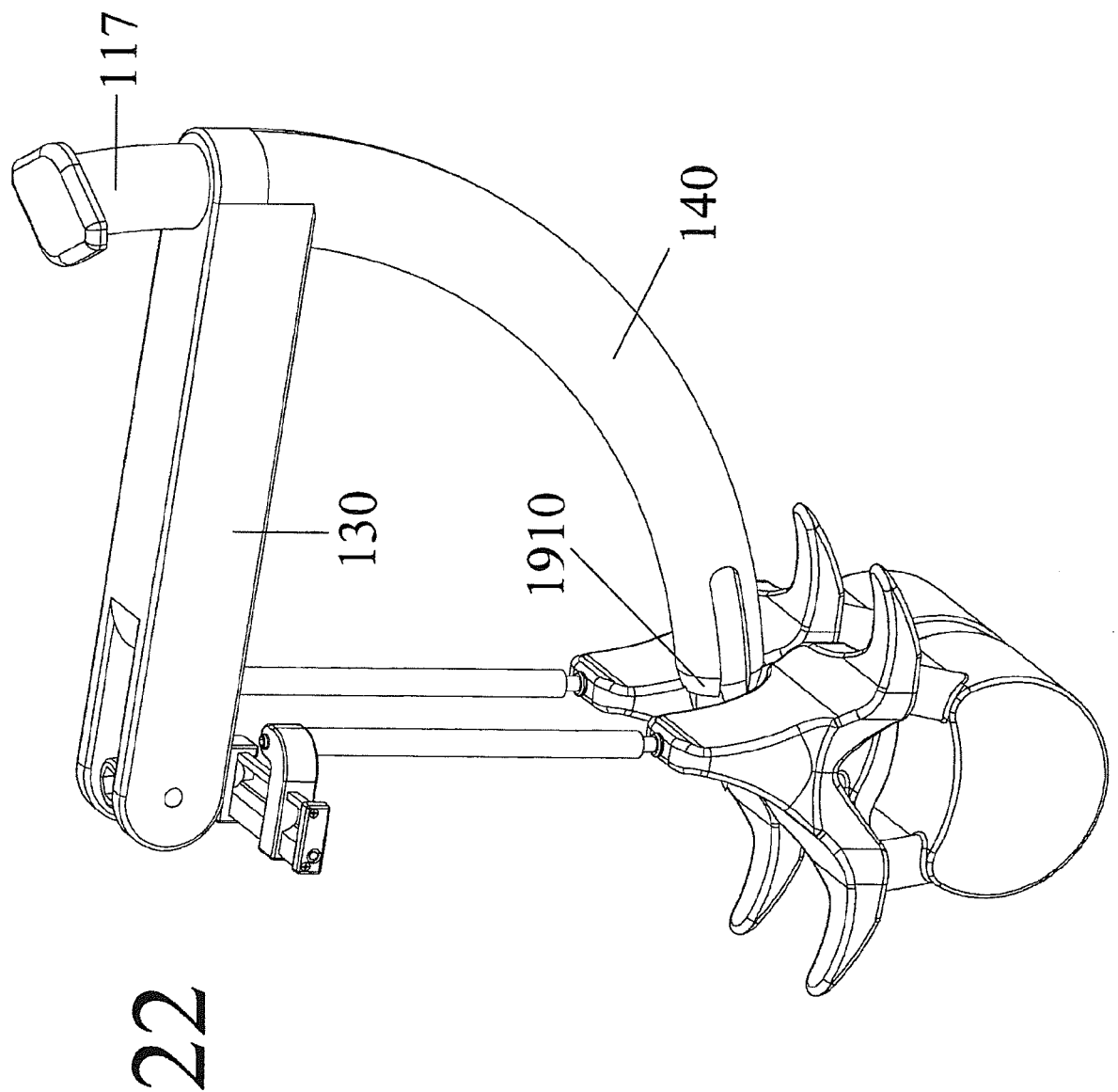
Figure 23:
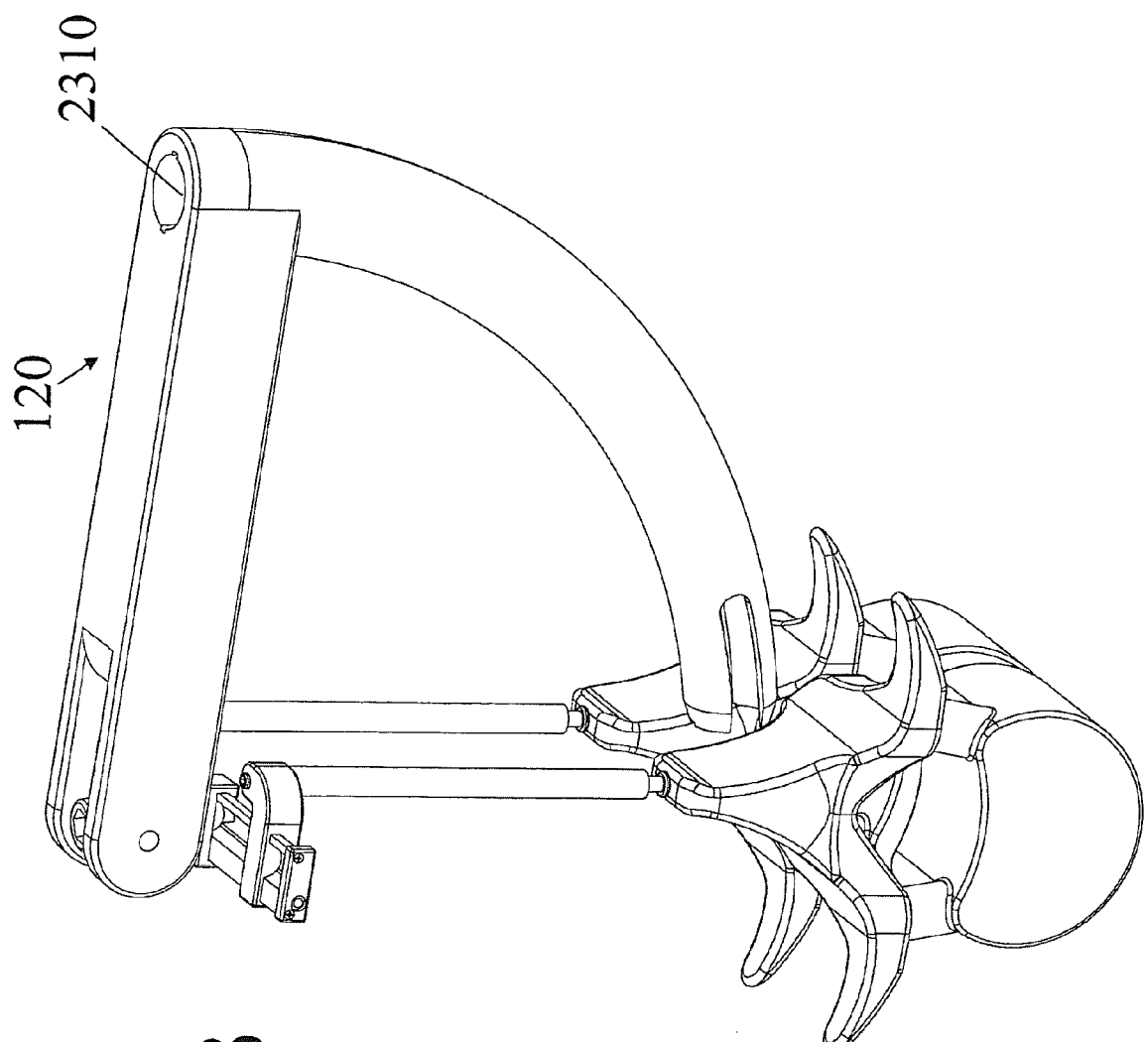
FIG. 23 shows the device with a trocar member removed.

FIGS. 20-22 sequentially illustrate how the insertion device 120 swings toward the target location where the implant is to be positioned. As mentioned, as the insertion device 120 pivots, the distal end 1910 of the curved portion 140 moves along a curvilinear pathway that intersects the target location. In FIG. 20, the tocar 117 is slid into the internal shaft of the curved portion 140. The handle of the trocar 117 is then pushed toward the skin so that the distal end 1910 swings toward the skin along a pathway D. The sharp, knife-like tip of the trocar 117 cuts through the skin and soft tissue as the insertion device 120 swings toward the skin. The trocar 117 and the curved portion 140 are then forced through the skin and soft tissue as illustrated in FIGS. 21 and 22 until the distal tip 1910 of the curved portion 140 abuts the side of the spinous processes of the vertebral bodies. Since the swinging insertion device 120 rotates about the locked platform 115 and arm 130 has a radius equivalent to the distance between the center of rotation and the needle tip, the curved portion 140 will necessarily travel along an arc that intersects the position of the needle tip. As shown in FIG. 23, the trocar 117 is then removed leaving the central shaft 2310 of the curved portion 140 of the insertion device free as a conduit for implant placement.

Figure 24:
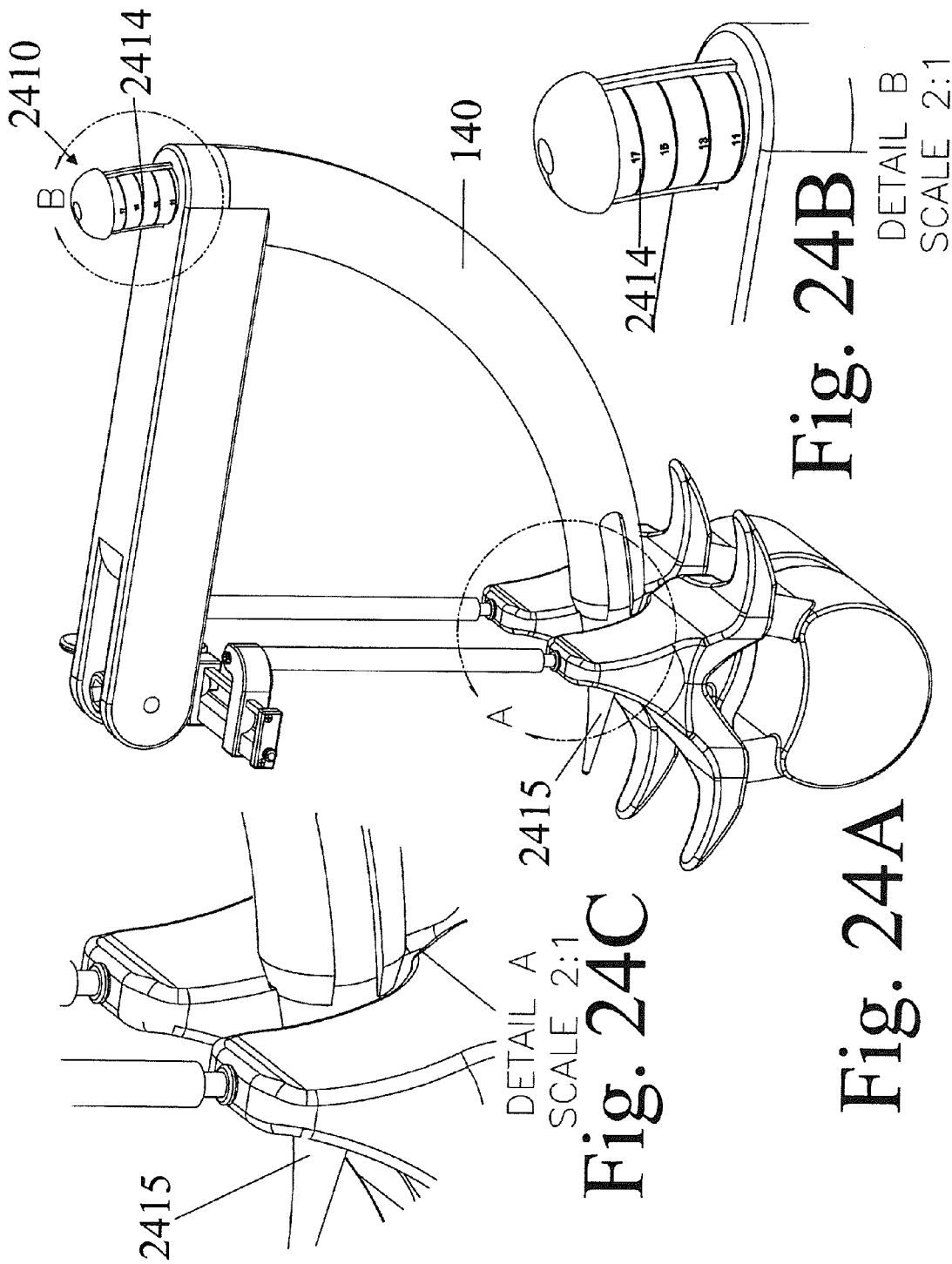
FIGS. 24A, 24B, and 24C show an exemplary sizing device for determining the appropriate size of an implant.

In the next step, the appropriate size of the implant is determined, wherein the appropriate size is based upon the size of the space between the two spinous processes. FIGS. 24A, 24B, and 24C show an exemplary sizing device 2410 for determining the appropriate size of an implant. The sizing device 2410 is an elongate rod that is sized to be positioned within the shaft 2310 of the curved portion 140. A proximal end of the sizing device 2410 has hatch marks 2414. A distal end 2415 of the sizing device has a gradually reducing diameter. As the sizing device 2410 is advanced further into the curved portion and into the space between the spinous processes, the distal end 2415 of the sizing device 2410 begins to distract the spinous processes and thereby unload the distractor.

Distraction of the spinous processes can be easily recognized by movement of pointer 925 (FIG. 12) relative to hatch marks 1120. That is, as the sizing device 2410 is advanced, the pointer 925 will indicate that less force is borne by the distraction screws 110. Once the sizing device 2410 is advanced sufficiently to unload the distraction screws, the implant size is noted on hatch markings 2414 on the sizing device 2410. For illustration, this size is shown as "11" in FIG. 24B. It should be appreciated that this number may provide an actual measure of the implant size in a recognized physical unit or simply give an arbitrary designation by which the implants are labeled. With the implant size determined, the sizing device 2410 is removed and the appropriate implant is selected.

Figure 25:
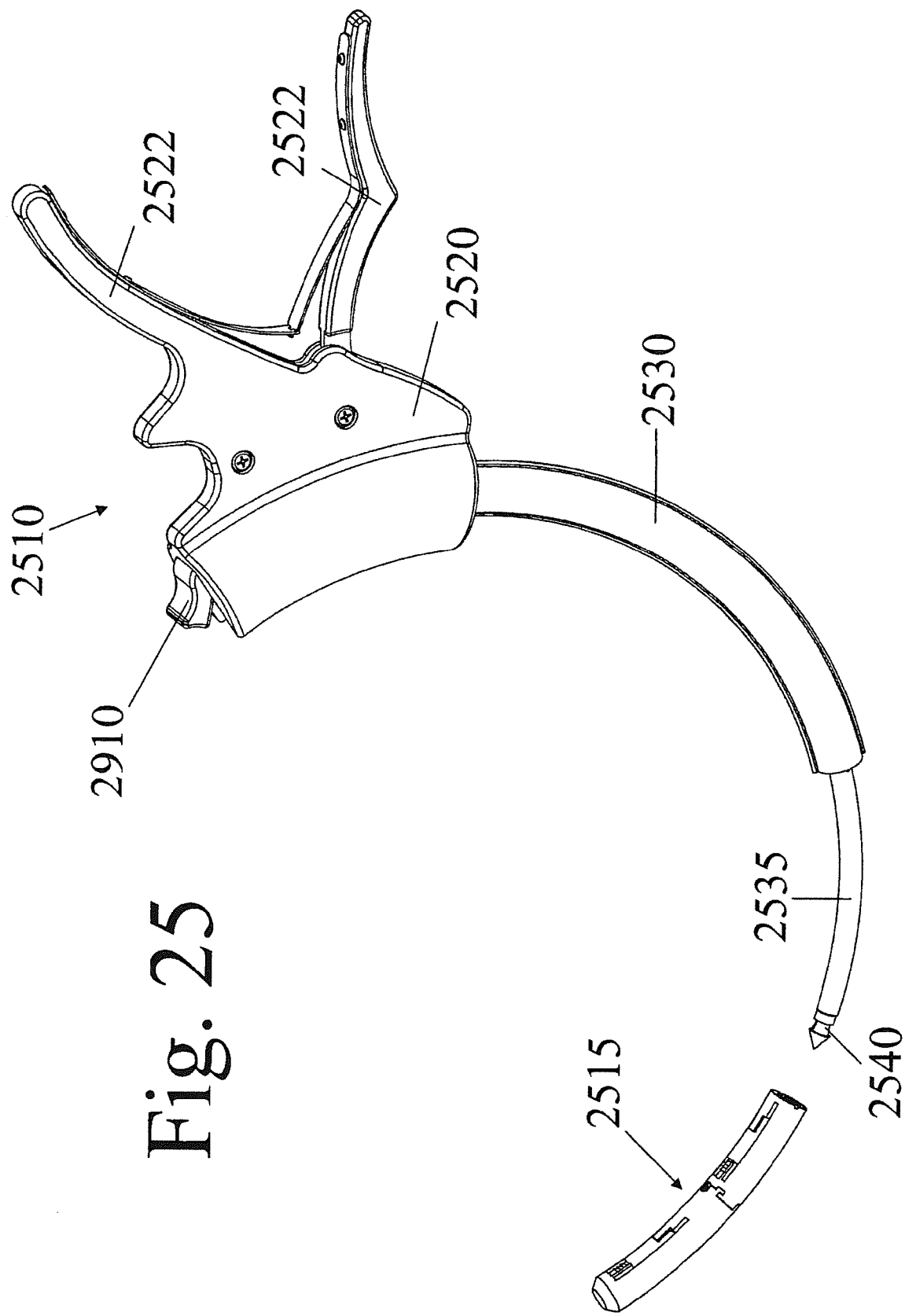
FIGS. 25 and 26 shows an implant holder device that can be used to hold an implant and install the implant via the internal shaft in the installer device.
Figure 26:
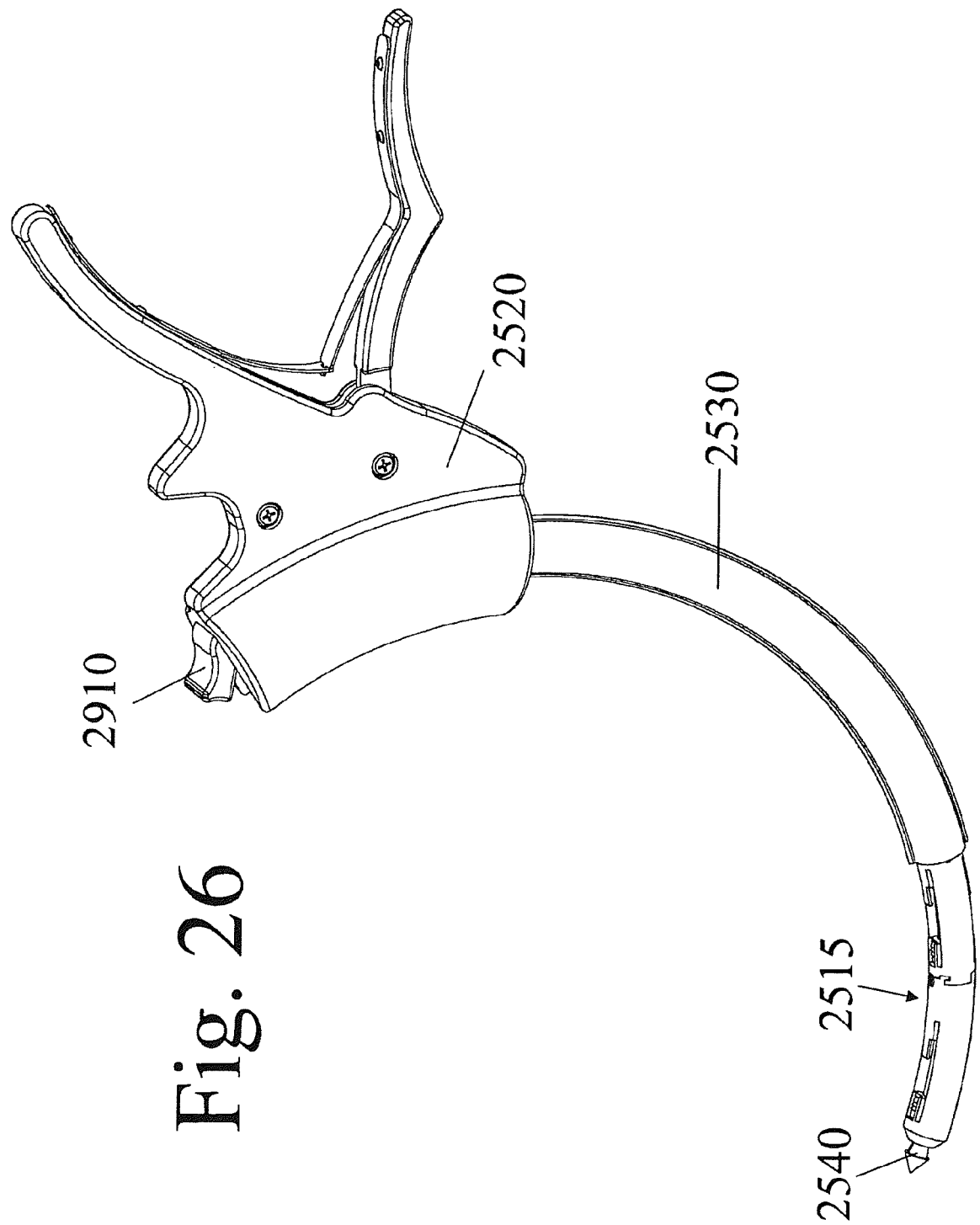

FIGS. 25 and 26 show an implant holder device 2510 that can be used to hold an implant 2515 and install the implant via the internal shaft in the curved portion 140 of the install device 120. The holder device 2510 includes a handle assembly 2520 having a pair of arms 2522 and 2524. A curved member 2530 extends outwardly from the handle assembly 2520. The curved member 2530 is coupled to a member 2535 and a member 2540, which are movable relative to one another in response to actuation of the handles 2522, 2524. The members 2530, 2535, and 2540 collectively form a holder element that holds and secures the implant 2515. The implant 2515 has a curvilinear shape and mounts onto the members 2535 and 2540, as shown in FIG. 26 and described below.

FIGS. 27A and 27B show the implant 2515 with extendable wings 2710 in an undeployed (FIG. 27A) and a deployed state (FIG. 27B). The implant 2515 has an internal bore 2715. The wings 2710 are formed of foldable arms 2720. The implant 2515 also includes ratchets 2730 that are engageable by protrusions 2735. An indentation 2732 is located along a proximal edge of the implant 2515. When the implant 2515 is positioned within the space between the spinous processes, the implant 2515 is collapsed along its length, which causes the arms 2720 to fold outward and form the wings 2710. The protrusions 2735 engage the ratchets 2730 to lock the implant in the deployed state.

The implant 2515 mounts onto the holder 2510 by sliding the members 2535, 2540 through the bore 2715 in the implant 2515 such that the implant 2515 is positioned over the members 2535, 254, as shown in FIG. 26. When the implant 2515 is mounted as such, a protrusion 2810 on the distal edge of the member 2530 engages the indentation 2732 on the proximal edge of the implant 2515, as shown in FIG. 28. The engagement prevents the implant 2515 from rotating when mounted on the members 2530, 2540.

Figure 30:
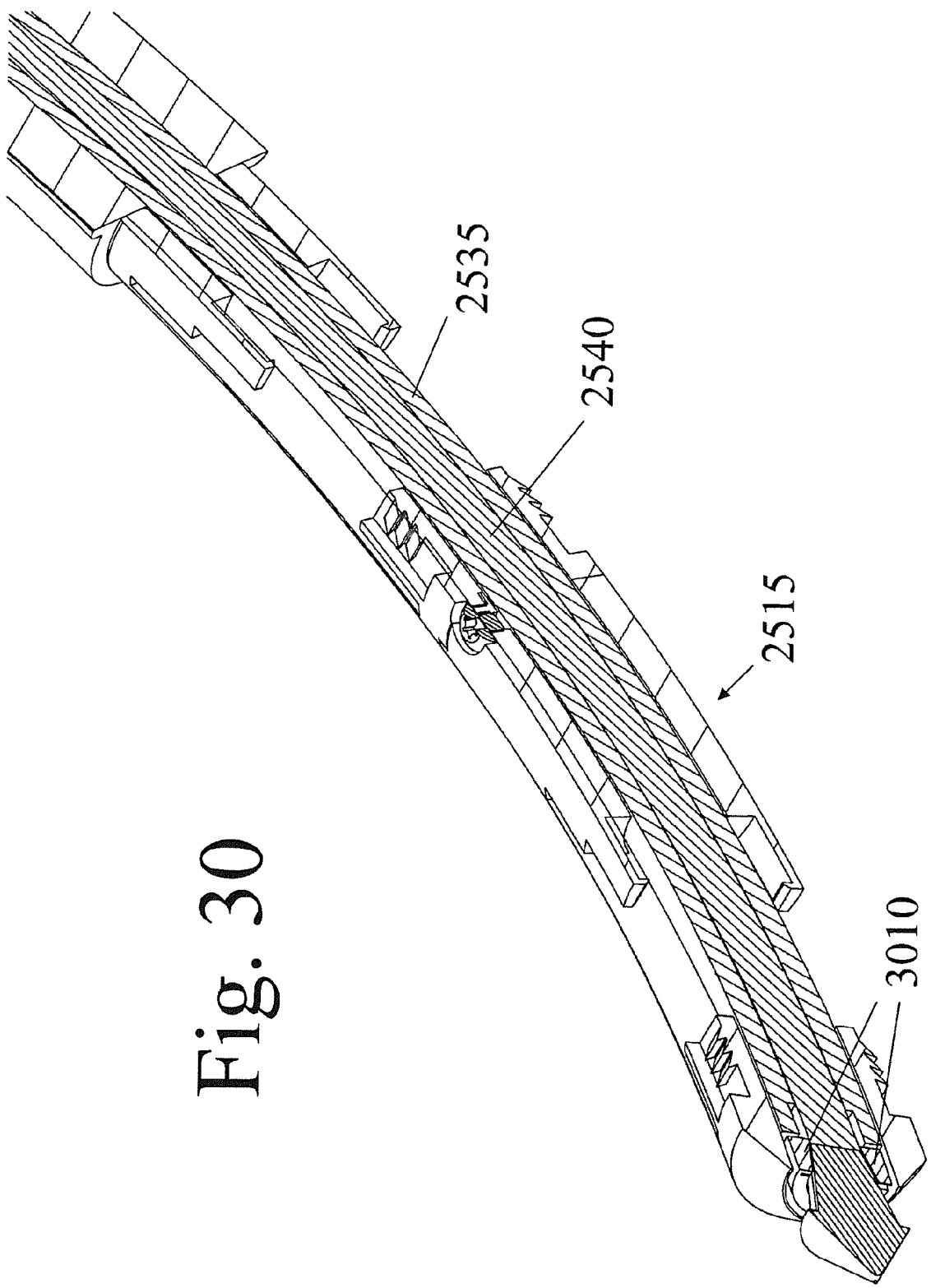
FIG. 30 shows a close-up view of the implant attached to the holder.

FIG. 29 shows a cross-sectional view of the implant attached to the holder. FIG. 30 shows a close-up view of the implant attached to the holder. The members 2535 and 2540 of the holder 2510 are both positioned within the central bore 2715 and engage the head of the implant. A handle 2910 on the assembly 2520 is actuated to cause the member 2540 to move back relative to the member 2535 and expand a split ring 3010. As the split ring 3010 expands, the ring 3010 wedges against the internal wall of the bore 2715 and thereby lock the implant 2515 onto the implant holder 2510. The locking mechanism at the head of the implant and the prevention of rotation (by engagement of protrusion 2810 and indentation 2732 as shown in FIG. 28) effectively immobilize the implant 2515 relative to the holder 2510.

Figure 31:
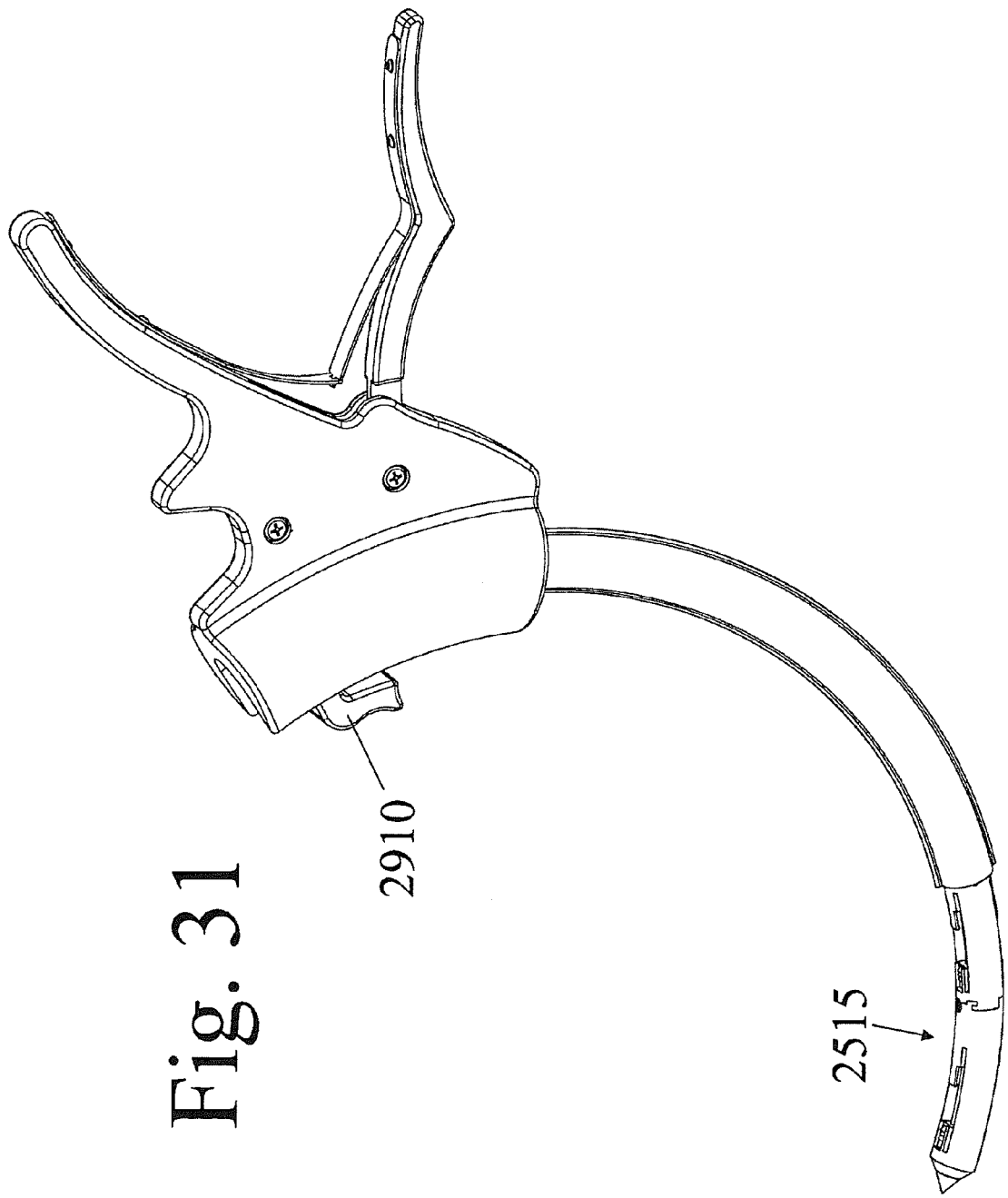
FIG. 31 shows the implant locked onto the holder with a handle in a locked position.
Figure 32:
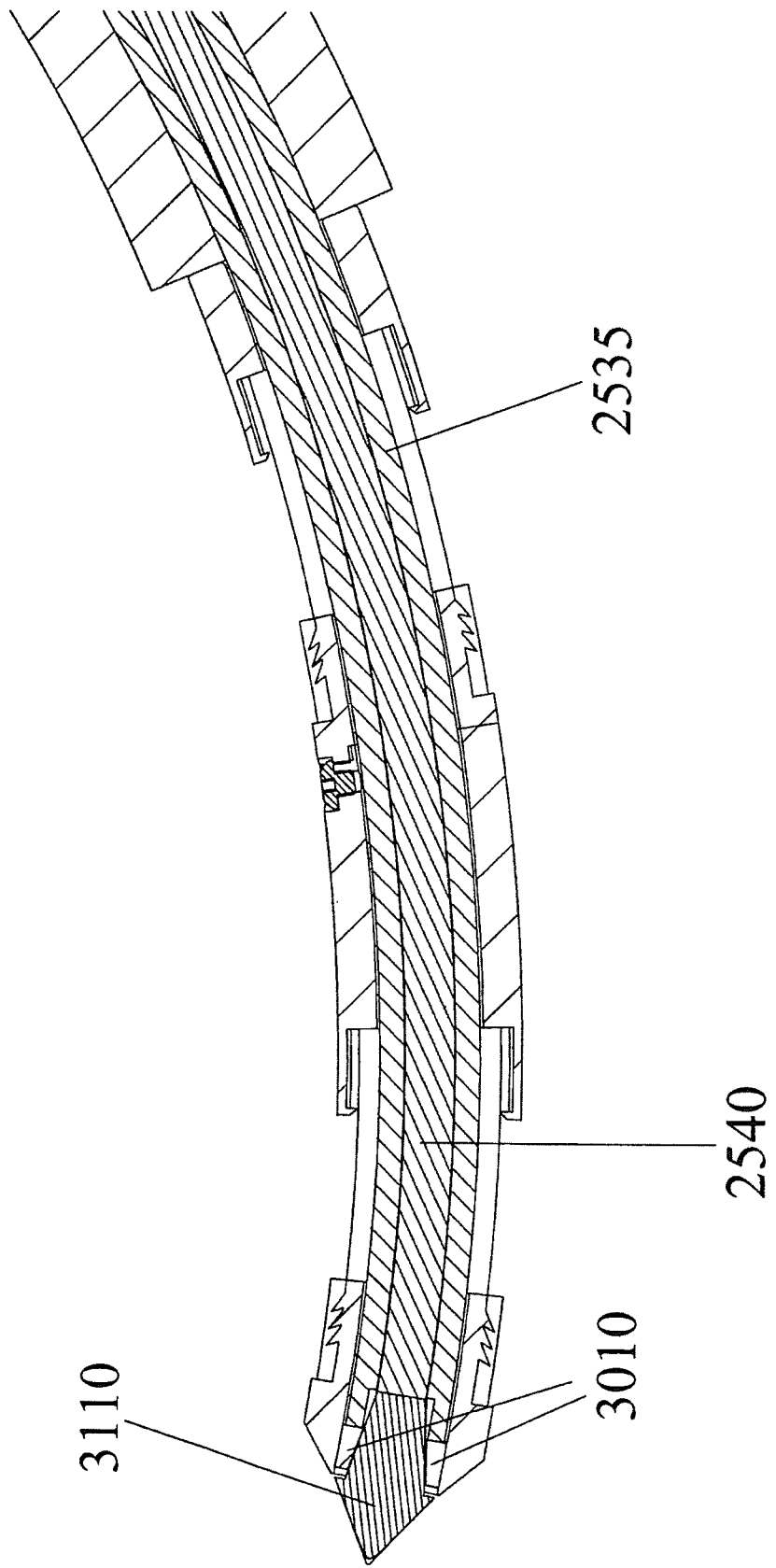
FIG. 32 shows a close-up, cross-sectional view of the implant end of the holder.

FIG. 31 shows the implant 2515 locked onto the holder 2510 with the handle 2910 in a locked position. FIG. 32 shows a close-up, cross-sectional view of the implant end of the holder 2510. Note that the split ring 310 now abuts the inside of the bore 2715 and a conical head 3110 of the member 2540 is situated at the distal tip of the implant 2515.

Figure 33:
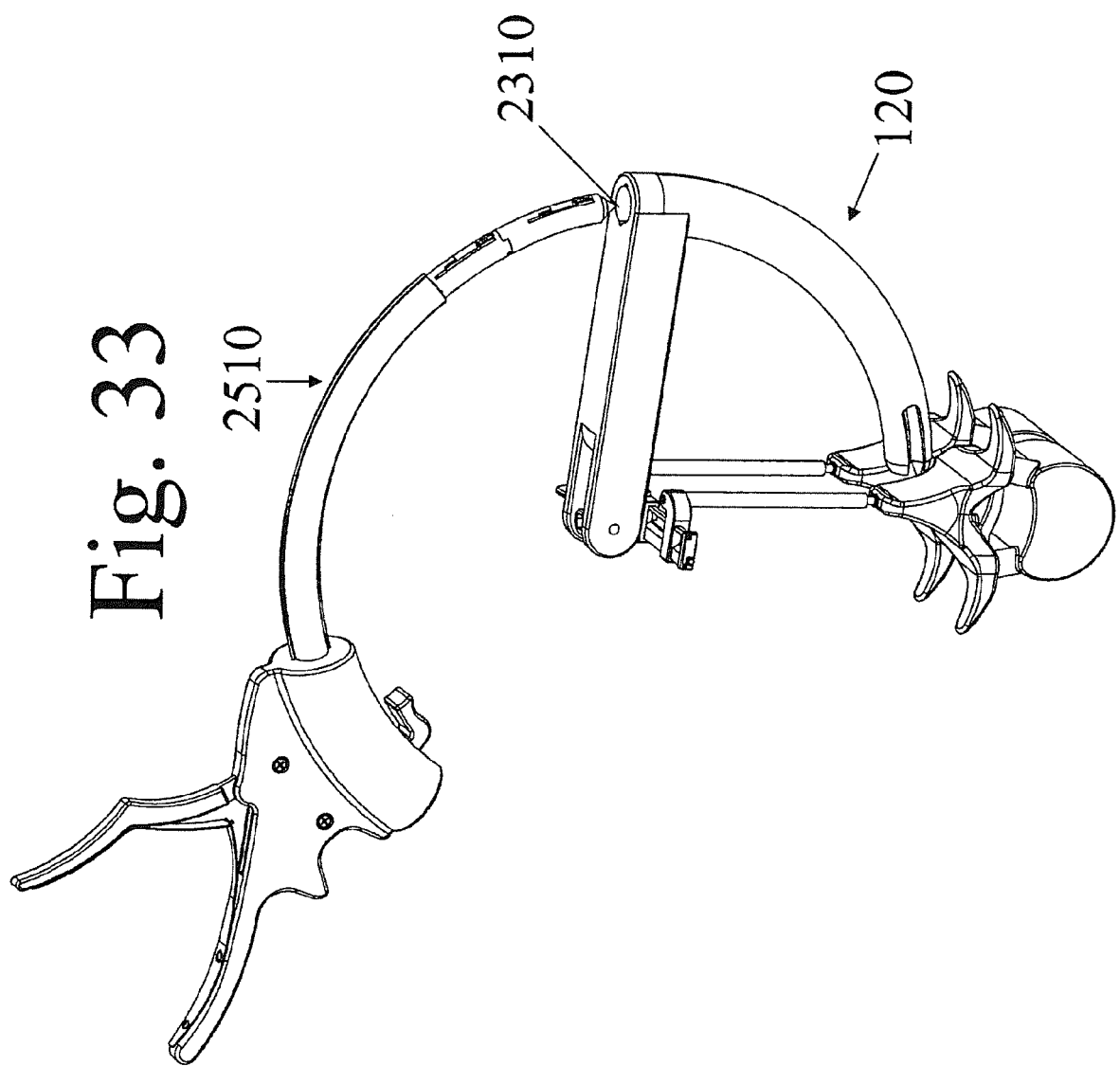
FIG. 33 shows the holder and attached implant just prior to insertion into the internal shaft of the curved portion.
Figure 34:
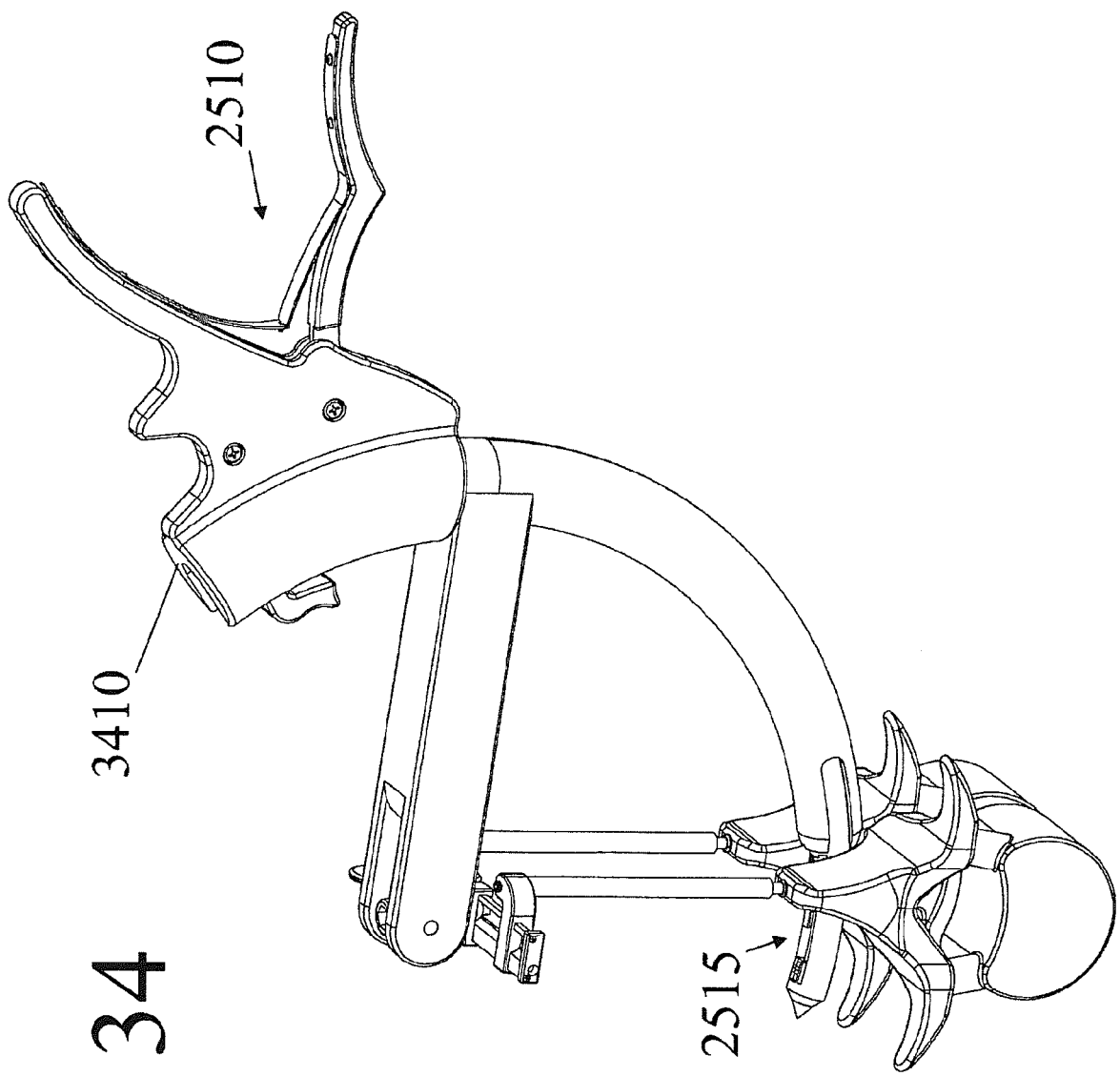
FIG. 34 shows the device with the holder and implant in a ready-to-deploy state.

At this stage of the procedure, the implant 2515 is locked onto the holder 2510 pursuant to the above-described process. The holder 2510 and the attached implant 2515 can now be inserted into the internal shaft of the curved member 140 of the insertion device 120. FIG. 33 shows the holder 2510 and attached implant 2515 just prior to insertion into the internal shaft 2310 of the curved portion 140. The holder 2510 and attached implant 2515 are slid through the internal shaft 2310 until the implant protrudes out of the curved portion and is positioned between the spinous processes, as shown in FIG. 34. If needed, a mallet may be used to apply force to surface 3410 of the implant holder 2510 in order to position the implant between the spinous processes.

Figure 35:
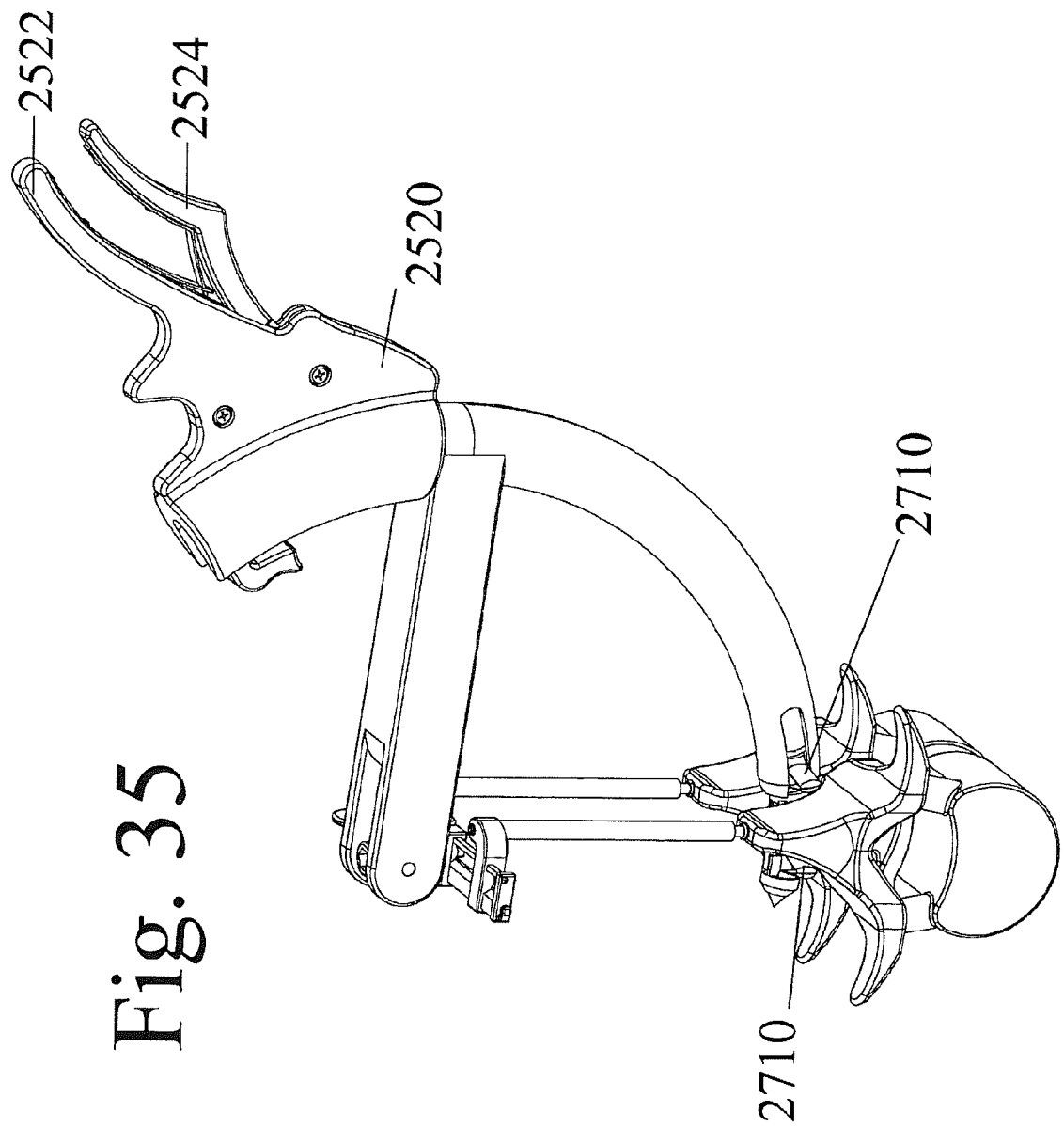
FIG. 35 shows the device with the holder and implant in a deployed state.

The handles 2522 and 2524 of the implant holder 2510 are then actuated, which causes the ends of members 2530 and 2535 to move towards one another. The actuation of the handles 2522 and 2524 causes the implant to deform such that the wings 2710 are deployed, as shown in FIG. 35.

Figure 36:
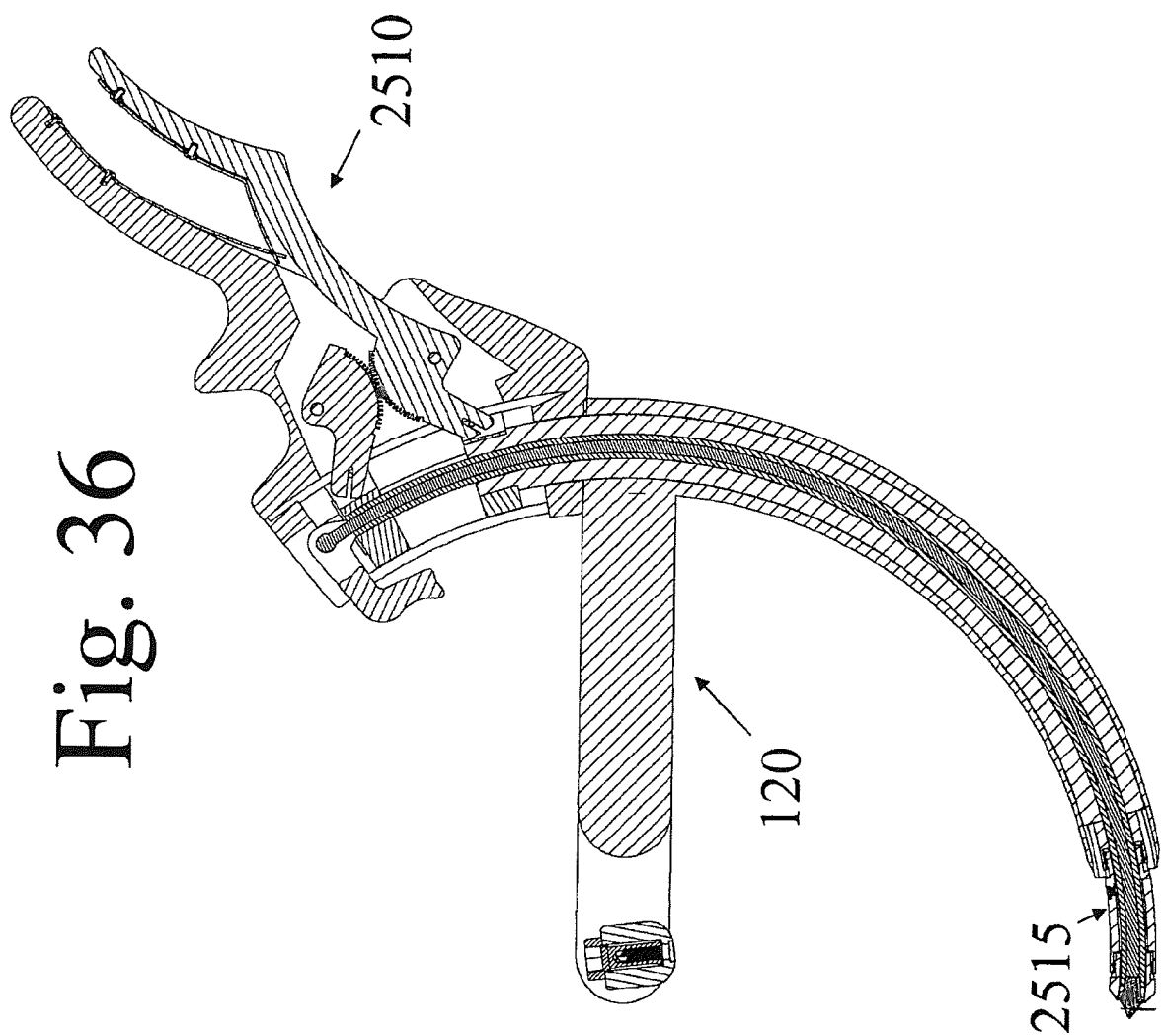
FIG. 36 shows a cross-sectional view of the deployed holder and implant.
Figure 37:
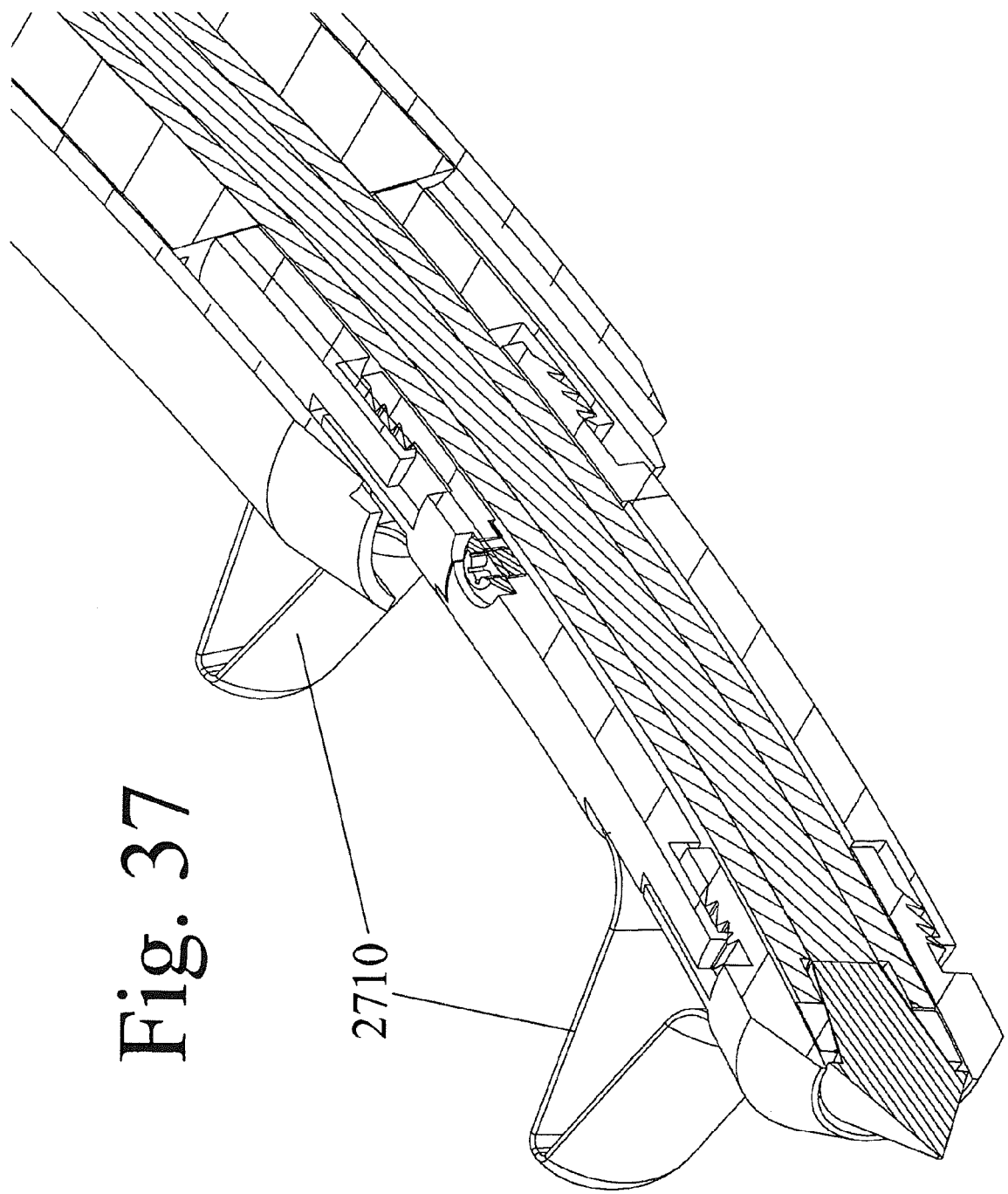
FIG. 37 shows a close-up view of the implant coupled to the holder.
Figure 38:
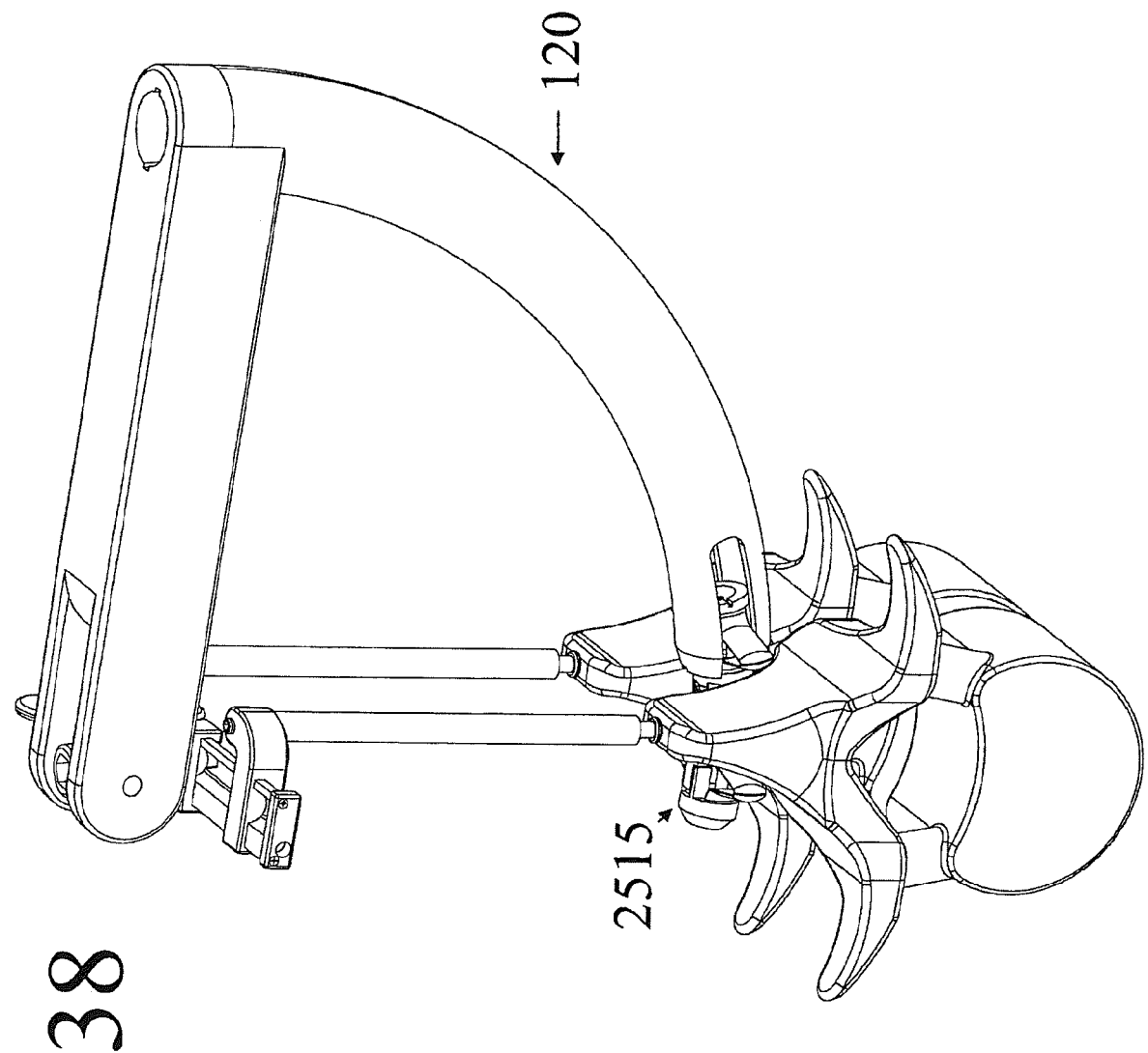
FIG. 38 shows the implant deployed between the vertebral bodies and the holder removed from the device.
Figure 39:
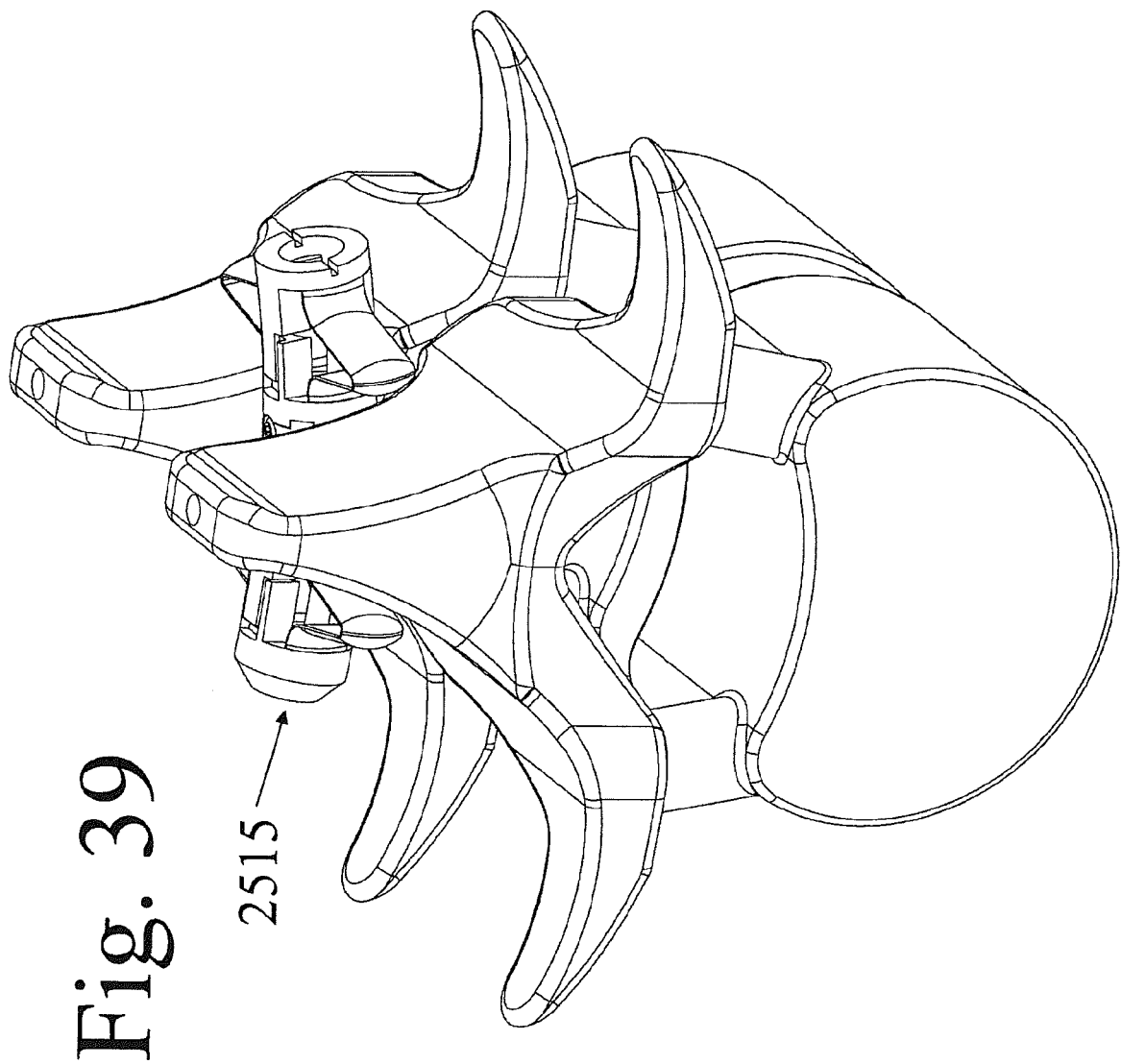
FIG. 39 shows the implant deployed between the vertebral bodies after the inserter device has been rotated out of the soft tissue and the device and distraction screws have been removed.

FIG. 36 shows a cross-sectional view of the deployed holder and implant. FIG. 37 shows a close-up view of the implant coupled to the holder 2510. The handle 2524 and 2522 are connected to a mechanism that causes the members 2530 and 2535 to move when the handles are actuated. The movement causes the implant wings to deploy. Note that the implant's ratchet locking mechanism (the ratchets 2730 and protrusions 2735) is now locked and keeps the implant in the deployed position. At this stage, the handle 2910 can be unlocked and the implant holder 2510 removed form the central channel of the curved portion 140 of the installer device 120. FIG. 38 shows the implant 2515 deployed between the vertebral bodies and the holder removed from the device 100. FIG. 39 shows the implant 2515 deployed between the vertebral bodies after the inserter device 120 has been rotated out of the soft tissue and the device 100 and distraction screws have been removed.

Figure 40:
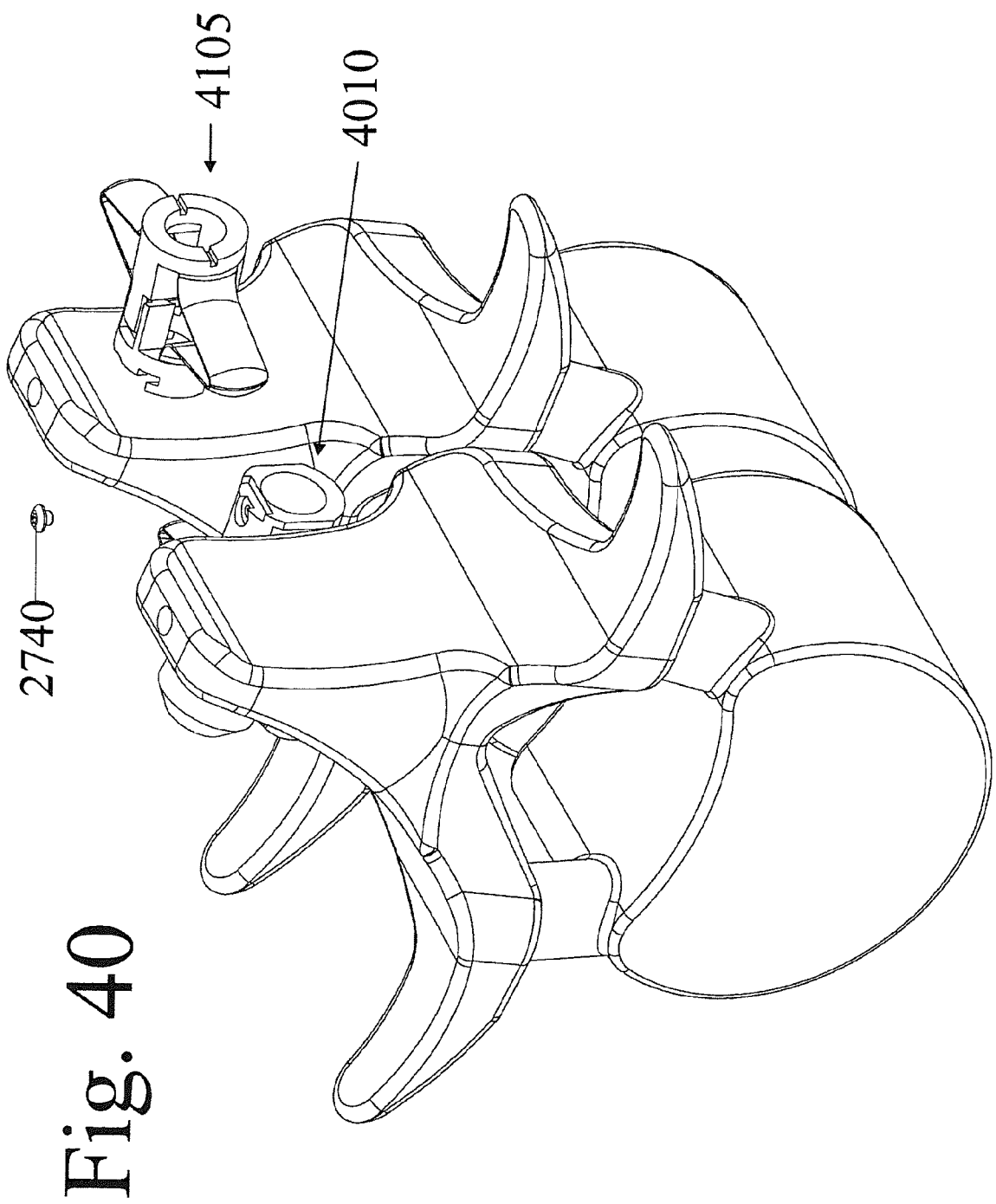
FIG. 40 shows how a screw may be removed and the implant disassembled.

With reference again to FIG. 27, the implant 2515 includes a screw 2740 that secures a first portion of the implant to a second portion of the implant. When the screw 2740 is in place, the first portion and second portion are secured to one another. When the screw 2740 is removed, the first portion and second portion detach from one another. The implant 2515 can advantageously be disassembled by removing the screw 2740. If open surgery is required at a future date, the implant 2515 can be disassembled and completely removed—making the implantation procedure completely reversible. FIG. 40 shows how the screw 2740 may be removed and the implant divided into subunits comprised of a first portion 4010 and a second portion 4015. This permits the removal of each subunit without removal of the interspinous ligament.

Figure 41:
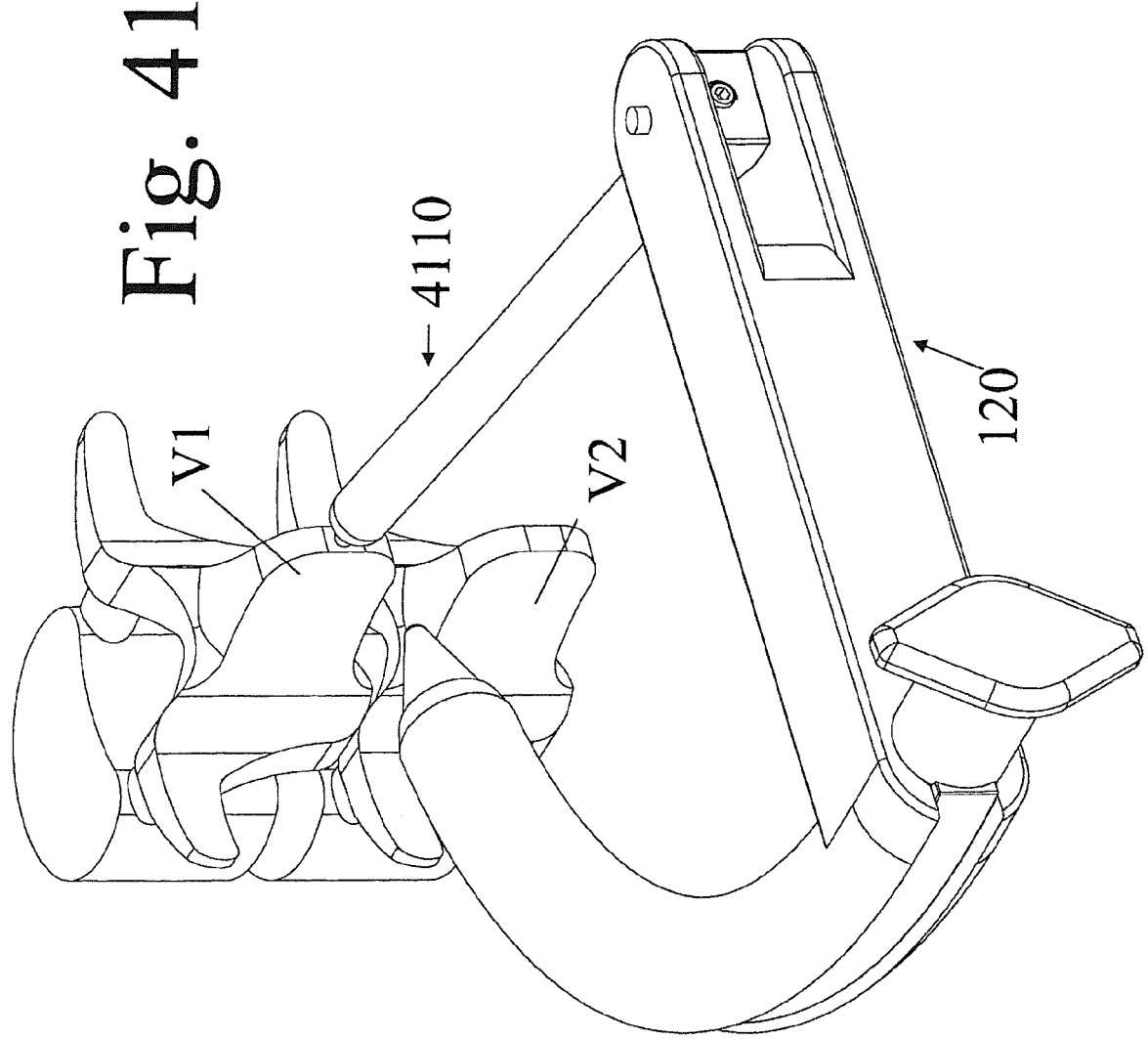
FIG. 41 shows another embodiment of a device with a swinging or pivoting installer device.

FIG. 41 shows another embodiment of a device with a swinging or pivoting installer device 120 having a structure similar to the installer device 120 described above. Thus, like reference numerals refer to like structures. In this embodiment, the installer device 120 mounts at the proximal end of a single mounting post 4110 that attaches at a distal end to the spinous process of a vertebral body V1 or V2.

Figure 42:
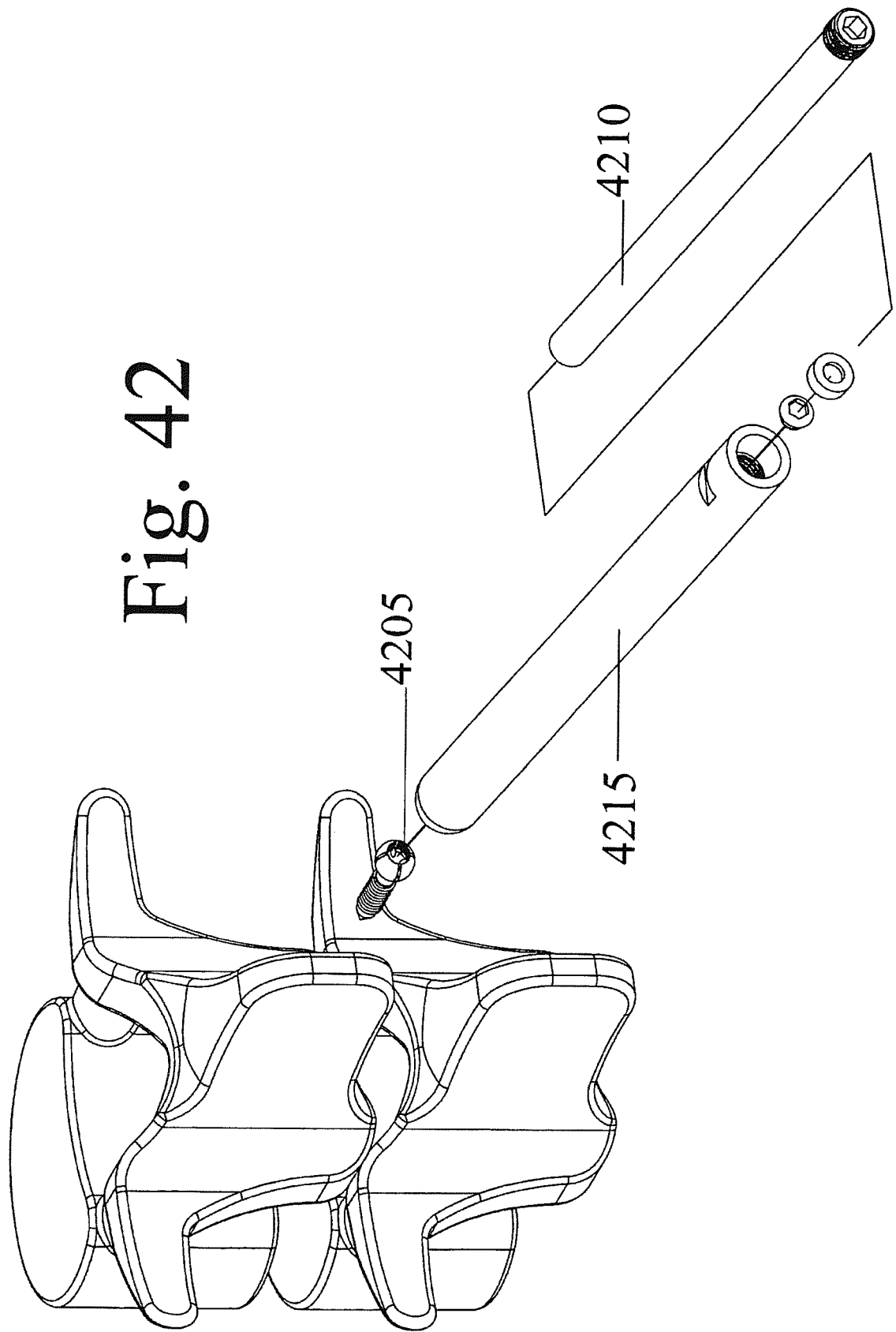
FIG. 42 shows a mounting post in an exploded state.
Figure 43:
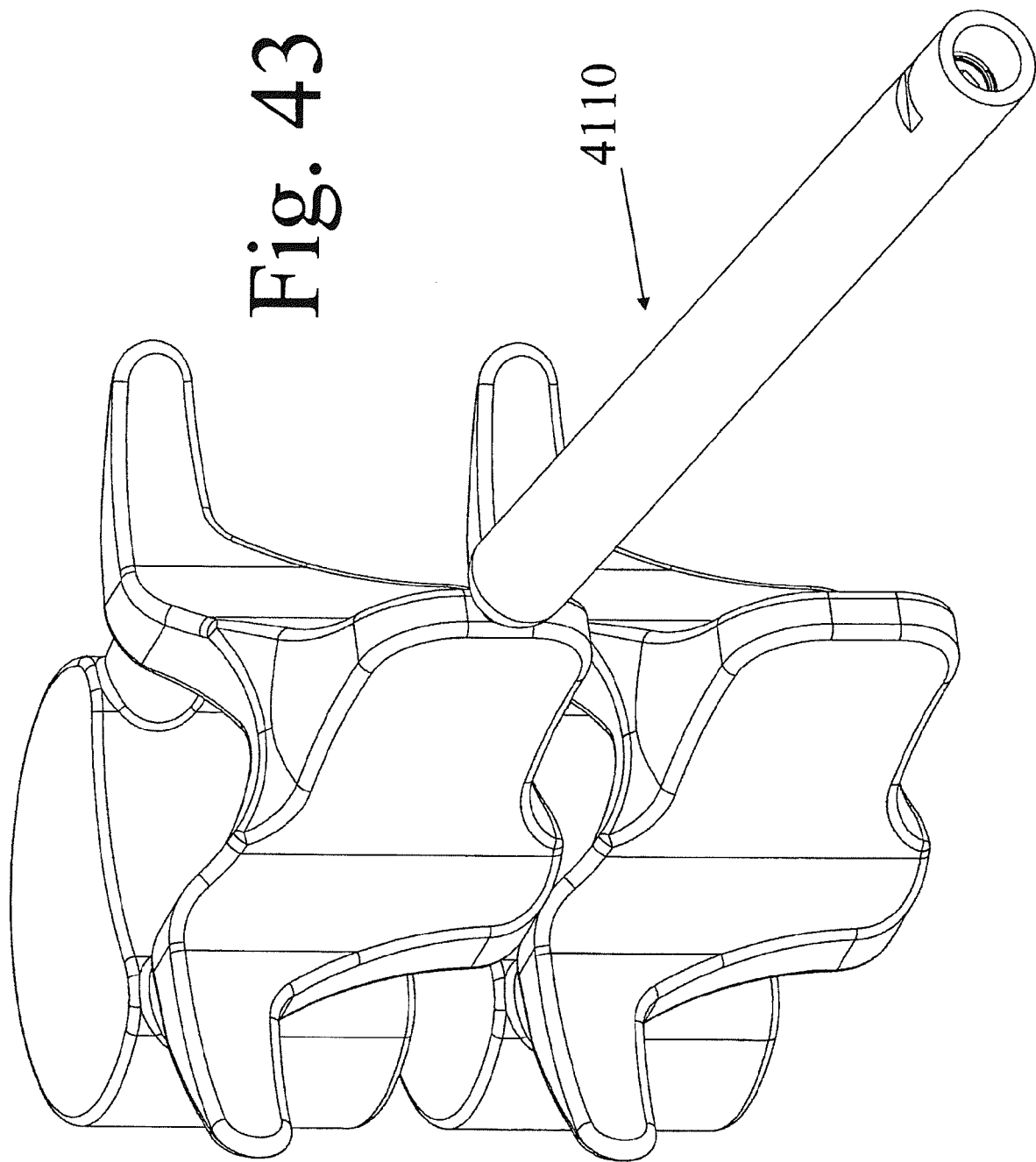
FIG. 43 shows the mounting post attached to a vertebral body.

FIG. 42 shows the mounting post 4110 in an exploded state. The mounting post 4110 includes a screw 4205 with a shank that screws into the spinal process. A two-piece post portion couples to the screw 4205. The post portion has an internal member 4210 positionable inside an external member 4215. The internal member 4210 and the external member 4215 are coupled to one another to form the elongate mounting post 4110, as shown in FIG. 43.

Figure 44:
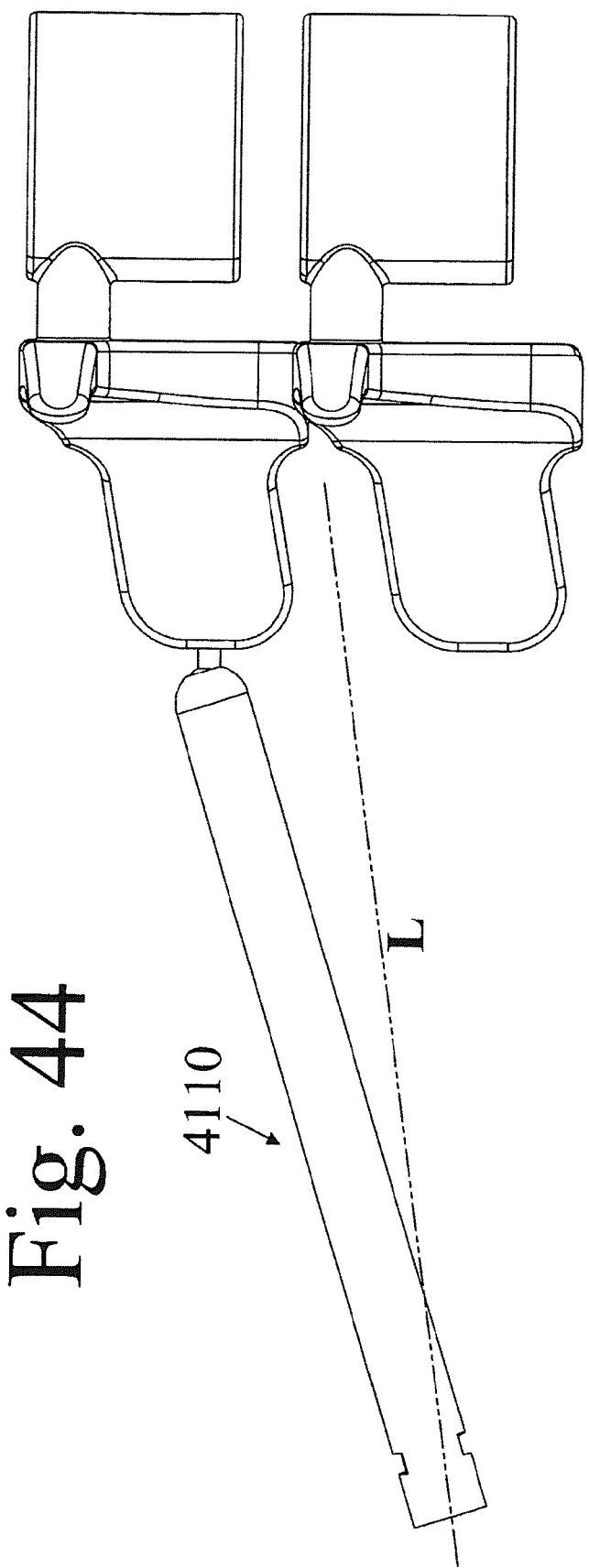
FIG. 44 shows a free end of the post a positioned along a line L parallel to the inter-spinous space.

Under X-ray guidance, the screw 4205 of the post 4110 is percutaneously attached onto the spinous process through a small skin incision. The internal member 4210 of the post 4110 is configured to lock to the screw 4205 while the screw 4205 is being driven into bone. In this way, rotation of the outer member 4215 causes advancement of the screw into the spinous process. The internal member 4210 is then unlocked and the external member 4215 is moved in the long axis of the spine until the free end of the post 4110 rests along a line L parallel to the inter-spinous space, as shown in FIG. 44. The inter-spinous space is easily identified on X-rays. After this is performed, the internal member 4215 is locked, which immobilizes the post 4110 relative to the screw 4205.

Figure 45:
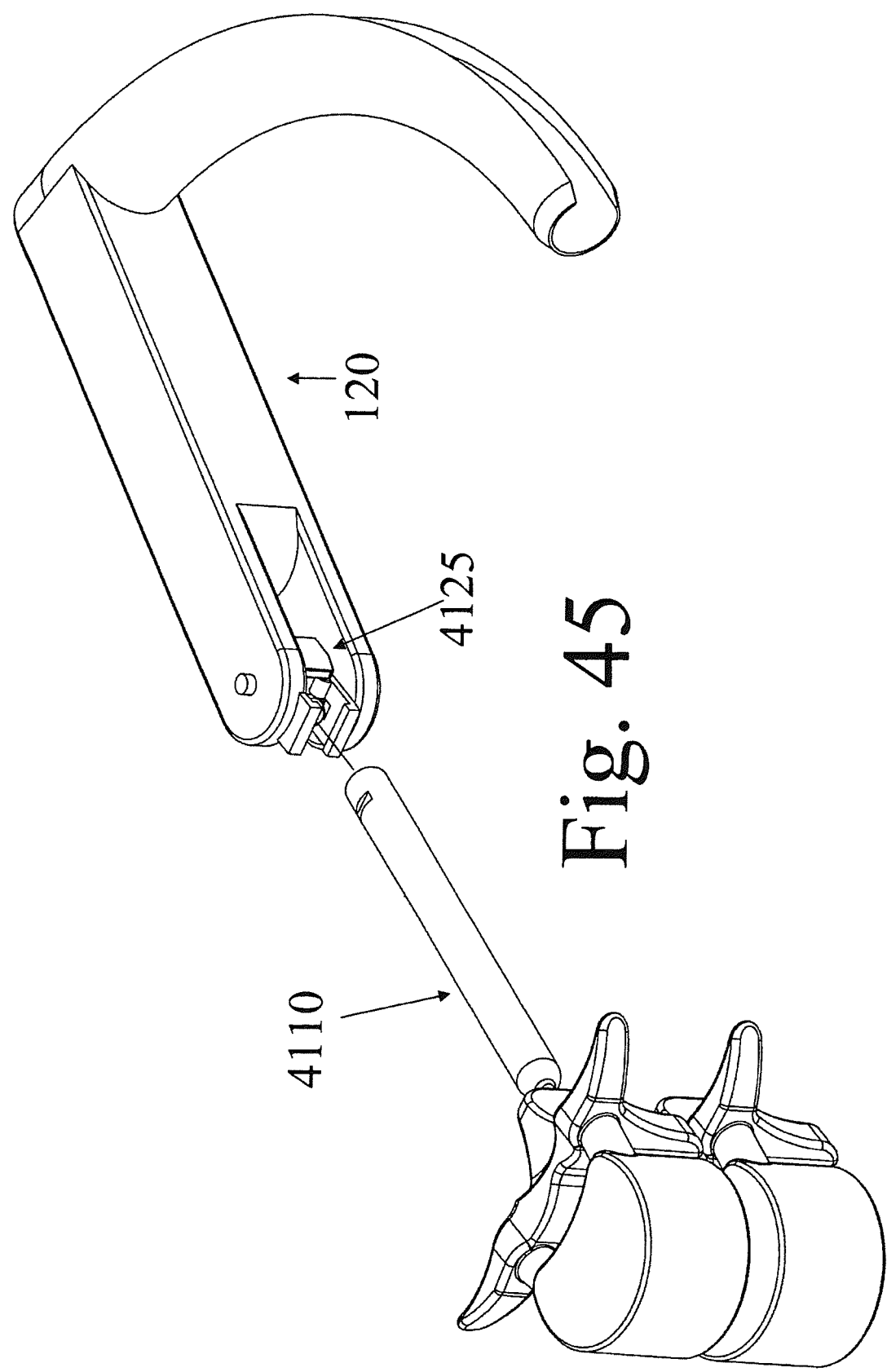
FIG. 45 shows the insertion device prior to attachment to the post.
Figure 46:
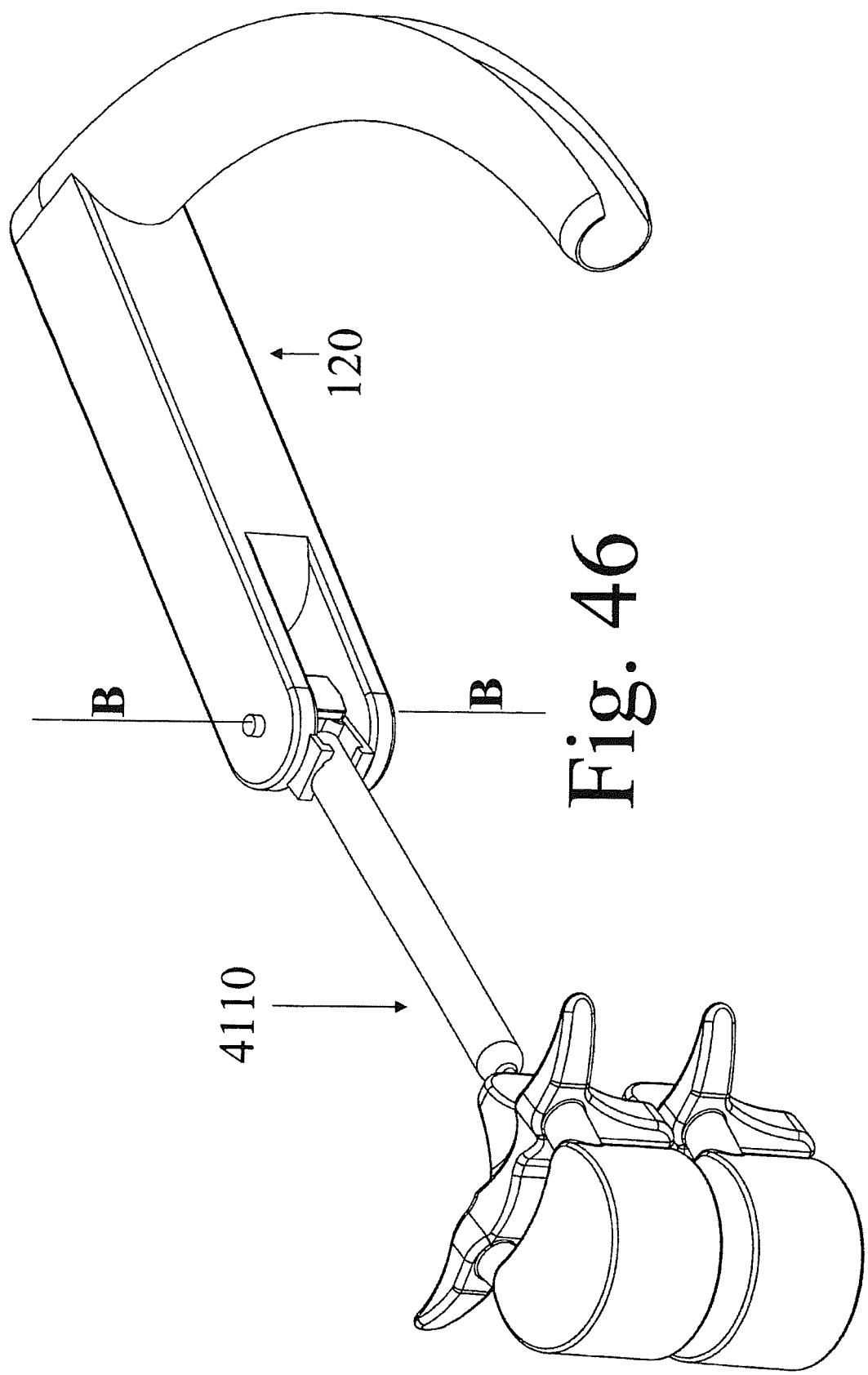
FIG. 46 shows the insertion device attached to the post.

After the post-screw is appropriately positioned, the installer device 120 is attached onto the proximal end of the post 4110 as shown in FIGS. 45 and 46. An attachment member 4125 pivotably attaches the insertion member 120 to the proximal end of the post 4110. The attachment member 4125 is configured to permit the insertion member 120 to pivot about a pivot axis B (shown in FIG. 46).

Figure 47:
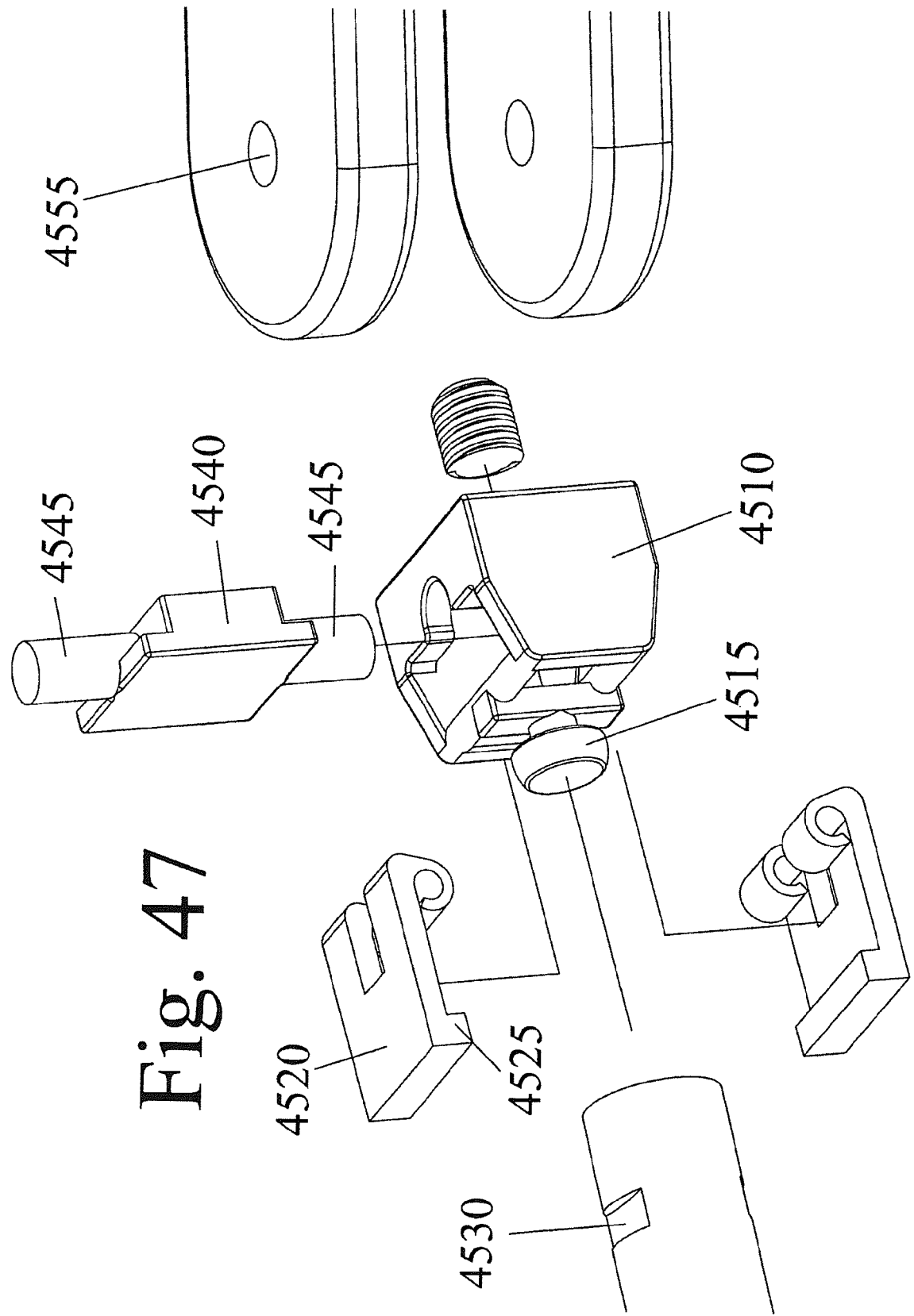
FIG. 47 shows an exploded view of an attachment device for attaching the insertion device to the post.
Figure 48:
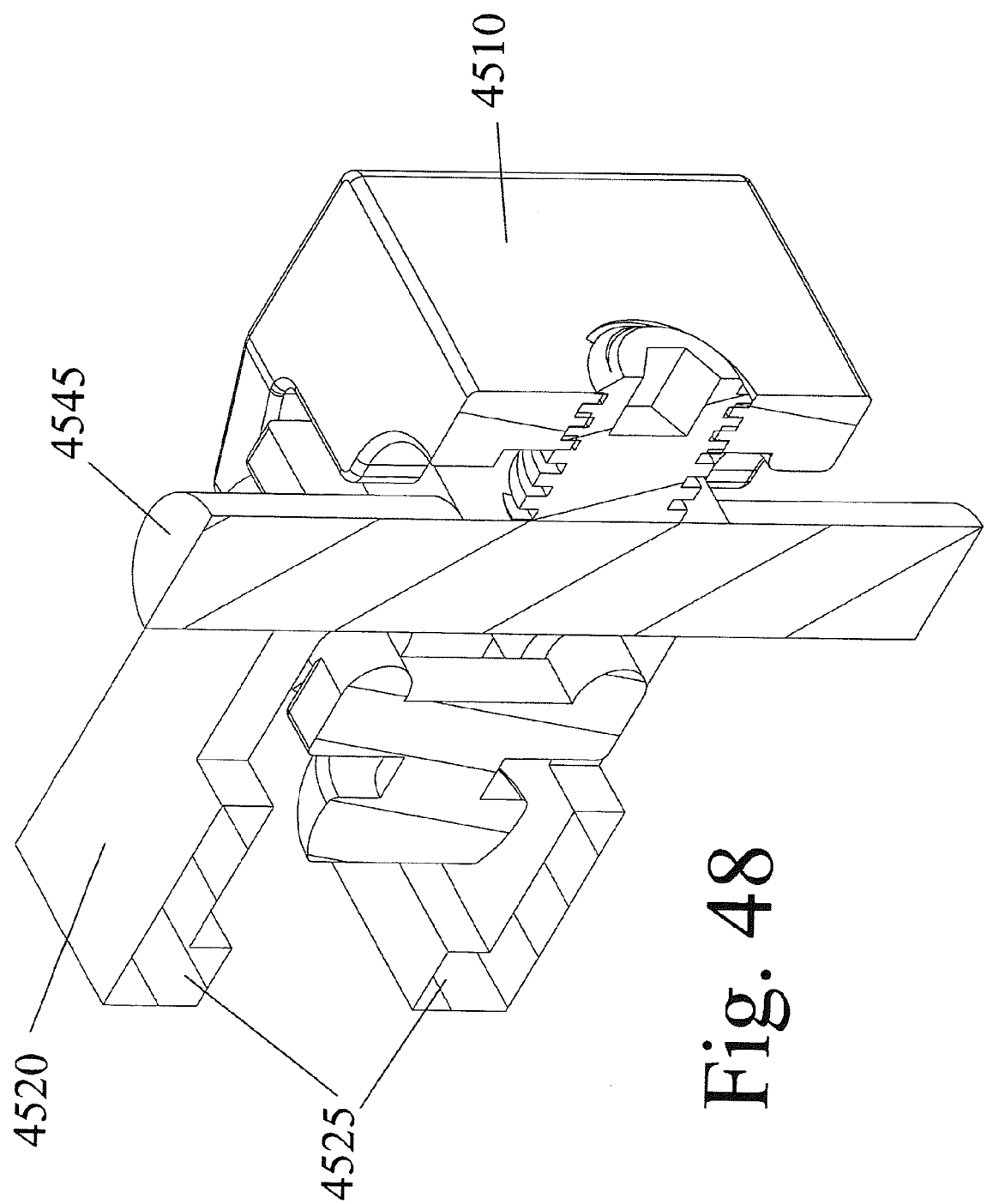
FIG. 48 shows a cross-sectional view of the attachment device.

FIG. 47 shows an enlarged, exploded view of the attachment member 4125 positioned adjacent an attachment region of the insertion device 120. FIG. 48 shows a perspective, cross-sectional, assembled view of the attachment member 4125. The attachment member 4125 includes a main body 4510 having a rounded protrusion 4515 that can be positioned inside the proximal end of the post 4110. A pair of side walls 4520 having inwardly extending teeth 4525 are positioned on opposite sides of the main body 4510. As mentioned, the structural configuration of the attachment member 4125 can vary and is not limited to the embodiment described herein.

With reference to FIG. 47, the attachment member 4125 is attached to the post 4110 115 by inserting the rounded protrusion 4515 into the proximal end of the post 4110. The two side walls 4520 are positioned on either side of the post 4110 such that each tooth 4525 engages a corresponding slot 4530 on the post 4110. In this manner, the attachment member 4125 is attached to the post 4110.

With reference to FIGS. 47 and 48, a pivot rod member 4540 is positionable inside the main body 4510. The pivot rod member4 540 includes a pivot rod 4545 that protrude outwardly from opposed sides of the main body 4510 when the pivot rod member 540 is positioned inside the main body 4510. The pivot rod 4545 can be inserted into a pair of apertures 4555 (FIG. 47) on the insertion device 120 to pivotably couple the insertion device 120 to the post 4110 via the attachment member 4125. The pivot rod 545 defines the pivot axis B (FIG. 46) for pivoting of the insertion device 120.

Figure 49:
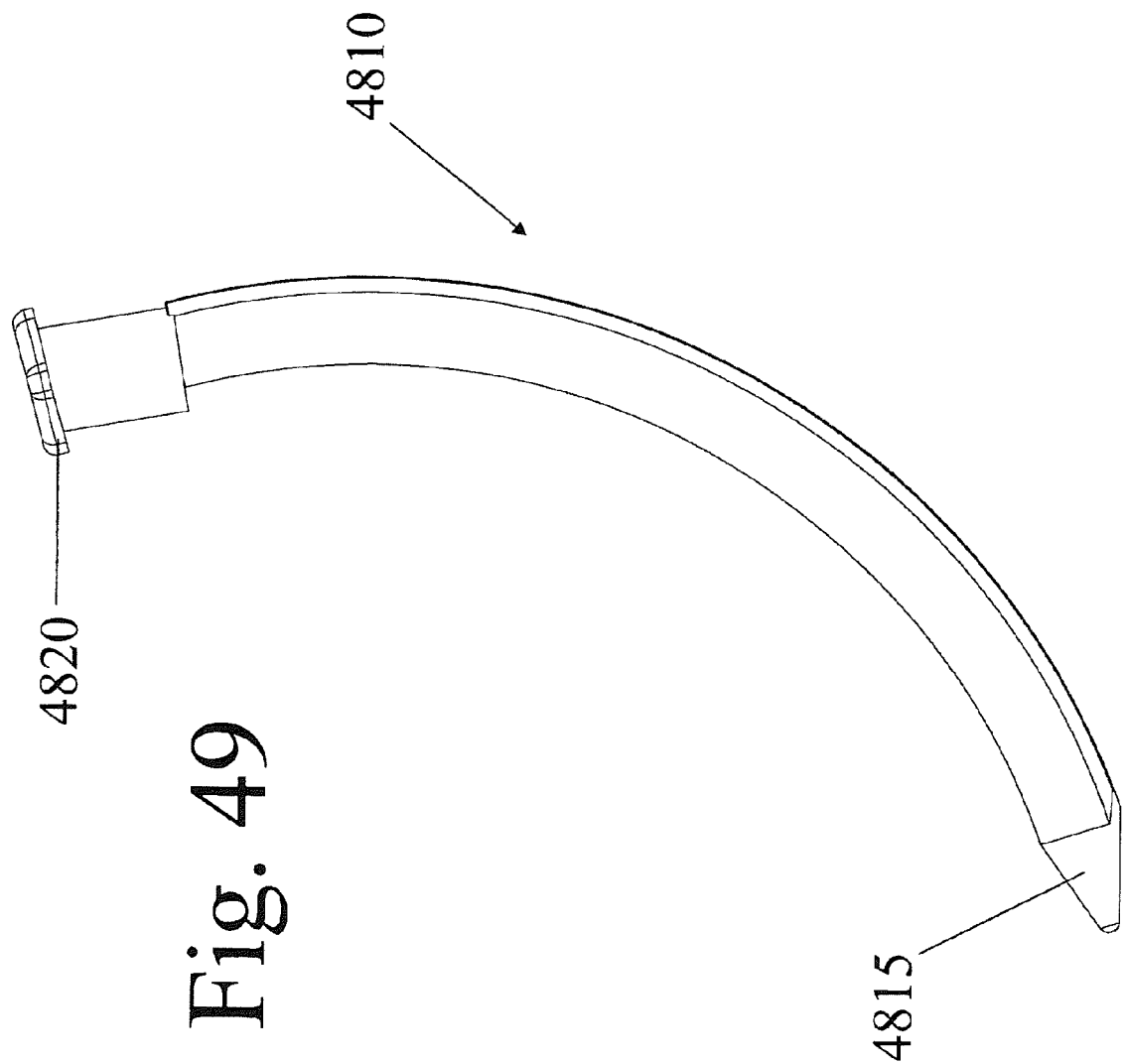
FIG. 49 shows a side view of a plunger that couples into the insertion device.
Figure 50:
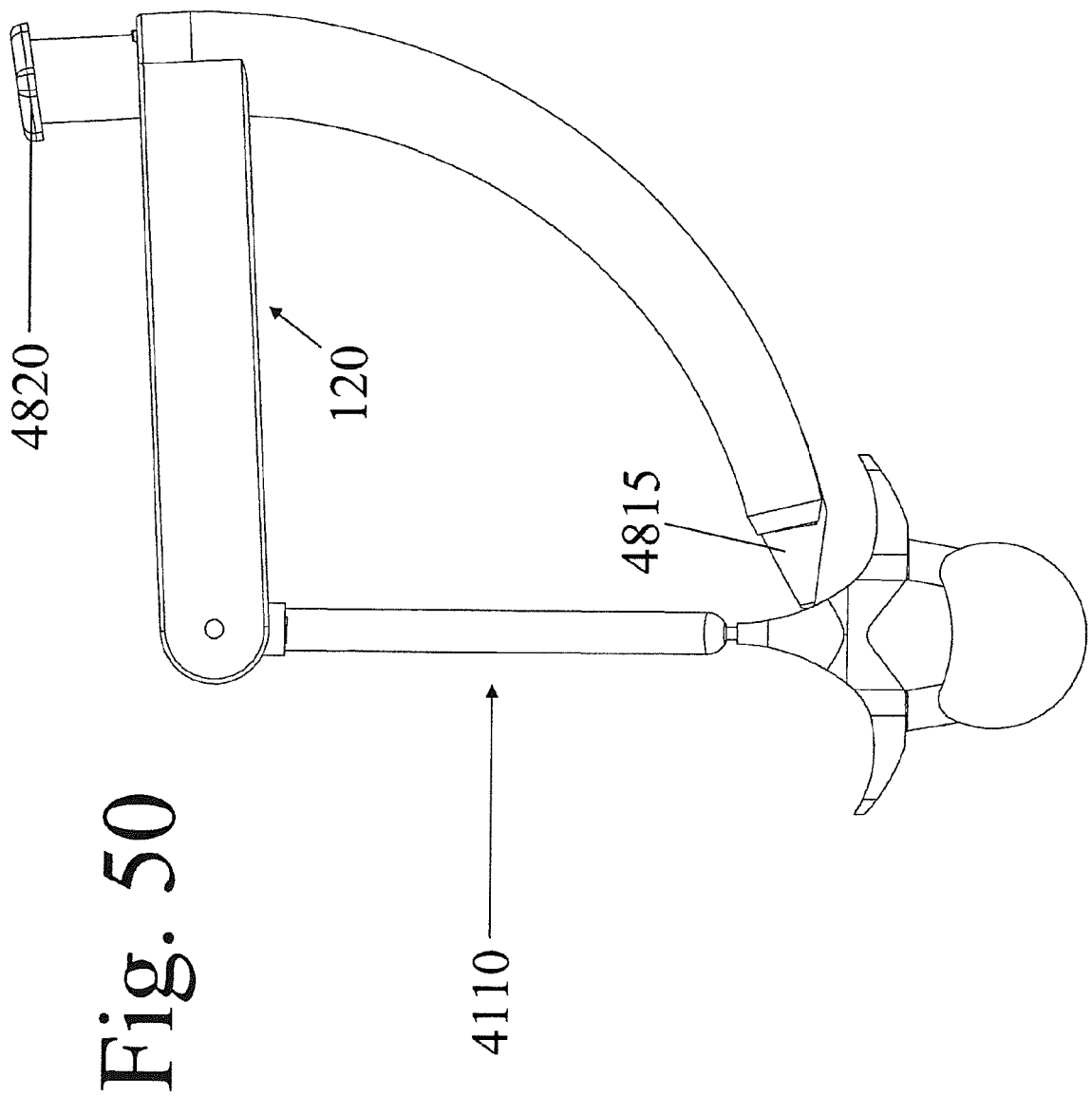
FIG. 50 shows a side view of the device with the plunger positioned inside the curved portion of the insertion device.

FIG. 49 shows a side view of an elongate plunger 4810 that slidably fits within a guide shaft inside the curved portion 140 of the insertion device 120. The plunger 4810 has a tapered tip 4815 on a distal end and a handle 4820 on a proximal end. When the plunger 4810 is fully positioned in the guide shaft, the handle 4820 protrudes out of one end of the guide shaft and the tapered tip 4815 protrudes out of the opposite end of the guide shaft. FIG. 50 shows a side view of the device with the plunger 4810 positioned inside the curved portion 140 of the insertion device 120.

Figure 51:
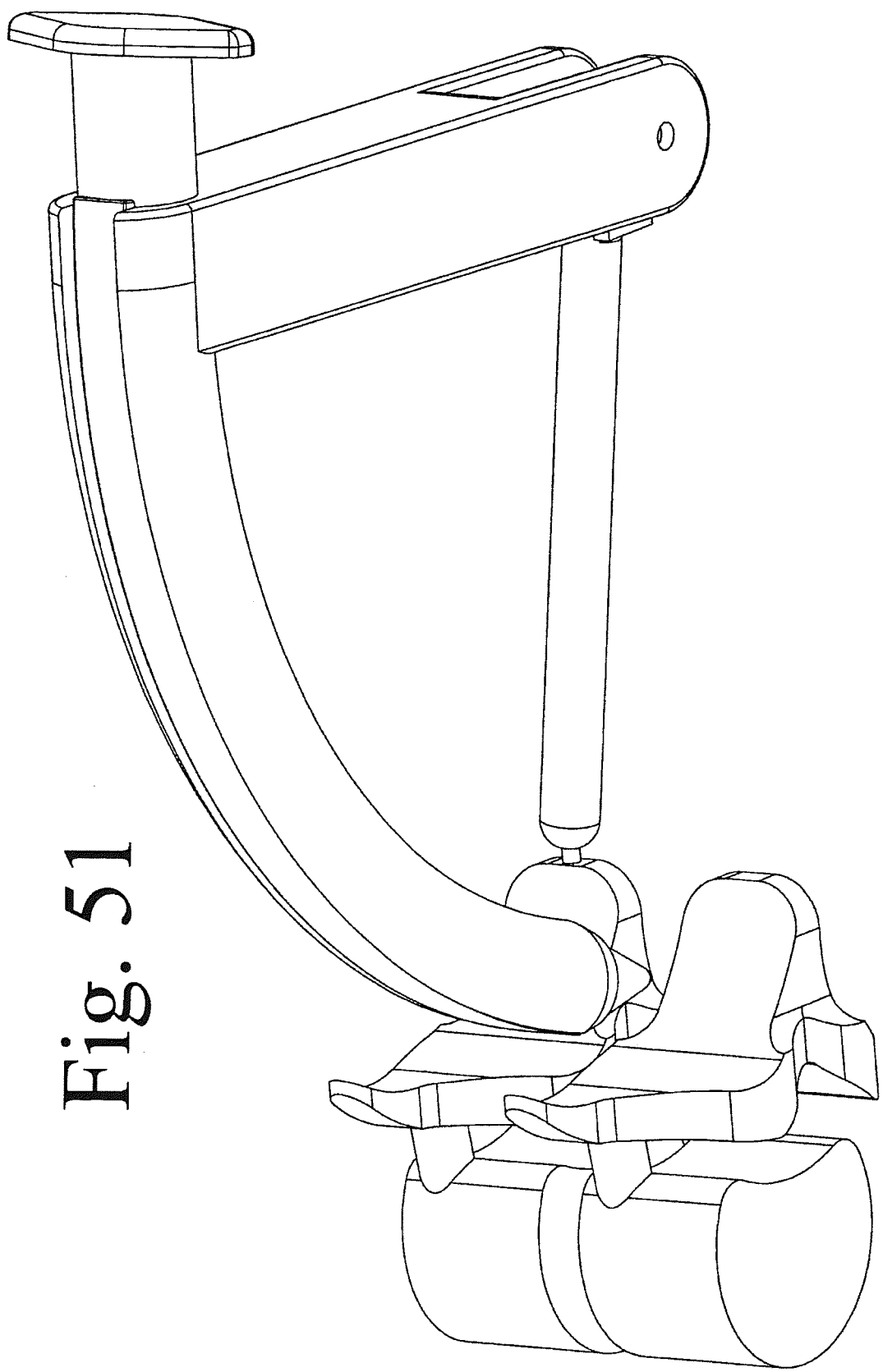
FIG. 51 shows a perspective view of the insertion device with a tapered end contacting the lateral side of the inter-spinous space.

With the insertion device 110 attached to the post 4110, the handle 4820 of the plunger 4810 is then used to push curved portion 140 toward the skin. As the tip 4815 abuts the skin, a small incision is made and the curved portion is then rotated further until the tapered end 4815 contacts the lateral side of the inter-spinous space, as shown in FIG. 50 and FIG. 51.

The plunger 4810 is removed and an orthopedic device can then be placed into the inter-spinous space through the guide shaft comprised of open curvilinear central bore of the curved portion 140. In this way, a device can be precisely delivered into the inter-spinous space with minimal tissue dissection. This method will provide a minimally invasive way of implanting orthopedic devices into this space.

In other embodiments, one or more anchors may be placed into the inter-spinous ligament, lateral to the inter-spinous space, into the pedicles or any other suitable anchor point. The insertion device is then attached and rotated onto the lateral aspect of the inter-spinal space. Lastly, the curved portion 140 of the insertion device 120 may be designed without a central bore for implant insertion. Instead, the implant is attached to the tip of the curved portion 140 and delivered by rotation of the curved portion. Once in place, the implant is detached from the insertion device 120.

Figure 52:
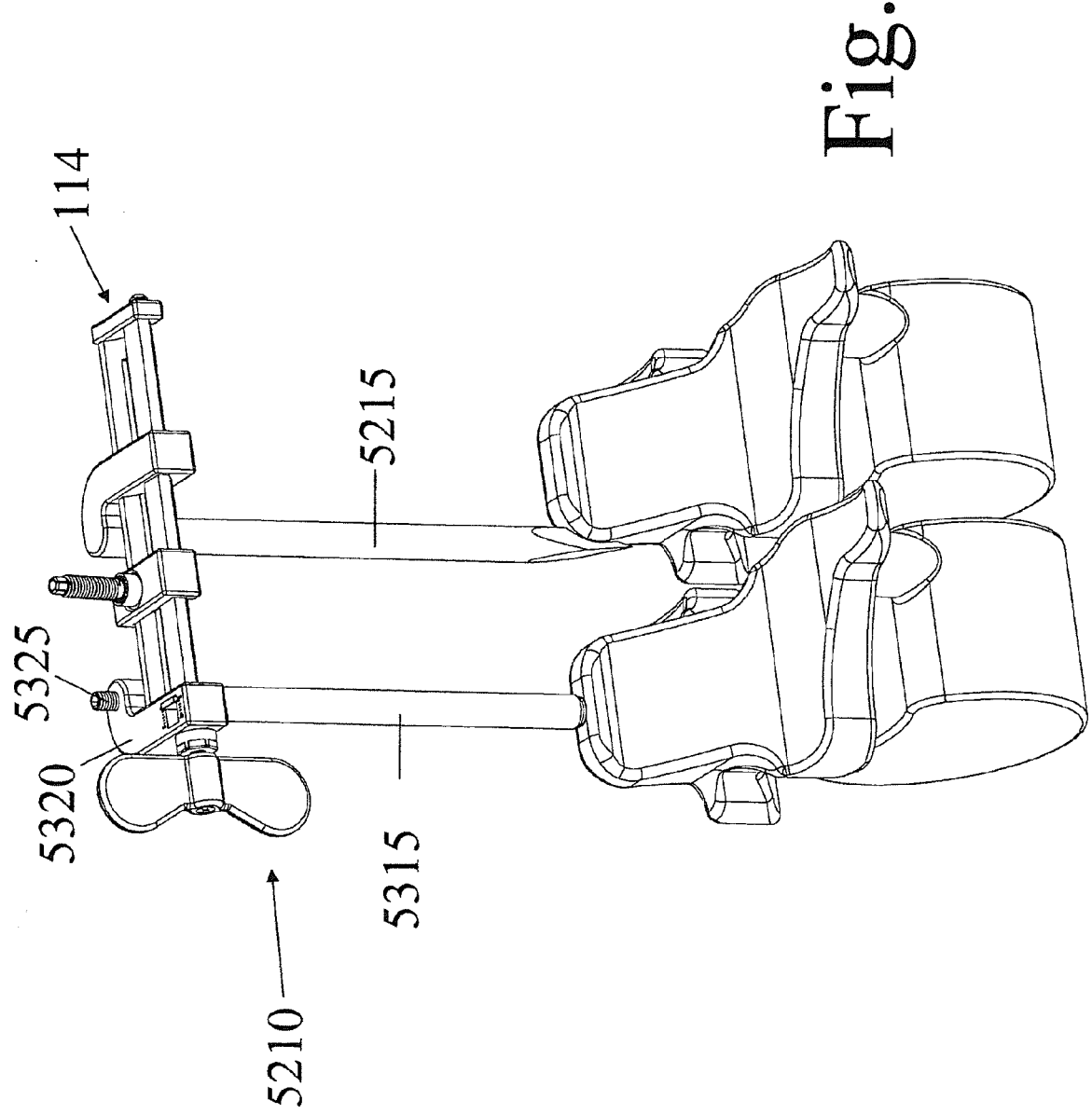
FIG. 52 shows a perspective view of another embodiment of a distractor device coupled to vertebral bodies.

FIGS. 52 and 53 shows another embodiment of a distractor device 5210 that is similar to the distractor device 100 described above. In this embodiment, the distractor device 5210 is attached to a pair of distractor members 5315 and 5215 that engage the first and second vertebral bodies. The distractor member 5215 is an elongate rod having a sharpened distal end for penetrating the skin. As shown in FIG. 53, the distal end does not penetrate the vertebral body but rather engages the vertebral body by abutting a side of the vertebral body.

It should be appreciated that the distractor members can engage the vertebral bodies in various ways. For example, the distractor members can be anchors with shanks that actually penetrate into the vertebral bodies. The distractor members can also be clamps that clamp onto the vertebral bodies or can simply by shaped to abut a portion of the vertebral body to purchase onto the vertebral body for distraction purposes. In addition, one of the distractor members can engage a first vertebral body in one manner (such as by penetrating the vertebral body) and the other distractor member can engage a vertebral body in another manner, such as by simply abutting or clamping onto the vertebral body. Alternately, both distractor members can simply abut a respective vertebral body without any penetration of the vertebral bodies by the distractor members.

As shown in FIG. 53, the distractor member 5215 has a structural configuration wherein an anchor 5310 anchors into the respective vertebral body. The anchor 5310 fits into a sheath 5315 that extends downward from a member 5320 on a platform 114. A vertical adjustment actuator 5325 is located on the member 5320 for adjusting the vertical position of the platform 114 in the manner described above with reference to the previous embodiment.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An instrument assembly for delivery of an orthopedic implant to a target location within a body of a subject, comprising:
    an implant insertion member comprising an elongated curvilinear body and an internal bore, at least a segment of said internal bore configured to extend from a proximal opening to a distal opening along a curvilinear trajectory, and sized to permit advancement of said implant through said internal bore;
    a plunger configured to be seated within said internal bore of said implant insertion member during an advancement of said implant insertion member onto said target location;
    a fixation member, comprising a first segment configured to attach onto a proximal segment of said implant insertion member and configured to limit movement of said implant insertion member relative to said target location in at least one plane by attachment of a second segment onto at least one surface outside said target location; and
an orthopedic implant configured to advance from said proximal opening to said distal opening of said internal bore and onto said target location after removal of said plunger.

2. The instrument assembly of claim 1, wherein said implant is affixed to an implant holder prior to insertion into said internal bore of said insertion member, said implant holder being sized and configured to advance at least partially through said internal bore of said implant insertion member.

3. The instrument assembly of claim 2, wherein said implant holder comprises a lock configured to retain said implant onto said holder.

4. The instrument assembly of claim 2, wherein said implant holder is configured to extend along an axis from a proximal segment adapted to be held by an operator to a distal segment adapted to be affixed to said implant; and
wherein at least a segment of said axis follows a curvilinear trajectory.

5. The instrument assembly of claim 2, wherein said plunger is further configured to extend from a proximal end to a distal end for a first distance and along an axis, at least a segment of said axis comprising a curvilinear trajectory.

6. The instrument assembly of claim 5, wherein said distal end of said plunger is tapered, and said first distance of said plunger is greater than a length of said internal bore of said implant insertion member.

7. The instrument assembly of claim 5, wherein said orthopedic implant is prevented from delivery onto said target location when said plunger is positioned therein.

8. The instrument assembly of claim 1, further comprising a sizing device configured to determine a size of a required implant for implantation, said sizing device configured to extend along an axis from a proximal segment to a distal segment, at least a segment of said axis comprising a curvilinear trajectory.

9. The instrument assembly of claim 8, wherein said sizing device is sized and configured to advance at least partially through said internal bore of said implant insertion member.

10. The instrument assembly of claim 1, wherein said first segment of said fixation member is configured to be retained outside of a body cavity of said subject during implant placement.

11. The instrument assembly of claim 1, wherein said first and second segments of said fixation member are configured to cooperatively articulate via ball and socket articulation.

12. The instrument assembly of claim 1, wherein said fixation member further comprises at least one deployable lock configured to transition to a locked state and immobilize said first segment relative to said second segment.

13. An instrument assembly for delivery of an orthopedic implant to a target location within a body of a subject, comprising:
an implant insertion member comprising an elongated curvilinear member having an internal bore;
a fixation member configured to attach to a proximal segment of said implant insertion member at a first segment thereof, and to at least partly limit movement of said implant insertion member relative to said target location after attachment of a second segment thereof onto at least one surface that is outside of said target location; and
a plunger configured to be seated within said internal bore of said implant insertion member, said orthopedic implant being prevented from delivery to said target location when said plunger is seated within said internal bore;
wherein at least a segment of said internal bore of said implant insertion member is configured to extend along a curvilinear trajectory from a proximal opening of a proximal end to a distal opening at a distal end of said implant insertion member; and
wherein said orthopedic implant is configured to be advanced from said proximal opening to said distal opening of said internal bore and onto said target location after removal of said plunger.

14. The instrument assembly of claim 13, wherein said orthopedic implant is configured to be affixed to an implant holder prior to insertion into said internal bore of said insertion member, said implant holder being sized and configured to be advanced at least partially through said internal bore of said implant insertion member, and said implant holder configured to detach from said orthopedic implant after said orthopedic implant is positioned at said target location.

15. The instrument assembly of claim 14, wherein said implant holder comprises a lock configured to retain said orthopedic implant onto said implant holder.

16. The instrument assembly of claim 14, wherein said implant holder extends along an axis from a proximal segment configured to be held by an operator, to a distal segment configured to be affixed to said orthopedic implant, at least a segment of said axis comprising a curvilinear trajectory.

17. The instrument assembly of claim 13, wherein said first segment of said fixation member configured to attach to said proximal segment of said implant insertion member is retained outside of a body cavity of said subject during implant placement.

18. The instrument assembly of claim 13, wherein the fixation member further comprises at least one deployable lock configured to transition to a locked state and immobilize at least a portion of said fixation member relative to another portion thereof.

19. An instrument assembly for delivery of an orthopedic implant to a target location within a body of a subject, comprising:
an implant insertion member, said implant insertion member comprising:
an elongated curvilinear member configured to extend from a proximal end to a distal end and having a radius and center of curvature;
an internal bore within said elongated curvilinear member and configured to extend from an opening of said proximal end to an opening of said distal end; and
a segment extending in a radial direction from a proximal aspect of said implant insertion member;
a fixation member configured to attach to said segment of said implant insertion member at a first segment thereof, said fixation member further configured to limit movement of said implant insertion member relative to said target location by attachment of a second segment thereof onto at least one surface outside said target location;
an orthopedic implant configured to be advanced from said opening of said proximal end to said opening of said distal end of said internal bore and onto said target location; and
a plunger configured to be removably seated within said internal bore of said implant insertion member during an advancement of said implant insertion member onto said target location, a removal thereof enabling said advancement of said orthopedic implant onto said target location:

wherein said elongated curvilinear member of said implant insertion member is further configured to pivotably rotate about said center of curvature and to position said distal end of said internal bore in proximity to said target location.

20. The instrument assembly of claim 19, wherein said orthopedic implant is configured to be affixed to an implant holder prior to insertion into said internal bore of said insertion member, said implant holder being sized and configured to he advanced at least partially through said internal bore of said implant insertion member, and said implant holder configured to detach from said orthopedic implant after said orthopedic implant is positioned at said target location.

21. The instrument assembly of claim 19, wherein the plunger extends from a proximal end to a distal end for a first distance and along an axis, and at least a segment of said axis follows a curvilinear trajectory.

22. The instrument assembly of claim 21, wherein said first distance of said plunger is greater than a length of said internal bore of said implant insertion member.

23. The instrument assembly of claim 19, wherein a distal end of said plunger is tapered.

24. The instrument assembly of claim 19, wherein said orthopedic implant is prevented from delivery to said target location when said plunger is seated within said internal bore.

25. The instrument assembly of claim 19, further comprising a sizing device configured to determine a size of said orthopedic implant for implantation, said sizing device further configured to:

extend along an axis from a proximal segment to a distal segment, at least a segment of said axis comprising a curvilinear trajectory; and be advanced at least partially through said internal bore of said implant insertion member.

26. The instrument assembly of claim 19, wherein said fixation member further comprises at least two segments configured to cooperatively articulate via a ball and socket articulation.

27. An instrument assembly for delivery of an orthopedic implant to a target location within a body of a subject, comprising:

an implant insertion member, said implant insertion member comprising:

an elongated curvilinear member configured to extend from a proximal end to a distal end and having a radius and center of curvature;

an internal bore within said elongated curvilinear member and configured to extend from an opening of said proximal end to an opening of said distal end; and a segment extending in a radial direction from a proximal aspect of said implant insertion member;

a fixation member comprising at least two segments configured to cooperatively articulate via a ball and socket articulation and configured to attach to said segment of said implant insertion member at a first segment thereof, said fixation member further configured to limit movement of said implant insertion member relative to said target location by attachment of a second segment thereof onto at least one surface outside said target location; and an orthopedic implant configured to be advanced from said opening of said proximal end to said opening of said distal end of said internal bore and onto said target location;

wherein said elongated curvilinear member of said implant insertion member is further configured to pivotably rotate about said center of curvature and to position said distal end of said internal bore in proximity to said target location.

28. The instrument assembly of claim 27, wherein said orthopedic implant is configured to be affixed to an implant holder prior to insertion into said internal bore of said insertion member, said implant holder being sized and configured to be advanced at least partially through said internal bore of said implant insertion member, and said implant holder configured to detach from said orthopedic implant after said orthopedic implant is positioned at said target location.

29. The instrument assembly of claim 27, further comprising a plunger configured to be at least partly seated within said internal bore of said implant insertion member during an advancement of said implant insertion member onto said target location.

30. The instrument assembly of claim 29, wherein the plunger extends from a proximal end to a distal end for a first distance and along an axis, and at least a segment of said axis follows a curvilinear trajectory.

31. The instrument assembly of claim 30, wherein said first distance of said plunger is greater than a length of said internal bore of said implant insertion member.

32. The instrument assembly of claim 29, wherein a distal end of said plunger is tapered.

33. The instrument assembly of claim 29, wherein said orthopedic implant is prevented from delivery to said target location when said plunger is seated within said internal bore.

34. The instrument assembly of claim 27, further comprising a sizing device configured to determine a size of said orthopedic implant for implantation, said sizing device further configured to:

extend along an axis from a proximal segment to a distal segment, at least a segment of said axis comprising a curvilinear trajectory; and be advanced at least partially through said internal bore of said implant insertion member.

* * * * *